United States Patent [19]

Seto et al.

[11] Patent Number: 4,745,050

[45] Date of Patent: May 17, 1988

[54] SILVER HALIDE COLOR PHOTOGRAPHIC MATERIAL AND DISCOLORATION INHIBITOR THEREFOR

[75] Inventors: Nobuo Seto; Masakazu Morigaki; Nobuo Sakai, all of Minami-ashigara, Japan

[73] Assignee: Fuji Photo Film Co., Ltd., Kanagawa, Japan

[21] Appl. No.: 823,365

[22] Filed: Jan. 28, 1986

[30] Foreign Application Priority Data

Jan. 29, 1985 [JP] Japan .................................. 60-15197
Feb. 2, 1985 [JP] Japan .................................. 60-19093
Feb. 2, 1985 [JP] Japan .................................. 60-19094

[51] Int. Cl.$^4$ ......................... G03C 7/26; G03C 7/38
[52] U.S. Cl. ..................................... 430/551; 430/544; 430/555
[58] Field of Search ....................... 430/544, 555, 551

[56] References Cited

U.S. PATENT DOCUMENTS

| | | | |
|---|---|---|---|
| 3,227,554 | 1/1966 | Barr et al. ............................ | 430/555 |
| 4,113,495 | 9/1978 | Shishido et al. ..................... | 430/551 |
| 4,264,720 | 4/1981 | Hamaoka et al. .................... | 430/551 |
| 4,264,723 | 4/1981 | Ichijama et al. ..................... | 430/555 |
| 4,310,623 | 1/1982 | Watanabe et al. ................... | 430/551 |
| 4,351,897 | 9/1982 | Acki et al. ............................ | 430/551 |
| 4,383,027 | 5/1983 | Ishikawa et al. ..................... | 430/551 |
| 4,556,630 | 12/1985 | Furutachi et al. ................... | 430/555 |

*Primary Examiner*—Richard L. Schilling
*Attorney, Agent, or Firm*—Birch, Stewart, Kolasch & Birch

[57] ABSTRACT

There is provided a silver halide color photographic material containing a 6-hydroxychroman derivative in, combination with a specific coupler, i.e., a 5-pyrazolone type magenta coupler having an —SR group at the coupling position or a 5-pyrazolone type magenta coupler having an anilino group at the 3-position. The photosensitive material provides photographic images, quality of which is prevented from deteriorating as time passes. The photographic color images are free from discoloration or fading and do not form yellow stains on a white background.

25 Claims, No Drawings

SILVER HALIDE COLOR PHOTOGRAPHIC MATERIAL AND DISCOLORATION INHIBITOR THEREFOR

BACKGROUND OF THE INVETNION

1. Field of the Invention

The present invention relates to a silver halide color photographic material. More particularly, it relates to a color photosensitive material which is so designed as to prevent dye images eventually obtained by development from fading or discoloration and noncolor-developed portions (hereafter referred to as "white background") from discoloration.

2. Description of the Prior Art

Generally photographic images formed by a silver halide photographic material does not keep its quality permanently, but it deteriorates as time lapses during preservation. This is particularly true of color photography having images made up of azomethine dyes or indoaniline dyes formed by a reaction of a coupler with oxidation products of the aromatic primary amine developing agents. Such color photography undergoes discoloration or fading of dye images and discoloration of a white background when exposed to light for a prolonged period of time or preserved under heat and humidity exposure conditions.

The deterioration of the quality of image is detrimental to a recording material. In order to prevent the image from deterioration, there have been made a large number of proposals. The most effective proposal among them is to use a color image stabilizer in combination with a coupler. A phenolic compound is the typical example of such a compound. The compound having the ether linkage at the p-position is relatively high in the prevention of discoloration effect. Examples of such compounds are alkoxy- or aryloxyphenols, hydroxycoumarans, hydroxychromans, and hydroxyspirochromans as disclosed in U.S. Pat. Nos. 3,432,300, 3,573,050, 3,574,627, 3,698,909, 3,764,337, 3,930,866, 4,120,723, 4,113,488, 4,264,720, and 4,388,404; British Pat. No. 2,066,975 (B); West Germany Pat. (OLS) Nos. 2,146,668 and 2,726,283; Japanese Patent Application (OPI) Nos. 14023/1976, 124926/1976, and 53321/1978; and Japanese Patent Publication Nos. 20537/1981. 40817/1981, and 10539/1984.

Another compounds known in the art are phenolic compounds having the ether linkage at the p-position in which the hydroxyl group is etherified or silyletherified, as disclosed in U.S. Pat. Nos. 4,155,765, 4,254,216, and 4,279,990.

Although these compounds are effective in preventing color images from fading and/or discoloration, they are still unsatisfactory as a color image stabilizer which must satisfy several requirements for photography. Some of them are less in effectiveness and deleterious to the hue even though they are effective against discoloration, and others cause fogging, poor dispersion, or crystallization.

Among the phenolic compounds having the ether linkage at the p-position, α-tocopherol is known as a natural antioxidant while 6-hydroxychroman is known as a compound effective for the prevention of discoloration as disclosed in U.S. Pat. Nos. 3,432,300 and 3,698,909; and Japanese Patent Application (OPI) No. 10539/1984.

U.S. Pat. No. 4,113,495 discloses compounds having hydroquinone at the 2-position of the chroman ring, and U.S. Pat. No. 4,264,720 discloses compounds having hydroquinone diether at the 2-position of the chroman ring.

As a result of the recent improvement in color photographic materials which require more sophisticated properties in the color photography, the compounds disclosed in the above-mentioned patents are considered to be unsatisfactory in the preservability of photographic images. In other words, the compounds are not effective to prevent the change of photographic image density, the change of color balance of yellow, magenta, and cyan after discoloration, and the staining of the white background which occur due to light, heat, and moisture during preservation of the photography.

BRIEF SUMMARY OF THE INVENTION

Accordingly, it is a first object of the present invention to provide a silver halide color photographic material which contains a stabilizer to prevent quality of photographic images from deteriorating as time passes.

It is a second object of the invention to provide a color photographic material which incorporates a stabilizer in an emulsion layer which is effective to prevent the color photographic images from fading or discoloring without causing hue change and fogging, thereby obtaining stabilized photographic color images.

It is a third object of the invention to provide a color photographic material which is free from discoloration and fading of photographic color images and any loss in the density of formed dyes in the color images.

It is a fourth object of the invention to provide a color photographic material which incorporates a stabilizer in a photographic layer and does not form yellow stains on unexposed portions of the photosensitive material when the photographic color image is exposed to light, heat, and moisture after development processing.

It is a fifth object of the invention to provide a color photographic material which is less in fading or discoloration over the entire density range of photographic color image formed by development processing and underwent no change in color balance.

It is a sixth object of the invention to provide an antioxidant which, because of its high antioxidant action which can be applied to the prevention of fading and discoloration of photographic color images formed by the subtractive color process and also applied to dyes, rubbers, plastics, and petroleum products and the like.

Other and further objects, features, and advantages of the invention will appear more fully from the following description.

DETAILED DESCRIPTION OF THE INVENTION

According to this invention, there is provided a silver halide color photographic material which contains a compound represented by formula (I) below.

In addition, according to this invention, there is provided a silver halide photosensitive material for color photography which contains at least one kind of the compound represnted by the formula (I) below and at least one kind of the pyrazolone type magenta coupler.

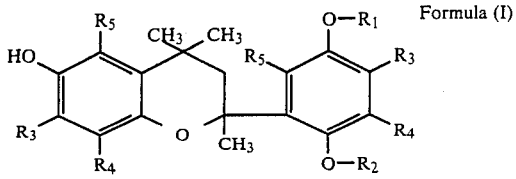

Formula (I)

wherein $R_1$ and $R_2$ each independently denotes a hydrogen atom, alkyl group, cycloalkyl group, heterocyclic group, trialkylsilyl group, alkanesulfonyl group, arylsulfonyl group, or —X—Y with the proviso that one of $R_1$ and $R_2$ is a hydrogen atom and that both $R_1$ and $R_2$ cannot be hydrogen atoms at the same time and X denotes a

group, and Y denotes an alkyl group, cycloalkyl group, aryl group, alkoxy group, aryloxy group, alkylamino group, dialkylamino group, arylamino group, diarylamino group, alkyloxycarbonyl group, aryloxycarbonyl group, or acyl group. $R_3$, $R_4$, and $R_5$, which may be the same or different, each independently denotes a hydrogen atom, alkyl group, cycloalkyl group, alkenyl group, aryl group, alkoxy group, aryloxy group, alkenoxy group, alkylthio group, arylthio group, acylamino group, diacylamino group, sulfoneamide group, alkylamino group, acyl group, alkoxycarbonyl group, acyloxy group, or halogen atom. If $R_1$, $R_2$, $R_3$, $R_4$, and $R_5$ are alkyl groups or aryl groups or those groups containing partially alkyl groups or aryl groups, such alkyl groups or aryl groups may be further substituted.

The compounds represented by formula (I) are preferably those which are represented by formula (X) below.

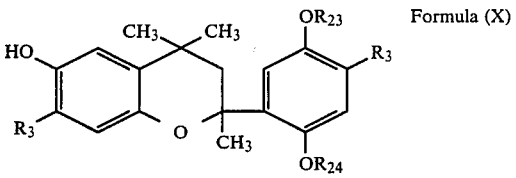

Formula (X)

wherein $R_3$ has the same meaning as in formula (I); and $R_{23}$ and $R_{24}$ each denote a hydrogen atom or alkyl group, provided that both of them are not hydrogen atoms or alkyl groups at the same time.

Preferably one of $R_{23}$ and $R_{24}$ is an alkyl group and the other is a hydrogen atom. $R_3$ should preferably be a methyl group from the standpoint of synthesis.

According to one embodiment of this invention, a compound represented by formula (I) above is combined with a pyrazolone type magenta coupler having at the coupling position a group represented by formula (II) below, providing remarkable improvements of fastness to light, heat, and humidity.

Formula (II)

—S—R wherein R denotes an alkyl group or aryl group, the alkyl group including linear or branched alkyl groups, aralkyl groups, alkenyl groups, cycloalkyl groups, and cycloalkenyl groups (e.g., n-dodecyl group, t-octyl group, benzyl group, cyclopentyl group, and cyclohexenyl group), and the aryl group including phenyl groups and naphthyl groups.

The 5-pyrazolone type magenta coupler having at the coupling position a group represented by formula (II) includes, for example, a compound represented by formula (III) below.

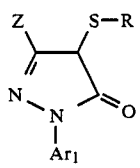

Formula (III)

wherein R is defined as in formula (II); $Ar_1$ denotes an aryl group; and Z denotes an acylamino group, anilino group, or ureido group.

The coupler represented by formula (III) is added in an amount of $2 \times 10^{-3}$ to $5 \times 10^{-1}$ mol, preferably $1 \times 10^{-2}$ mol or more.

The compounds represented by formula (III) are preferably those compounds represented by formula (IV) below.

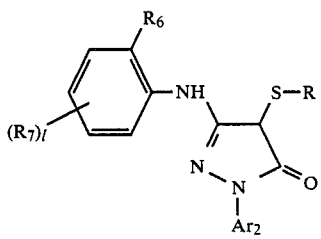

Formula (IV)

wherein R has the same meaning as in formula (II); $Ar_2$ denotes a phenyl group having at least one substituent selected from a halogen atom, alkyl group, alkoxy group, alkoxycarbonyl, or cyano group; $R_6$ denotes a halogen atom or alkoxy group; and $R_7$ denotes a hydrogen atom, halogen atom, alkyl group, alkoxy group, acylamino group, sulfoneamide group, sulfamoyl group, carbamoyl group, diacylamino group, alkoxycarbonyl group, alkoxysulfonyl group, aryloxysulfonyl group, alkanesulfonyl group, arylsulfonyl group, alkylthio group, arylthio group, alkyloycarbonylamino group, alkylureido group, acyl group, nitro group, carboxyl group, or trichloromethyl group; l is an integer of 1 to with the proviso when l is greater than 1, the groups represented by $R_7$ may be the same or different.

The compounds represented by formula (IV) are preferably those compounds in which —SR is the group represented by formula (V), (VI), or (VII) below.

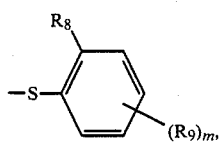

Formula (V)

-continued

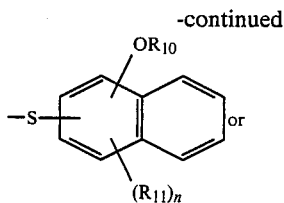 Formula (VI)

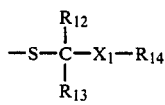 Formula (VII)

wherein $R_8$ denotes a halogen atom, hydroxyl group, alkyl group, alkoxyl group, or aryl group; $R_9$ denotes a hydrogen atom, halogen atom, hydroxyl group, alkyl group, alkoxyl group, or aryl group with the proviso that at least one of $R_8$ and $R_9$ is an alkoxyl group; $R_{10}$ denotes an alkyl group or aryl group; $R_{11}$ denotes a halogen atom, alkyl group, alkoxyl group, or aryl group; m is an integer of 1 to 4, and n is an integer of 1 to 5 with the proviso that when m or n is greater than 1, the groups represented by $R_9$ or $R_{11}$ may be the same or different; $R_{12}$ denotes a hydrogen atom, alkyl group, or aryl group; $R_{13}$ denotes a hydrogen atom, alkyl group, aryl group, alkoxyl group, aryloxy group, alkoxycarbonyl group, aryloxycarbonyl group, carbamoyl group, acyl group, or carboxyl group; $X_1$ denotes an alkylene group, alkenylene group, arylene group,

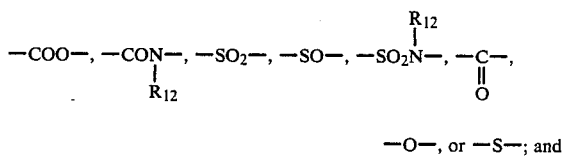

$-O-$, or $-S-$; and $R_{14}$ denotes a hydrogen atom, alkyl group, aryl group, or heterocyclic group. The sum of number of carbon atoms of $R_{13}$ and $R_{14}$ should preferably be 12 and up, and either $R_{12}$ or $R_{13}$ may combine with $R_{14}$ to form a 5- or 7-membered ring.

The compounds represented by formula (IV) are preferably those compounds represented by formula (VIII) below.

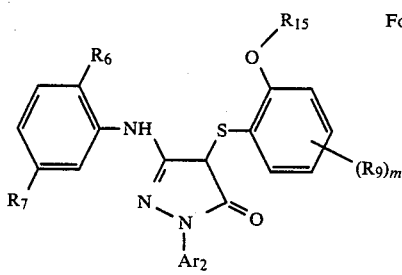 Formula (VIII)

wherein $Ar_2$, $R_6$, and $R_7$ are defined as in formula (IV); $R_9$ and m are defined as in formula (V); $R_{15}$ denotes an aliphatic group or aromatic group which may have (a) a halogen atom, (b) a cyano group, (c) an aliphatic, aromatic, or heterocyclic, sulfonyl group, sulfinyl group, or sulfonyl group, (d)

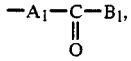

or (e) $-(A_2-M)_mB_2$, wherein $A_1$ denotes a single bond, oxygen atom, sulfur atom, imino group, or divalent aliphatic, aromatic, or heterocyclic group; $B_1$ denotes a hydroxyl group, aliphatic or aromatic oxy group, hydrogen atom, aliphatic group, aromatic group, heterocyclic group, or acyclic amino group or hydrazino group which may have a substituent group; $A_2$ denotes a single bond, or divalent aliphatic, aromatic, or heterocyclic group; $B_2$ denotes a hydrogen atom, aliphatic group, aromatic group, or heterocyclic group; M denotes an oxygen atom, sulfur atom, or imino group; and m denotes an integer of 1 to 4.

In this invention, a coupler preferable to the unsubstituted is the one represented by formula (VIII) having an aliphatic oxy or aromatic oxy group further substituted with at least one of the groups (a) to (e) given above.

$R_9$ and $R_{15}$ may be contiguous to each other forming a bis compound.

The "aliphatic group" as used herein denotes a linear, branched, or cyclic alkyl, alkenyl, or alkynyl group which may be saturated or unsaturated.

In more detail $Ar_2$ may include a substituted phenyl group, and the substituent group includes a halogen atom (e.g., chlorine atom, bromine atom, and fluorine atom), alkyl group having 1 to 22 carbon atoms (e.g., methyl group, ethyl group, tetradecyl group, and t-butyl group), alkoxyl group having 1 to 22 carbon atoms (e.g., methoxy group, ethoxy group, octyloxy group, and dodecyloxy group), alkoxycarbonyl group having 2 to 23 carbon atoms (e.g., methoxycarbonyl group, ethoxycarbonyl group, and tetradecyloxycarbonyl group), and cyano group.

Example of $R_6$ may include a halogen atom (e.g., chlorine atom, bromine atom, and fluorine atom) and alkoxyl group having 1 to 22 carbon atoms (e.g., methoxy group, octyloxy group, and dodecyloxy group).

Example of $R_7$ may include a hydrogen atom, halogen atom (e.g., chlorine atom, bromine atom, and fluorine atom), alkyl group (linear or branched alkyl group, aralkyl group, alkenyl group, cycloalkyl group, and cycloalkenyl group, e.g., t-butyl group, t-octyl group, tetradecyl group, benzyl group, allyl group, cyclopentyl group, and cyclohexenyl group), alkoxyl group (e.g., methoxy group, ethoxy group, 2-ethylhexyloxy group, and tetradecyloxy group), acylamino group (e.g., acetamido group, benzamido group, butanamido group, tetradecanamido group, α-(2,4-di-tert-amylphenyloxy) acetamido group, α-(2,4-di-tert-amylphenoxy) butylamido group, α-(3-pentadecylphenoxy) hexanamido group, α-(4-hydroxy-3-tert-butylphenoxy) tetradecanamido group, 2-oxo-pyrrolidin-1-yl group, 2-oxo-5-tetradecylpyrrolidin-1-yl group and N-methyl-tetradecanamido group), sulfonamido group (e.g., methanesulfonamido group, benzensulfonamido group, p-toluenesulfonamido group, octansulfonamido group p-dodecylbenzenesulfonamido group, and N-methyl-tetradecanesulfonamido group), sulfamoyl group (e.g., N-methyl-sulfamoyl group, N-hexadecylsulfamoyl group, N-[3-(dodecyloxy)-propyl] sulfamoyl group, N-[4-(2,4-di-tert-amylphenoxy)butyl) sulfamoyl group, and N-methyl-tetradecylsulfamoyl group), carbamoyl group (e.g., N-methylcarbamoyl group, N-octadecylcarbamoyl group, N-[4-(2,4-di-tert-amylphenoxy)- butyl]carbamoyl group, and N-methyl-N-tetradecylcarbamoyl group), diacylamino group (e.g., N-succinimido group, N-phthalimido group, 2,5-dioxo-1-oxazolidinyl group, 3-dodecyl-2,5-doxo-1-hydrantoinyl group, and 3-(N-acetyl-N-dodecylamino) succinimido group), alkoxycarbonyl group (e.g., methoxycarbonyl group, tetradecyloxycarbonyl group, and benzyloxycarbonyl group), alkoxysulfonyl group (e.g., methoxysulfonyl group, octyloxysulfonyl group, and tetradecyloxysulfonyl group), aryloxysulfonyl group (e.g., phenoxysulfonyl group and 2,4-di-tert-amylphenoxysulfonyl group), alkanesulfonyl group (e.g., methanesulfonyl group, octanesulfonyl group, 2-ethylhexanesulfonyl group, and hexandecanesulfonyl group), arylsulfonyl group (e.g., benzenesulfonyl group and 4-nonylbenzenesulfony group). alkylthio group (e.g., ehtylthio group, hexylthio group, benzylthio group, tetradecylthio group, and 2-(2,4-di-tert-amylphenoxy)ethylthio group), arylthio group (e.g., phenylthio group and p-tolylthio group), alkyloxycarbonylamino group (e.g., ethyloxycarbonylamino group, benzyloxycarbonylamino group, and hexadecyloxycarbonylamino group), alkylureido group (e.g., N-methyl ureido group, N,N-dimethylureido group, N-mehtyl-N-dodecylureido group, N-hexadecylureido group, and N,N-dioctadecylureido group), acyl group (e.g., acetyl group, benzoyl group, octadecanoyl group, and p-dodecanamidobenzoyl group), nitro group, carboxyl group, or trichloromethyl group. Among the above-mentioned substituent groups, the alkyl group indludes those which have 1 to 36 carbon atoms and the aryl group includes those which have 6 to 38 carbon atoms.

Examples of $R_9$ may include a halogen atom, alkyl group, alkoxyl group, acylamino group, ureido group, alkoxycarbonylamino group, imido group (synonymous with diacylamino group), sulfonamido group, sulfamoyl group, alkoxycarbonyl group, carbamoyl group, and alkylthio group which have the same meanings as described for $R_7$ above. In addition, $R_9$ denotes a hydrogen atom, hydroxyl group, aryl group (e.g., phenyl group, α- or β-naphthyl group, 2-chlorophenyl group, 4-acetamidophenyl group, 4-tert-butylphenyl group, and 4-cyanophenyl group), amino group (e.g., N-alkylamino group, N,N-dialkylamino group and anilino group (wherein N-alkylamino group includes N-butylamino group, N-(2-methoxyethyl)amino group, N-(2-methanesulfonylethyl)amino group, and N-(3-acetamidpropyl)amino group; N,N-dialkylamino group including N-N-dibutylamino group, N,N-dihexylamino group, N,N-bis(2-ethylhexylamino) group, N,N-bis(2-hexansulfonylethylamino) group, N-ethyl-N-dodecylamino group, N,N-bis(3-phenoxypropylamino) group, N-ethyl-N-[2-(2,4-di-tert-amylphenoxy)ethylamino) group, and N,N-bis{2-[(4-tert-butylphenoxy)acetamide]ethyl} group; and anilino group including phenylamino group, 4-methoxyphenylamino group, N-ethylphenylamino group, 2,4-di-tert-phenylamino group, 3-methanesulfonamidophenylamino group, and 2-chlorophenylamino group, sulfamoylamino group (e.g., N,N-dibutylsulfamoylamino group, N-ethyl-N-dodecylsulfamoylamino group, N-ethyl-N-anilinosulfamoylamino group, and N,N-bis(2-butane-sulfonylethyl)sulfamoylamino group), nitro group, acyl group (e.g., acetyl group, benzoyl group, hexanoyl group, 2,4-di-tert-butylbenzoyl group, 2-hydroxybenzoyl group, and decyloxyacetyl group), and cyano group.

Examples of $R_{15}$ may include a cyano group, halogen atom,

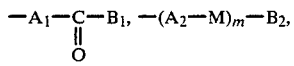

wherein $A_1$, $B_1$, $A_2$, $M$, $B_2$, and $m$ have the same meaning defined as above, or alkyl or aryl group having a sulfonyl, sulfinyl, or phosphonyl substituent group. Preferable example is an alkyl or aryl group having a substituent group selected from:

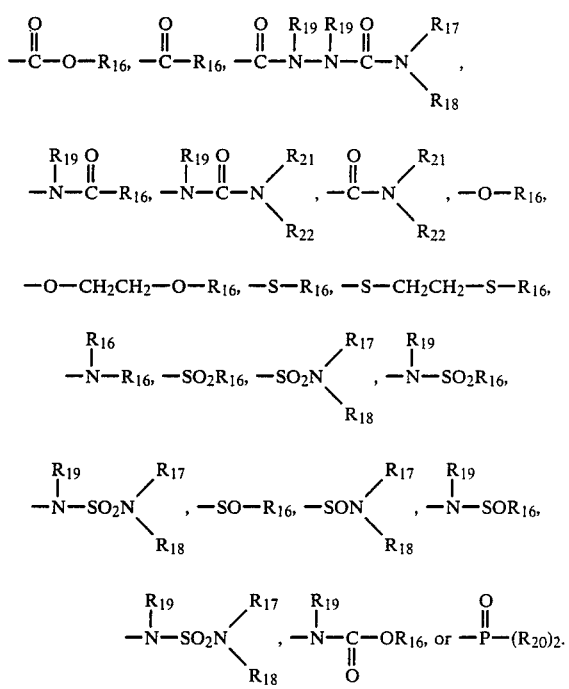

wherein: $R_{16}$ denotes a hydrogen atom, alkyl group, aryl group, or hetero cyclic group. $R_{17}$ and $R_{18}$ independently denote a hydrogen atom, alkyl group, aryl group, or heterocyclic group, or groups which may be connected to each other to form a 5-, 6-, or 7-membered nitrogen-hetro ring. $R_{19}$ denotes a hydrogen atom or alkyl group. $R_{20}$ denotes an alkyl group, alkoxyl group, aryl group, or aryloxy group. $R_{21}$ and $R_{22}$ independently denote a hydrogen atom, alkyl group, aryl group, or heterocyclic group. The alkyl group and aryl group represented by $R_{16}$ to $R_{22}$ may have the substituent group enumerated for $R_7$ and $R_8$.

$R_{15}$ should preferably be an alkyl group having the ether group, carbonyl group, sulfonyl group, or phosphonyl group mentioned above.

The following are typical examples of the above-mentioned magenta couplers.

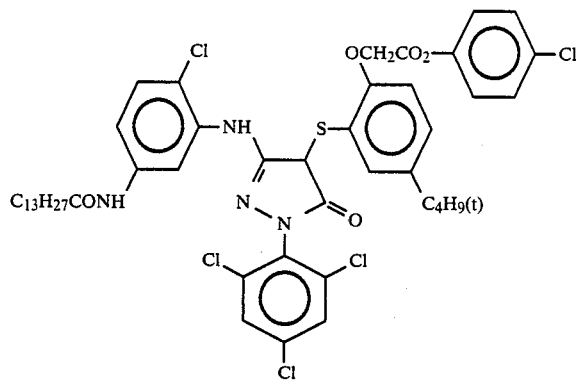
(M-1)
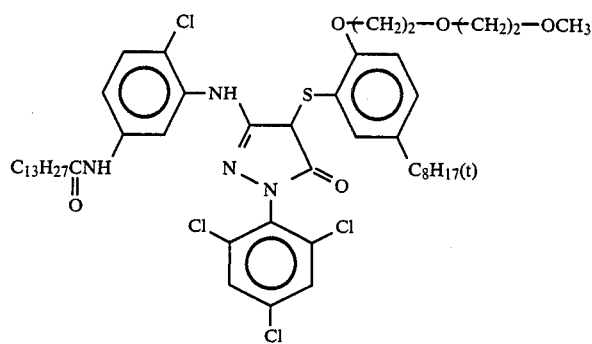
(M-2)
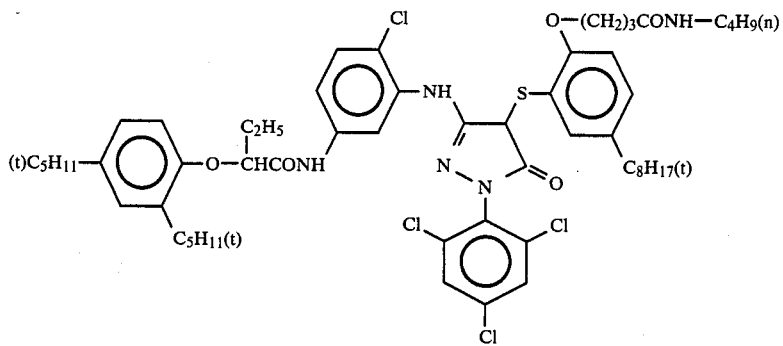
(M-3)
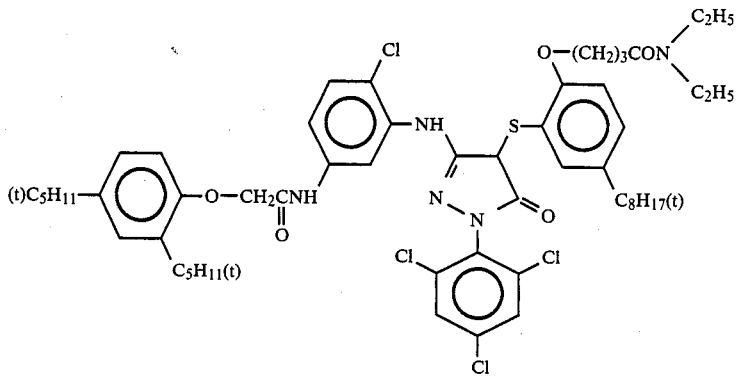
(M-4)

-continued
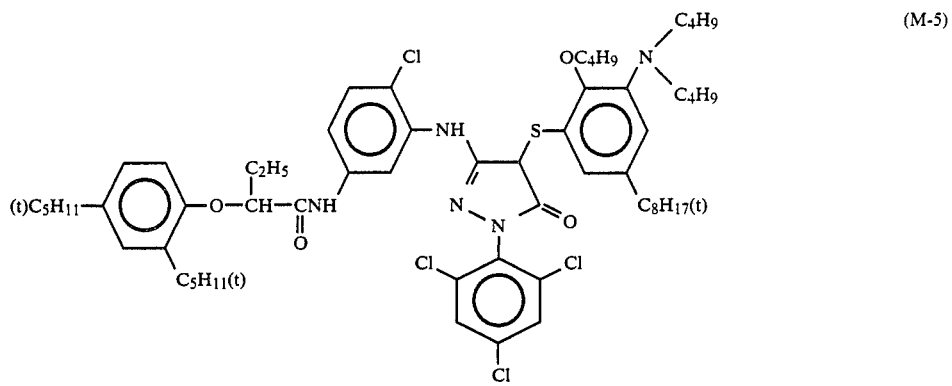
(M-5)
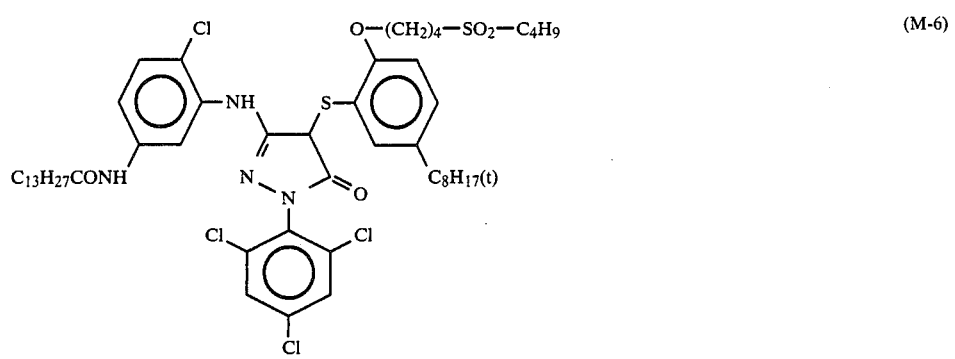
(M-6)
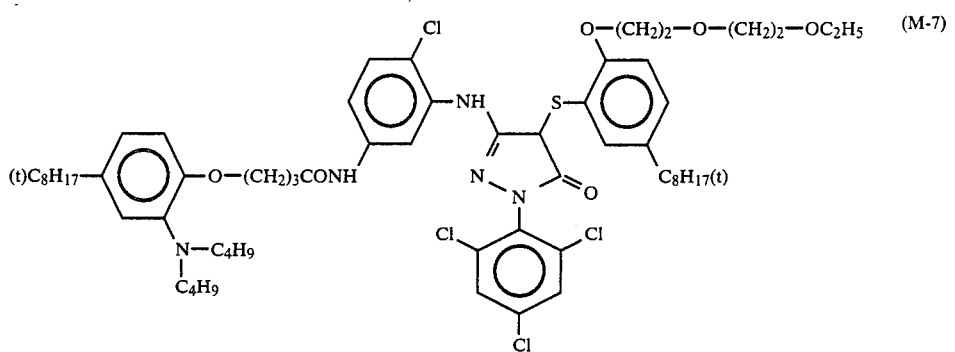
(M-7)
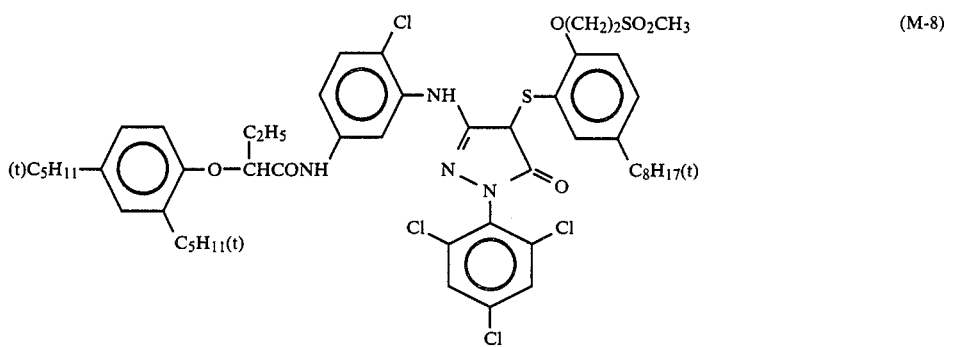
(M-8)

-continued
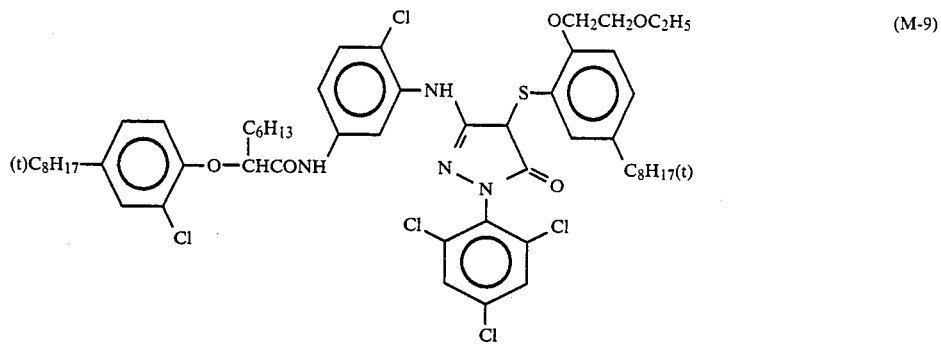 (M-9)
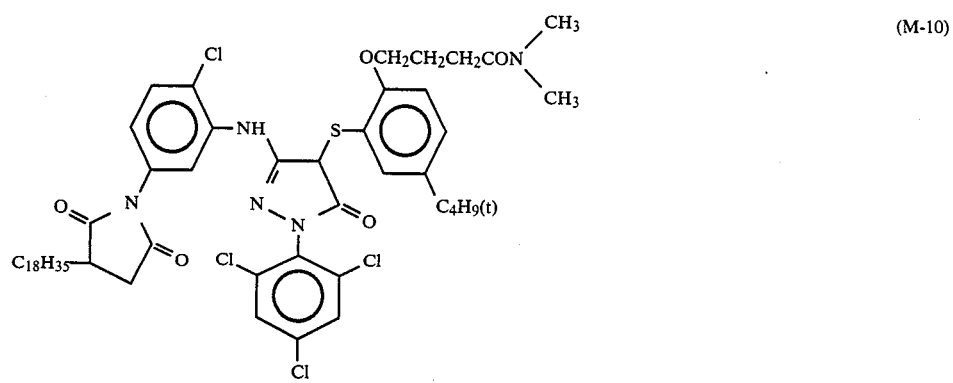 (M-10)
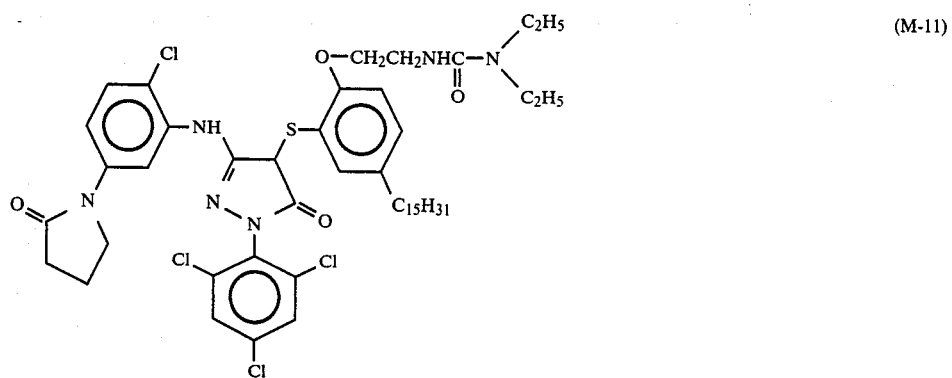 (M-11)
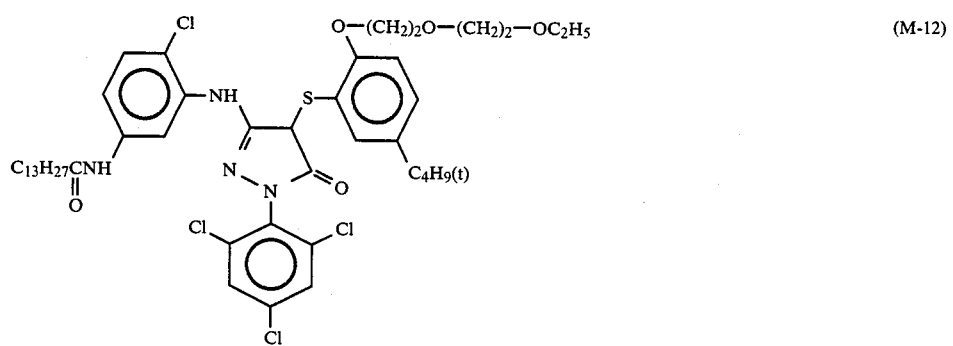 (M-12)

-continued
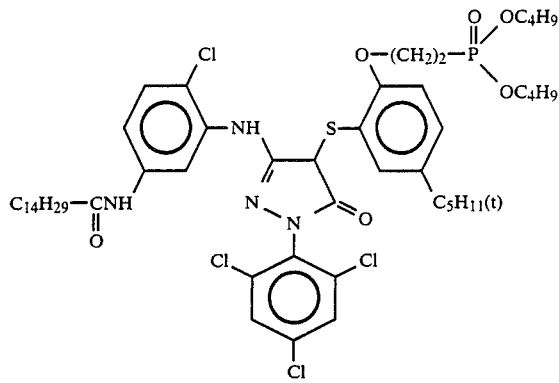
(M-13)
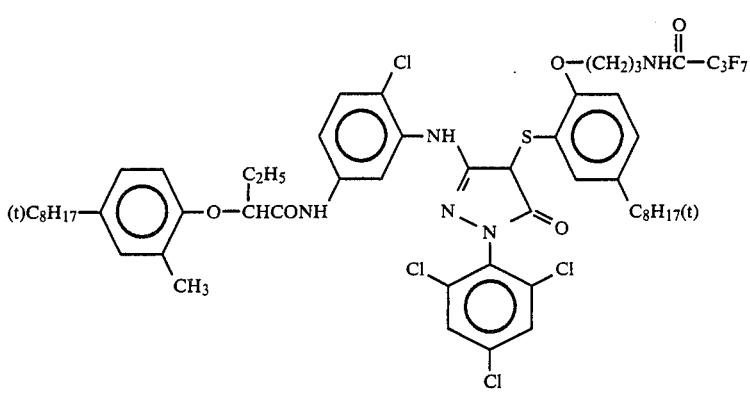
(M-14)
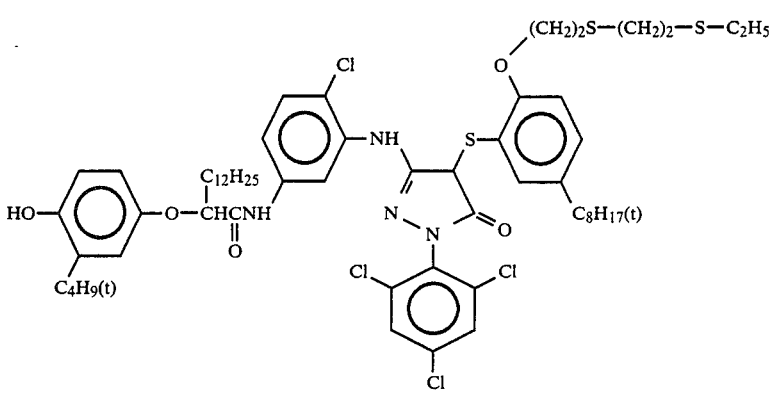
(M-15)
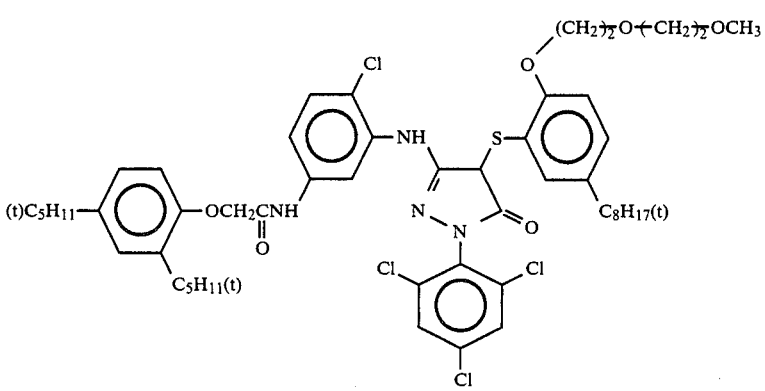
(M-16)

-continued
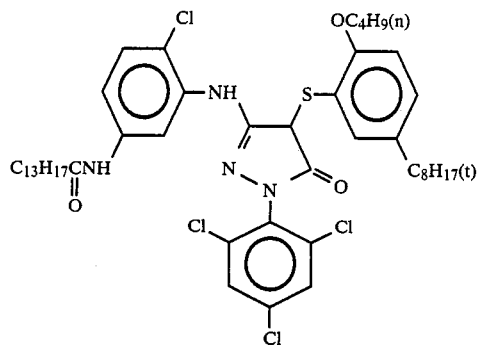 (M-17)
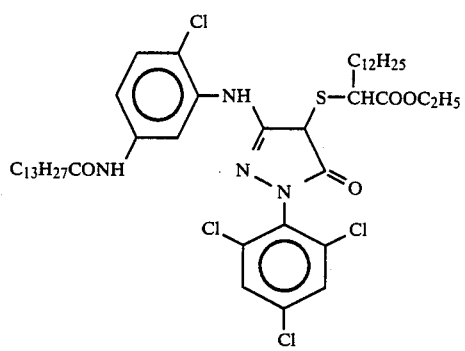 (M-18)
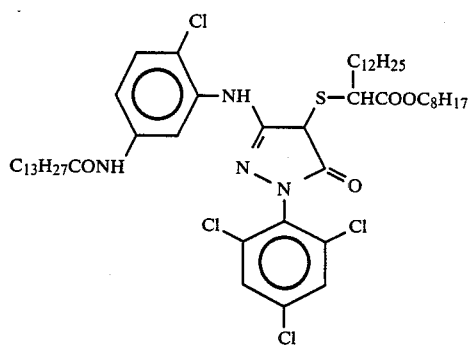 (M-19)
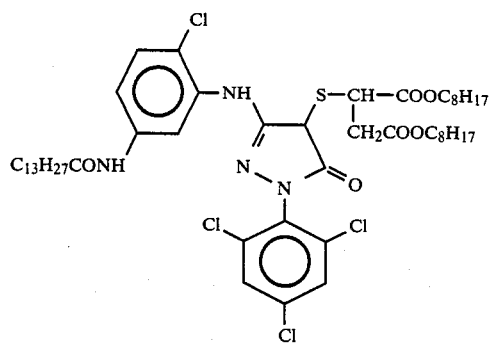 (M-20)

(M-21)
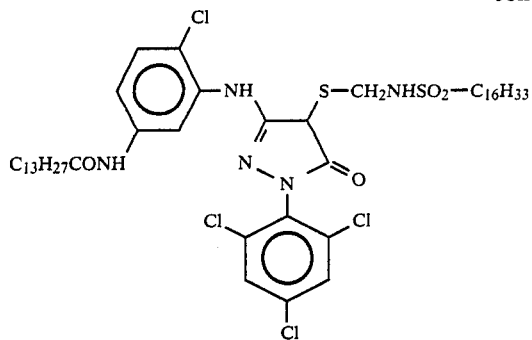
(M-22)
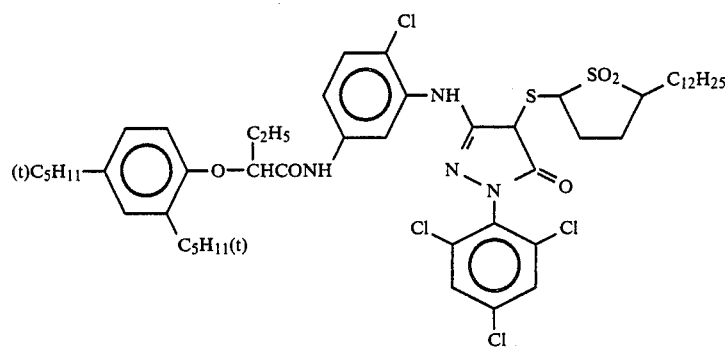
(M-23)
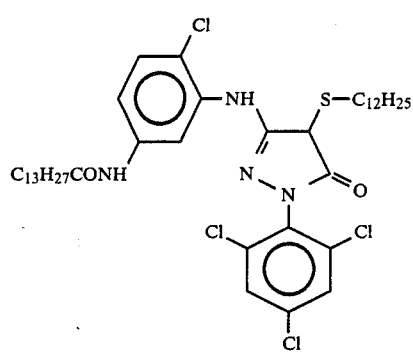
(M-24)
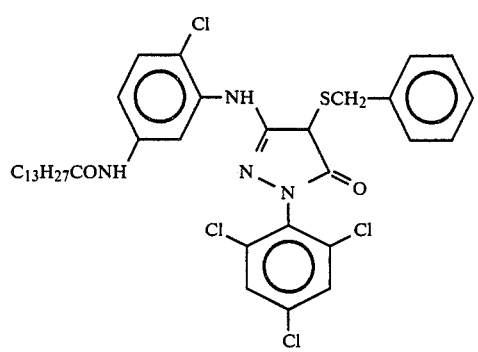
According to another embodiment of this invention, the compound represented by formula (X) above is contained in the silver halide photosensitive material for color photography containing at least one kind of pyrazolone type magenta couplers represented by formula (IX) below.
Formula (IX)
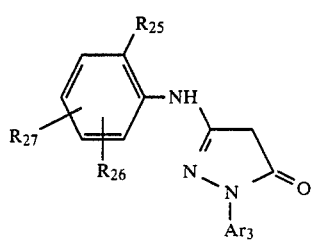

wherein $Ar_3$ has the same meaning as $Ar_1$ in formula (III) above; $R_{25}$ has the same meaning as $R_6$ in formula (IV) above; and $R_{26}$ and $R_{27}$ have the same meaning as $R_7$ in formula (IV) above. The substituent groups in $Ar_3$, $R_{25}$, $R_{26}$, and $R_{27}$ and the preferred or more preferred example of $Ar_3$, $R_{25}$, $R_{26}$, and $R_{27}$ are the same as those enumerated for $Ar_2$, $R_6$, and $R_7$ in formula (IV). The compound represented by formula (IX) is used in the same amount as the compound represented by formula (III).

The following are examples of the pyrazolone type magenta coupler represented by formula (IX).

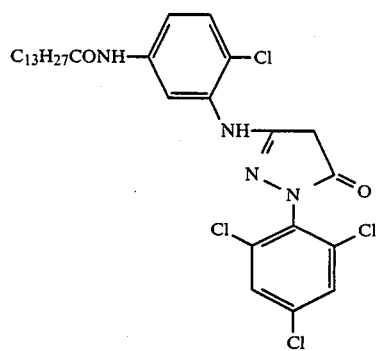 (M-25)

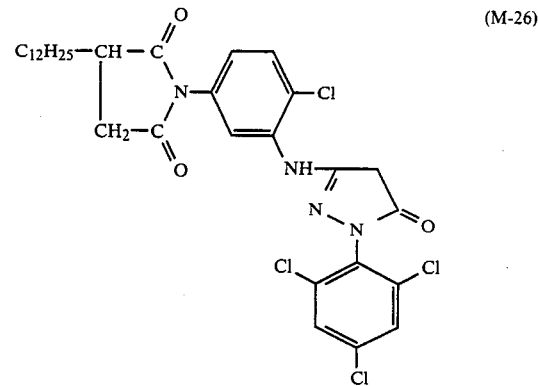 (M-26)

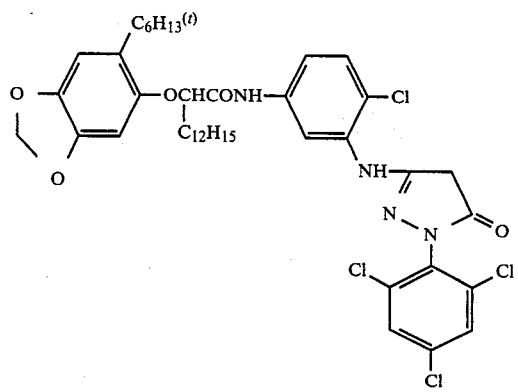 (M-27)

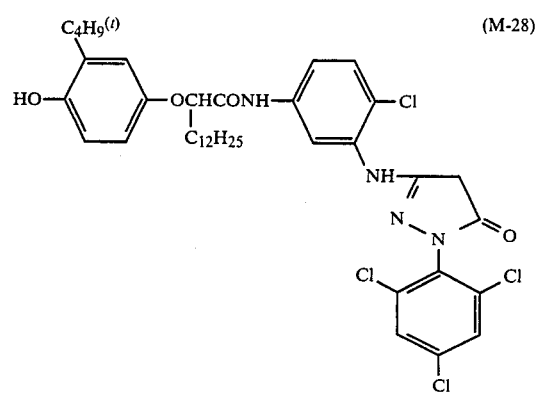 (M-28)

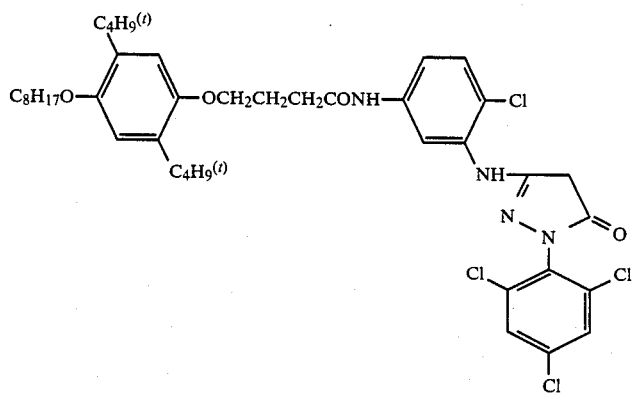 (M-29)

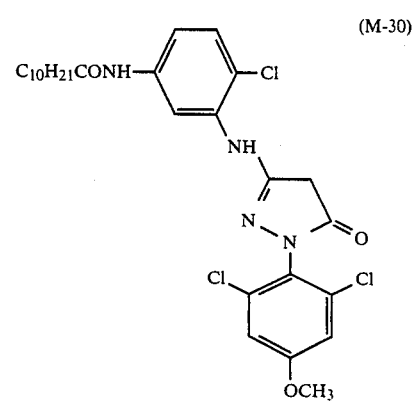 (M-30)

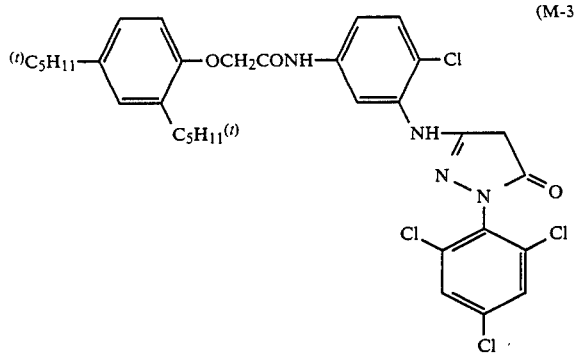
(M-31)

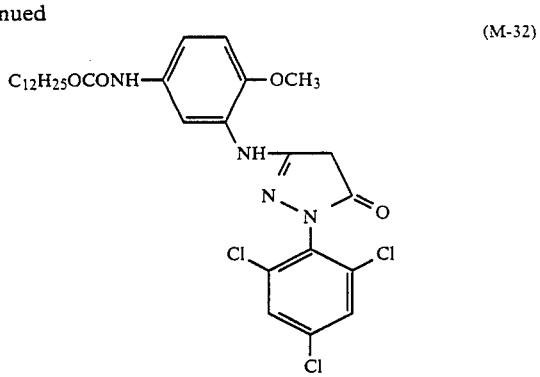
(M-32)

According to the present invention, the compound represented by formula (I) is added in an amount of 10 to 200 mol%, preferably 30 to 150 mol% based on the magenta coupler represented by formula (II) or (IX).

The compound represented by formula (I) should preferably be coemulsified with the magenta coupler.

In the following the compound represented by formula (I) is described in detail.

$R_1$ and $R_2$ in formula (I) include a hydrogen atom, alkyl group (preferably linear or branched alkyl group, aralkyl group, alkenyl group, cycloalkyl group, and cycloalkenyl group having 20 or less carbon atoms, e.g., methyl group, n-butyl group, t-butyl group, n-octyl group, n-dodecyl group, n-hexadecyl group, benzyl group, allyl group, cyclopentyl group, and cyclohexenyl group), heterocyclic group (e.g., tetrahydropyranyl group), trialkylsilyl group (e.g., trimethylsilyl group and dimethyl-t-butylsilyl group), alkanesulfonyl group (preferably alkanesulfonyl group having 20 or less carbon atoms, e.g., methanesulfonyl group, propanesulfonyl group, t-octanesulfonyl group, and octadecanesulfonyl group), arylsulfonyl group (preferably arylsulfonyl group having 20 or less carbon atoms, e.g., benzensulfonyl group, α-naphthalenesulfonyl group, and p-methoxybenzenefulfonyl group) or —X—Y.

In more detail, Y in —X—Y is an alkyl group (preferably linear or branched alkyl group, aralkyl group, alkenyl group, cycloalkyl group, and cycloalkenyl group having 20 or less carbon atoms, e.g., methyl group, n-butyl group, t-octyl group, n-dodecyl group, n-hexadecyl group, benzyl group, allyl group, cyclopentyl group, and cyclohexenyl group), aryl group (preferably aryl group having 20 or less carbon atoms, e.g., phenyl group, m-mitrophenyl group, o-chlorophenyl group, and α-naphthyl group), alkoxyl group (preferably alkoxyl group having 20 or less carbon atoms, e.g., methoxy group, t-butoxy group, cyclohexyloxy group, n-dodecyloxy group, and n-octadecyloxy group), aryloxy group (preferably aryloxy group having 20 or less carbon atoms, e.g., phenoxy group, 2,4,6-trichlorophenoxy group, p-methoxyphenoxy group, o-chlorophenoxy group, β-naphthyloxy group, and α-naphthyloxy group), alkylamino group (preferably alkylamino group having 20 or less carbon atoms, e.g., methylamino group, ethylamino group, and n-octadecylamino group), dialkylamino group (preferably dialkylamino group having 30 or less carbon atoms, e.g., diethylamino group and dioctylamino group), arylamino group (preferably arylamino group having 20 or less carbon atoms, e.g., phenylamino group, p-nitrophenylamino group, p-methylphenylamino group, and α-naphthylamino group). diarylamino group (preferably diarylamino group having 30 or less carbon atoms, e.g., N.N-diphenylamino group), alkyloycarbonyl group (preferably alkyloxycarbonyl group having 20 or less carbon atoms, e.g., methoxy carbonyl group, t-butoxycarbonyl group, cyclohexyloxycarbonyl group, and n-octyloxycarbonyl group), aryloxycarbonyl group (preferably aryloxycarbonyl group having 20 or less carbon atoms, e.g., phenoxycarbonyl group, p-methoxyphenyloxycarbonyl group, m-nitrophenoxycarbonyl group, and o-chlorophenoxycarbonyl group), and acyl group (preferably acyl group having 20 or less carbon atoms, e.g., acetyl group, butyryl group, valeryl group, pivaloyl group, and myristoyl group). $R_1$ and $R_2$ are preferably hydrogen atoms or alkyl groups.

In more detail $R_3$, $R_4$, and $R_5$ each includes hydrogen atom, alkyl group (preferably linear or branched alkyl group, aralkyl group, alkenyl group, cycloalkyl group, and cycloalkenyl group having 20 or less carbon atoms, e.g., methyl group, ethyl group, isopropyl group, t-butyl group, t-octyl group, t-hexadecyl group, benzyl group, allyl group, cyclopentyl group, and cyclohexenyl group), aryl group (preferably aryl group having 20 or less carbon atoms, e.g., phenyl group, p-methylphenyl group, p-methoxyphenyl group, p-octanamidophenyl group, o-chlorophenyl group, and α-naphthyl group), alkoxyl group (preferably alkoxyl group having 20 or less carbon aroms, e.g., methoxy group, t-butoxy group, cyclohexyloxy group, n-dodecyloxy group, n-octadecyloxy group, benzyloxy group, and allyloxy group), aryloxy group (preferably aryloxy group having 20 or less carbon atoms, e.g., phenoxy group, p-methylphenoxy group, p-methoxyphenox group, p-caproamidophenoxy group, o-chlorophenoxy group, m-nitrophenoxy group, and α-naphthyloxy group), alkylthio group (preferably alkylthio group having 20 or less carbon atoms, e.g., methylthio group, t-butylthio group, n-hexylthio group, cyclohexylthio group, and n-octadecylthio group), arylthio group (preferably arylthio group having 20 or less carbon atoms, e.g., phenylthio group, p-methylphenylthio group, o-carboxyphenylthio group, o-methylphenylthio group, o-menthoxycarbonylphenylthio group and m-nitrophenylthio group), acylamino group (preferably acylamino group having 20 or less carbon aroms, e.g., acetylamino group, benzoylamino group, and caproamino group), diacylamino group (preferably diacylamino group having 30 or less carbon atoms, e.g., succinimido group and 3-hydantoinyl group), sulfonamido group (preferably sulfonamido group having 20 or less carbon atoms, e.g., methanesulfonamido group and benzenesulfonamido group), alkylamino group (preferably alkylamino group having 30 or less carbon atoms, e.g., ethylamino group t-butylamino group, dioctylamino group, and n-octadecylamino group), acyl group (preferably acyl group having 20 or less carbon atoms, e.g., acetyl group, capryl group, and p-methoxybenzoyl group), alkyloxycarbonyl group (preferably alkyloxycarbonyl group having 20 or less carbon atoms, e.g., methoxy carbonyl group, t-butoxycarbonyl group, and n-octadecyloxycarbonyl group), acyloxy group (preferably acyloxy group having 20 or less carbon atoms, e.g., acetoxy group, caproxy group, lauroxy group, and benzoyloxy group), and halogen atom (e.g., chlorine atom and bromine atom).

Among the groups defined above, those groups which have an alkyl group or aryl group may further have a substituent group such as alkyl group, cycloalkyl group, alkenyl group, aryl group, benzyl group, halogen atom, nitro group, cyano group, hydroxyl group, alkyloxy group, cycloalkyloxy group, alkenyloxy group, aryloxy group, benzyloxy group, alkylthio group, arylthio group, amino group, alkylamino group, acylamino group, sulfonamido group, alkoxycarbonyl group, silyl group, acyl group, acyloxy group, sulfamoyl group, and sulfonyl group, some of which have been described in the definition of formula (I) above.

The following are the typical examples of the compounds represented by formula (I). They are illustrative only, and should not be construed as restricting the scope of the invention.

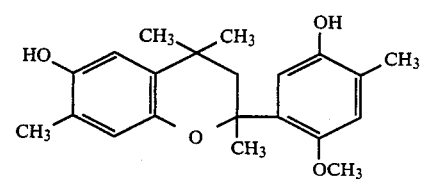
(A-1)

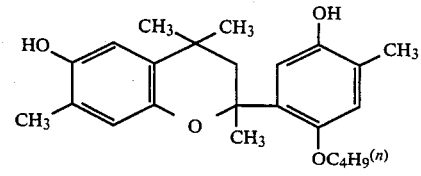
(A-2)

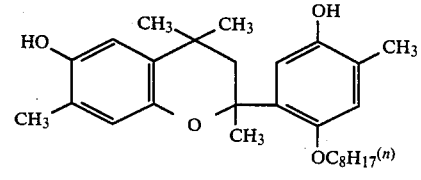
(A-3)

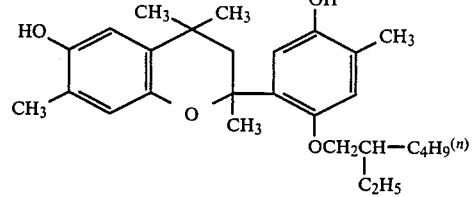
(A-4)

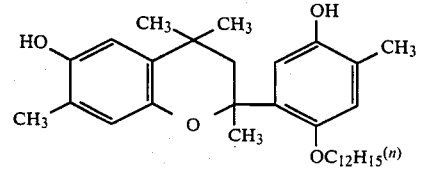
(A-5)

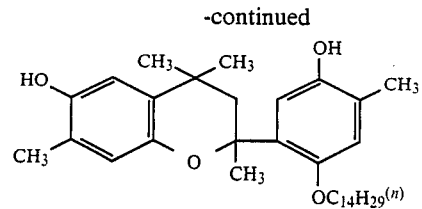
(A-6)

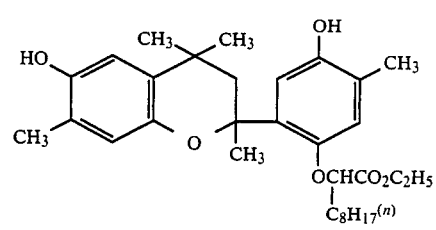
(A-7)

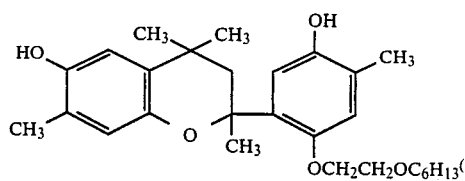
(A-8)

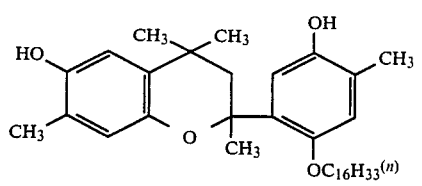
(A-9)

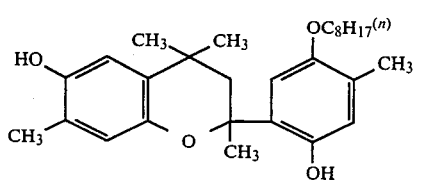
(A-10)

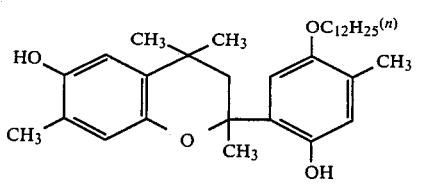
(A-11)

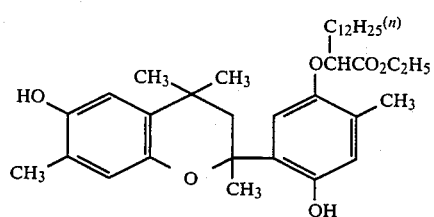
(A-12)

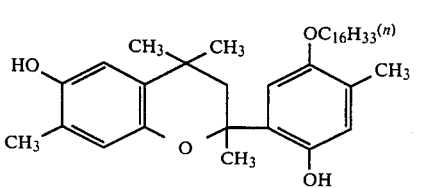
(A-13)

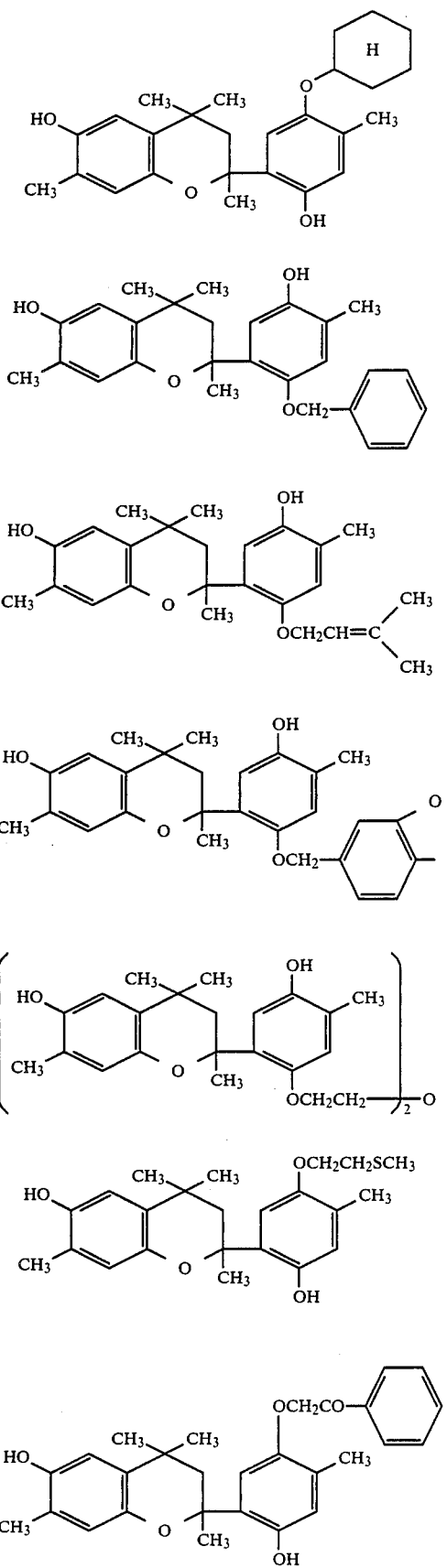
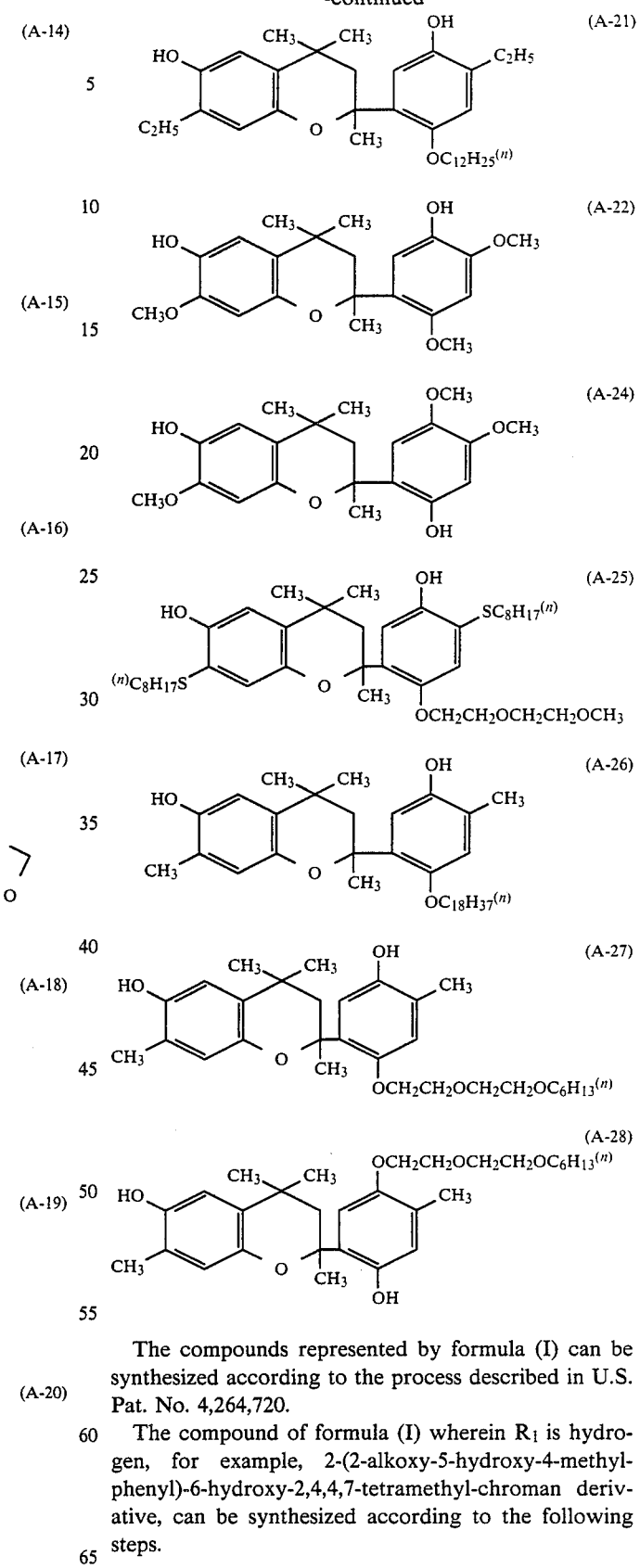
The compounds represented by formula (I) can be synthesized according to the process described in U.S. Pat. No. 4,264,720.
The compound of formula (I) wherein $R_1$ is hydrogen, for example, 2-(2-alkoxy-5-hydroxy-4-methylphenyl)-6-hydroxy-2,4,4,7-tetramethyl-chroman derivative, can be synthesized according to the following steps.

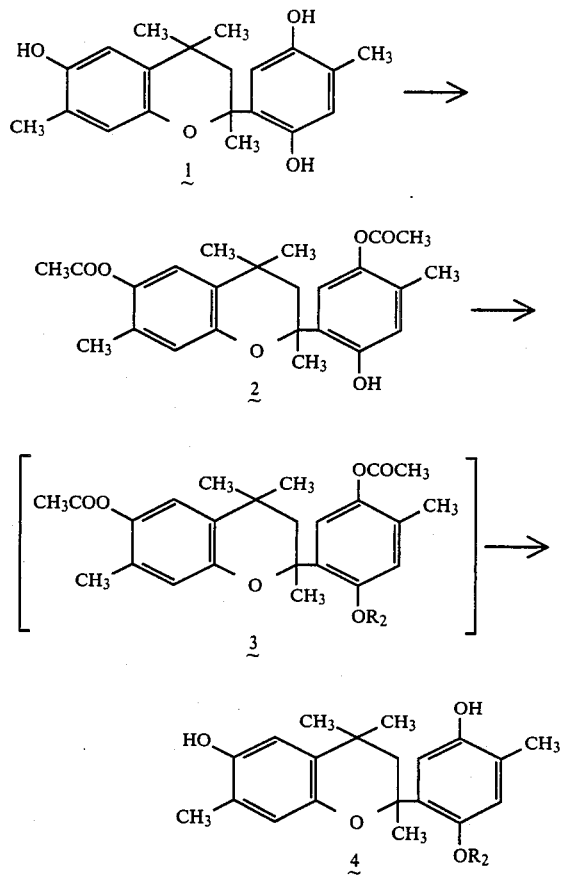

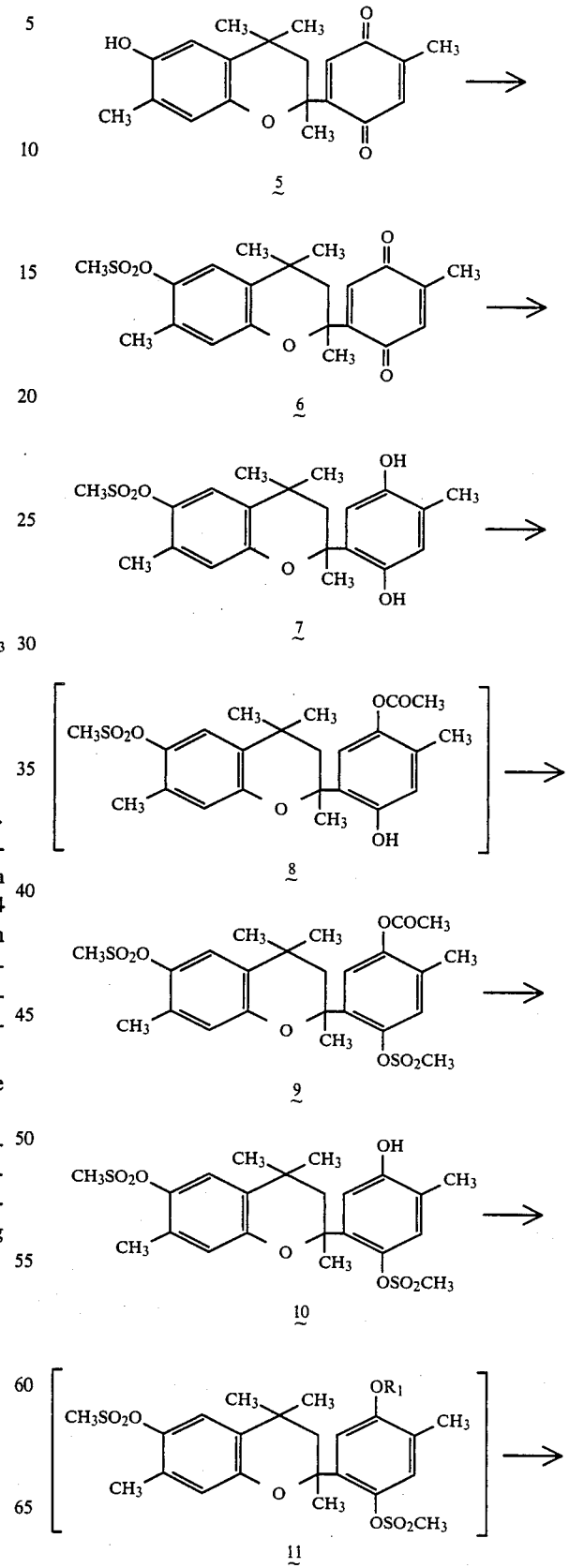

Wherein $R_2$ has the same meaning as defined above.

As is shown in synthesis scheme (1) at first, compound 1 is converted into compound 2, which is then reacted with an alkylating agent to give compound 4 having a varied aliphatic group represented by $R_2$. In the synthesis process, compound 3 formed may be isolated before the reaction to form compound 4. Alternatively, the reaction may be carried out in the same vessel without isolating compound 3.

Compound 1 can be synthesized according to the process described in U.S. Pat. No. 4,113,495.

The compound of formula (I) wherein $R_2$ is hydrogen, for example, 2-(5-alkoxy-2-hydroxy-4-methylphenyl)-6-hydroxy-2,4,4,7-tetramethyl-chroman derivative, can be synthesized according to the following steps.

Synthesis Scheme (2)

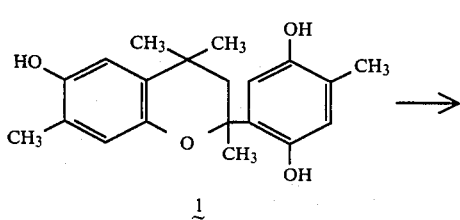

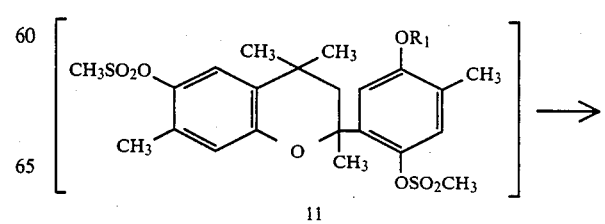

-continued
Synthesis Scheme (2)

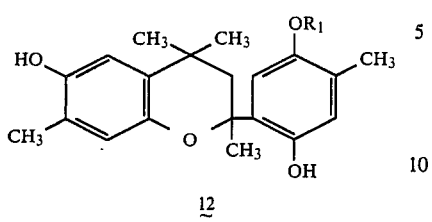

Wherein R₁ has the same meaning as above.

As is shown in synthesis scheme (2), compound 10 produced from compound 1 through several steps is reacted with an alkylating agent to give compound 12 having a varied aliphatic group represented by $R_1$.

In the synthesis scheme (2), compounds 8 and 11 may be isolated before the subsequent reactions (8→9 or 11→12). Alternatively, the reaction may be carried out in the same vessel without isolating compounds 8 and 11.

The compound represented by formula (I) should be added in an amount of 10 to 200 mol%, preferably 30 to 150 mol% based on the magenta coupler of this invention. This compound should preferably be coemulsified with the magenta coupler.

The compound represented by formula (I) in this invention may be used in a composition as the active ingredient with a diluent, solvent, carrier, and the like in a proper ratio. It may also include the chroman dorivative alone.

The compounds represented by formula (I) in this invention may be used individually or in combination with one another. It may also be used in combination with a known discoloration inhibitor, which includes, for example, hydroquinones, 6-hydroxychromans, 5-hydroxycoumarans, spiro-coumarans, spiro-indanes, p-alkoxyphenols, bisphenoles, and other hindered phenoles; gallic acid derivatives, methylenedioxybenzenes, aminophenols, hindered amines, and those compounds obtained by silylating, acylating, or alkylating the phenolic hydroxyl group of said compounds; and metal complexes.

Preferred examples of the known discoloration inhibitors are disclosed in U.S. Pat. Nos. 3,336,135, 3,432,300, 3,573,050, 3,574,627, 3,700,455, 3,764,337, 3,935,016, 3,9872,944, 4,254,216, and 4,279,990; British Pat. Nos. 1,347,556, 2,062,888, 2,066,975, and 2,077,455; Japanese Patent Application No. 205278/1983, Japanese Patent Application (OPI) Nos. 152225/1977, 17729/1978, 20327/1978, 145530/1979, 6321/1980, 21004/1980, 24141/1983, and 10539/1984; and Japanese Patnet Publication Nos. 31625/1973 and 12337/1979. It is preferable to use the compound represented by formula (I) in combination with hydroquinones, 6-hydroxychromans, p-alkoxyphenols, alkoxy-substituted spiro-indanes, methylenedioxybenzenes, or bisphenols.

The following are the typical examples of the known discoloration inhibitor preferred in this invention.

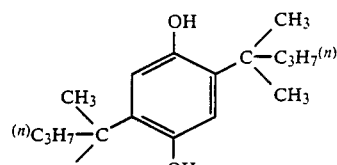

G-1

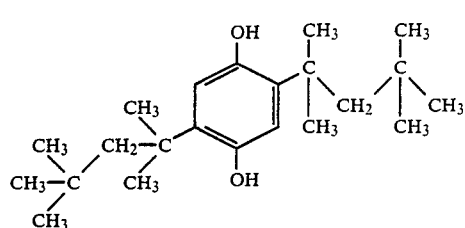

G-2

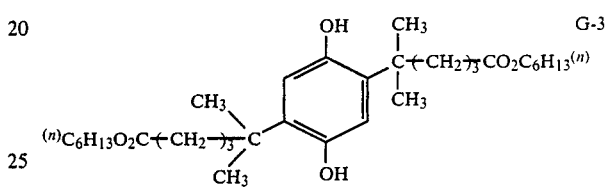

G-3

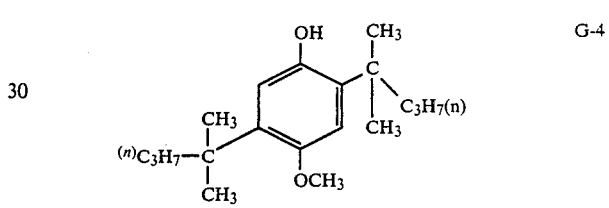

G-4

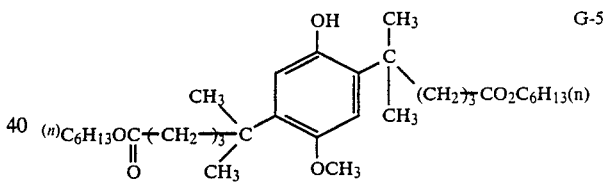

G-5

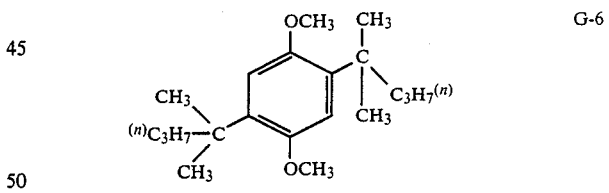

G-6

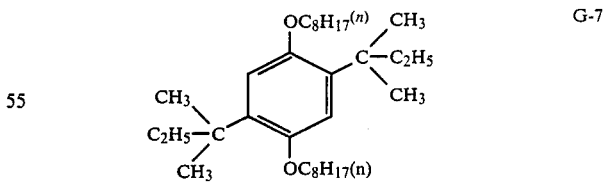

G-7

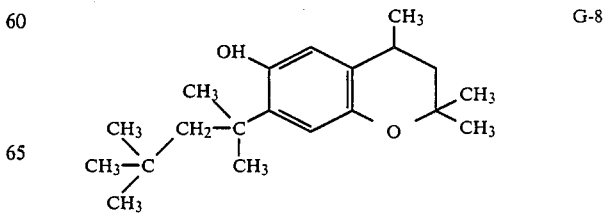

G-8

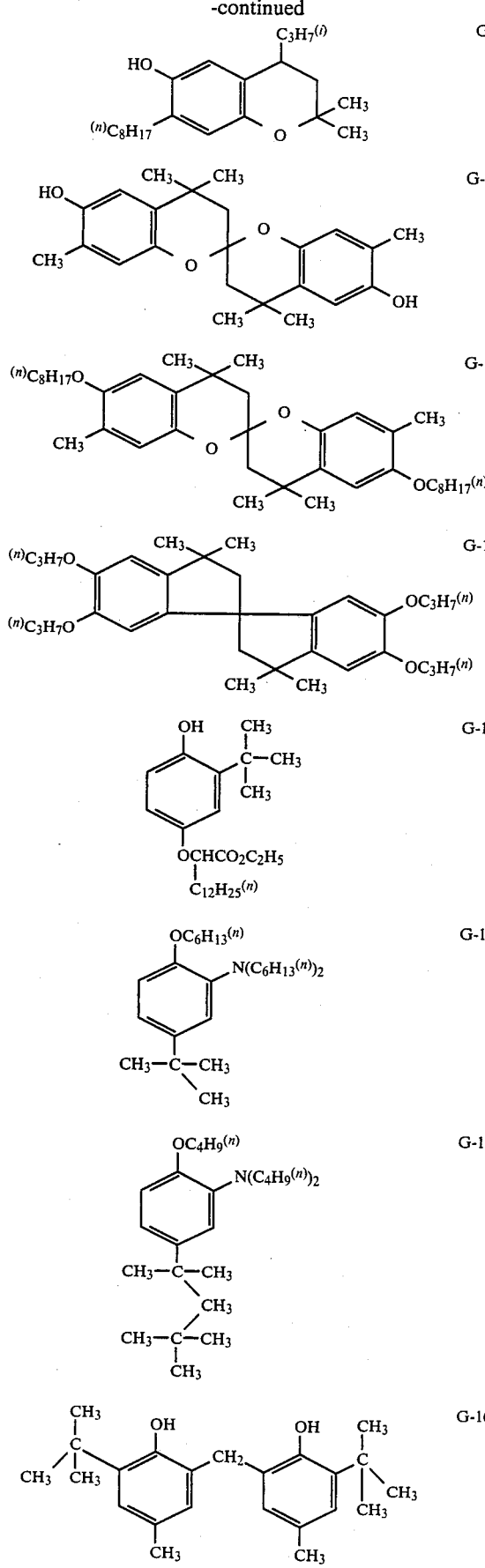

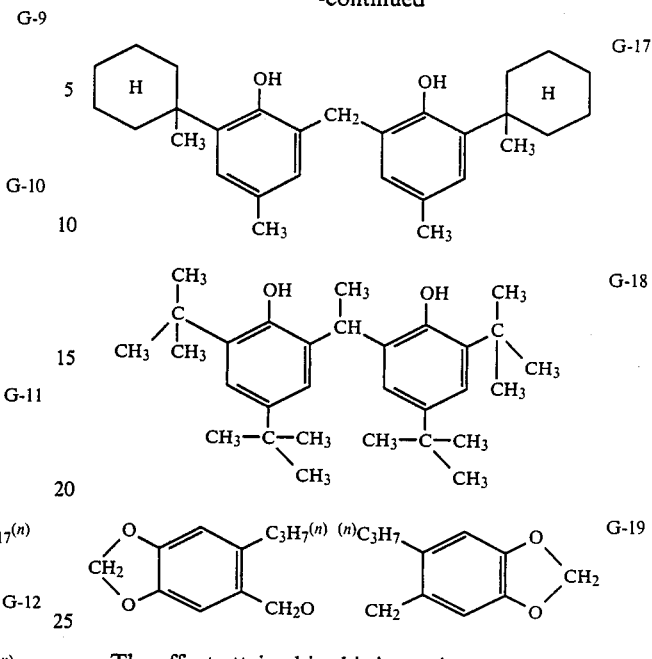

The effect attained in this invention can be enhanced when an ultraviolet-light absorbent is employed. Preferred examples of ultraviolet-light adsorbents are benzotriazole compounds with an aryl substituent (as disclosed in U.S. Pat. No. 3,533,794), 4-thiazolidone compounds (as disclosed in U.S. Pat. Nos. 3,314,794 and 3,352,681), benzophenone compounds (as disclosed in Japanese Patent Application (OPI) NO. 2784/1971), cinnamic ester compounds (as disclosed in U.S. Pat. Nos. 3,705,805 and 3,707,375), butadiene compounds (as disclosed in U.S. Pat. No. 4,045,229), benzoxydole compounds (as disclosed in U.S. Pat. No. 3,700,455) and other compounds (as disclosed in U.S. Pat. No. 3,499,762 and Japanese Patent Application (OPI) No. 48535/1979). Further a coupler having ultraviolet-light absorbency (e.g., cyan-dyeforming coupler of α-naphthol series) or a polymer having ultraviolet-light absorbency. The ultraviolet-light absorbent may be mordanted in a specific layer of the color photographic material.

The ultraviolet-light absorbent may be added optionally to any layer in the color photographic material. For example, it may be added to an interlayer placed above (distant side from the support) the magenta image-forming layer or protective layer or both. It may be added to a cyan image-forming layer or an adjacent layer thereof.

The compound represented by formula (I) of this invention attains a much enhanced effect in the prevention of discoloration when an ultraviolet-light absorbent represented by formula (XI) below is added to at least one layer of protective layers, being divided into two.

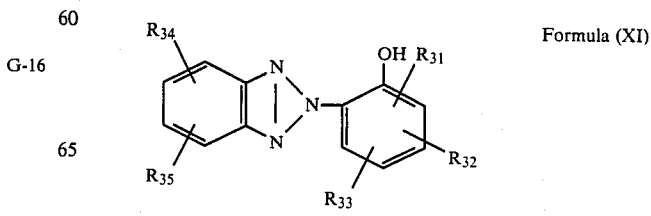

Formula (XI)

wherein $R_{31}$, $R_{32}$, $R_{33}$, $R_{34}$, and $R_{35}$, which may be the same or different, each represents a hydrogen atom, halogen atom, nitro group, hydroxyl group, alkyl group, alkenyl group, aryl group, alkoxyl group, acyloxy group, aryloxy group, alkylthio group, arylthio group, mono- or dialkylamino group, acylamino group, or 5- or 6-membered heterocyclic group containing at least oxygen or nitrogen. $R_{34}$ and $R_{35}$ may form through ring closure a 5- or 6-membered aromatic ring composed of carbon atoms. These groups may have substituent groups thereon if they have an atom or group capable of being substrituted.

The following are typical examples of the ultraviolet-light absorbents represented by the formula (XI). They are illustrative only and should not be construed as restricting the scope of the invention.

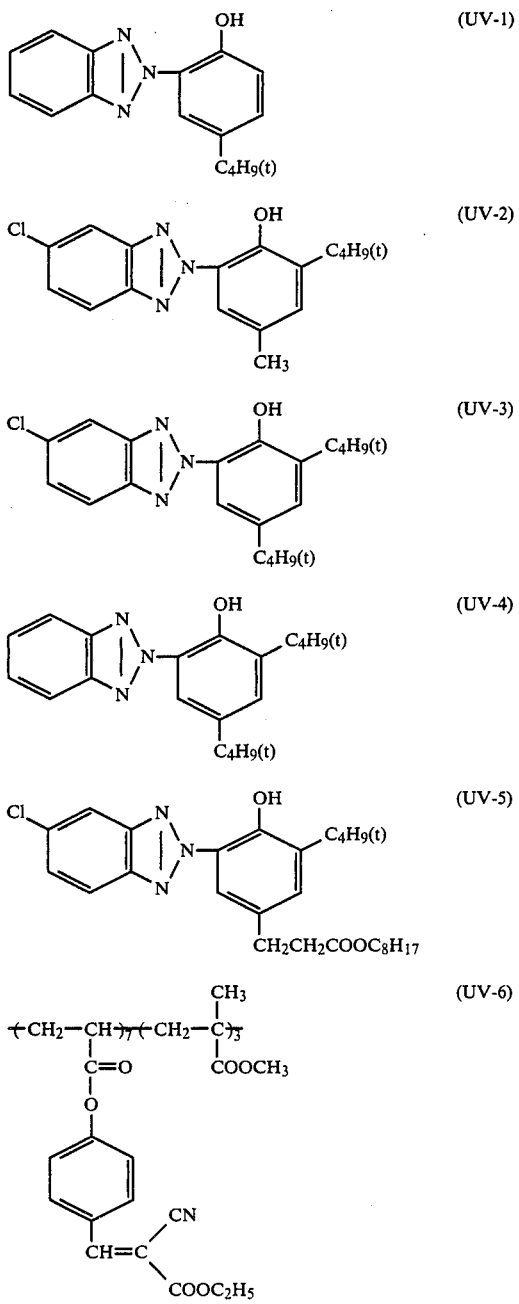

The compounds represented by formula (XI) above may be synthesized according to the processes as disclosed in Japanese Patent Application (OPI) Nos. 29620/1969, 151149/1975, and 95233/1979; U.S. Pat. No. 3,766,205; EP No. 0057160; and Research Disclosure 22519 (1983, No. 225). It is also possible to use polymeric UV absorbents as disclosed in Japanese Patent Application (OPI) Nos. 111942/1983, Japanese Patent Application Nos. 61937/1982, 63602/1982, 129780/1982, and 133371/1982. An example thereof is indicated by UV-6. A low-molecule UV absorbent and a high-molecule UV absorbent may be used together.

Usually the ultraviolet-light absorbent may be used in an amount of $1 \times 10^{-4}$ to $2 \times 10^{-3}$ mol/m$^2$, and preferably $5 \times 10^{-4}$ to $1.5 \times 10^{-3}$ mol/m$^2$. An excess amount of UV absorbent in some cases might cause in the unexposed part (white background) of the color photographic material yellowing.

It will be preferable to apply the technical idea of enclosing the dye image with oxygen barrier layers made of a substance having a low oxygen permeability (as disclosed in Japanese Patent Application (OPI) Nos. 11330/1974 and 57223/1975) and the technical idea of providing a layer having an oxygen permeability of 20 ml/m$^2$.hr.atm or less under the color image forming layer (as disclosed in Japanese Patent Application (OPI) No. 85747/1981.)

In this invention, a variety of color couplers can be used. By "color coupler" is meant a compound that forms a dye upon coupling reaction with an oxidation product of an aromatic primary amine developing agent. Useful color couplers are ones which form cyan, magenta, and yellow. Their typical examples include naphthol or phenol compounds, pyrazolone or pyrazoloazole compounds, and open-chain or heterocyclic ketomethylene compounds, respectively. Examples of the cyan, magenta, and yellow couplers that can be used in this invention are disclosed in the patents cited in Research Disclosure (RD) 17643 (December 1978). Paragraph VIII-D, and 18717 (November 1979).

The magenta coupler that can be used in this invention includes oil-protected couplers of indazolone or cyanoacetyl type, preferably of pyrazoloazole (e.g., pyrazotriazole) type. 5-pyrazolones substituted by an acyamino group at the 3-position are preferable in view of the hue and maximum densities of formed dyes and are disclosed in U.S. Pat. Nos. 2,311,082, 2,343,703, 2,600,788, 2,908,573, 3,062,653, 3,152,896, and 3,936,015. Two-equivalent 5-pyrazolone couplers having as the coupling-off group a nitrogen-linked coupling-off group (as disclosed in U.S. Pat. No. 4,310,619) or an arylthio group (as disclosed in U.S. Pat. No. 4,351,897) are preferable. A high image density can be obtained with a 5-pyrazolone coupler having the ballast group as disclosed in European Pat. No. 73,636.

Examples of pyrazoloazole couplers include pyrazolobenzimidazoles (as disclosed in U.S. Pat. No. 3,369,879), preferably pyrazole[5,1,-c][1,2,4]triazoles (as disclosed in U.S. Pat. No. 3,725,067), pyrazolotetrazoles (as disclosed in Research Disclosure 24220 (June 1984), and Pyrazolopyrazoles (as disclosed in Research Disclosure 24230 (June 1984). Imidazo[1,2,-b]pyrazoles and pyrazole-(1,5,-b)-(1,2,4)-triazole disclosed in European Pat. Nos. 119,741 and 119,860, respectively are preferable since the formed dye has reduced yellow sideabsorption and superior fastness to light.

The cyan coupler that can be used in this invention includes naphthol couplers and phenol couplers of oil-protected type. An example of naphthol coupler is that disclosed in U.S. Pat. No. 2,474,293 and preferred examples of naphthol couplers are such two-equivalent naphthol couplers as oxygen atom splitting-off type disclosed in U.S. Pat. Nos. 4,052,212, 4,146,396, 4,228,233, and 4,296,200. Examples of the phenol couplers are those disclosed in U.S. Pat. Nos. 2,369,929, 2,801,171, 2,772,162, and 2,895,826.

Examples of cyan couplers stable to moisture and heat and advantageously used in this invention include phenol cyan couplers having a higher alkyl group than methyl group at meta position of the phenol nucleus disclosed in U.S. Pat. No. 3,772,002 and phenol cyan couplers having a phenylureido group at 2-position and an acylamino group at 5-position disclosed in U.S. Pat. Nos. 3,446,622, 4,333,999, 4,451,559, and 4,427,767.

The effect of this invention will be advantageously achieved when at least one of the compounds represented by formula (XII) or (XIII) below is used as a cyan coupler. The compounds represented by formulas (XII) and (XIII) may be used together.

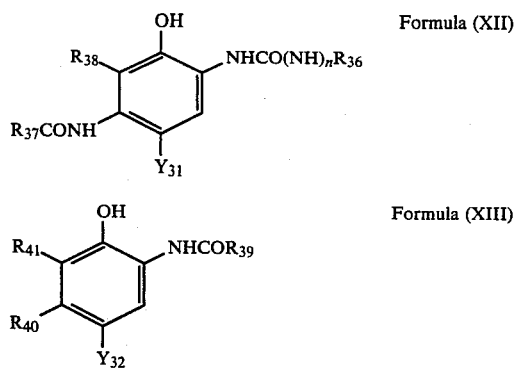

Formula (XII)

Formula (XIII)

wherein $R_{36}$, $R_{37}$, and $R_{39}$ represent substituted or unsubstituted aliphatic, aromatic, or heterocyclic groups; $R_{38}$ and $R_{41}$ represent hydrogen atoms, halogen atoms, aliphatic groups, aromatic groups, or acylamino groups; $R_{38}$ represents a group of nonmetallic atoms which forms, together with $R_{37}$, a nitrogen-containing 5- or 6-membered ring; $R_{40}$ represents an aliphatic group having at least 2 carbon atoms which may be further substituted; $Y_{31}$ and $Y_{32}$ represent hydrogen atoms or the groups that can be splitted-off upon oxidation coupling reaction with the developing agent; and n is 0 or 1. A dimeric or polymeric coupler may be formed through one of the groups $R_{37}$, $R_{38}$, and $Y_{31}$, or one of the groups $R_{40}$, $R_{41}$, and $Y_{32}$.

The term "aliphatic group" in this specification and claims means linear, branched, and cyclic aliphatic groups and also saturated and unsaturated aliphatic groups such as alkyl, alkenyl, and aralkyl groups.

The following is a detailed description of the cyan coupler represented by formula (XII) or (XIII).

$R_{36}$, $R_{37}$, and $R_{39}$ include, for example, a methyl group, butyl group, tridecyl group, cyclohexyl group, and allyl group, as aliphatic groups having 1 to 32 carbon atoms; phenyl a group and naphthyl group as aryl groups; and a 2-pyridyl group, 2-imidazolyl group, 2-furyl group, and 6-quinolyl group as heterocyclic groups. These groups may be further subsituted with a group selected from alkyl groups, aryl groups, heterocyclic groups, alkoxyl groups (e.g., methoxy group and 2-methoxyethoxy group), aryloxy groups (e.g., 2,4-ditert-amylphenoxy group, 2-chlorophenoxy group, and 4-cyanophenoxy group), alkenyloxy groups (e.g., 2-propenyloxy group), acyl groups (e.g., acetyl group and benzoyl group), ester groups (e.g., butoxycarbonyl group, phenoxycarbonyl group, acetoxy group, benzoyloxy group, butoxysulfonyl group, and toluenesulfonyloxy group), amido groups (e.g., acetylamino group, methanesulfonamide group, and dispropylsulfamoylamido group), carbamoyl groups (e.g., diemthylcarbamoyl group and ethylcarbamoyl group), sulfamoyl groups (e.g., butylsulfamoyl group), imido groups (e.g., succinimido group and hydantoinyl group), ureido groups (e.g., phenylureido group and dimethylureido group), aliphatic or aromatic sulfonyl groups (e.g., methanesulfonyl group and phenylsulfonyl group), aliphatic or aromatic thio groups (e.g., ethylthio group and phenylthio group), a hydroxyl group, cyano group, carboxyl group, nitro group, sulfo group, and halogn atoms.

In the case where $R_{38}$ in formula (XII) has an atom or group able to be substituted with a substituent, it may be substituted by the substituent described for $R_6$ above.

The aliphatic group represented by $R_{40}$ in formula (XIII) which has 2 or more carbon atoms and may have a substituent group thereon includes, for example, an ethyl group, propyl group, butyl group, pentadecyl group, tertbutyl group, cyclohexyl group, cyclohexylmethyl group, phenylthiomethyl group, dodecyloxyphenylthiomethyl group, butanamidomethyl group, and methoxymethyl group.

$Y_{31}$ and $Y_{32}$ in formulas (XII) and (XIII) represent hydrogen atoms or coupling splitting-off groups (including coupling splitting-off atoms [the same shall apply hereinafter]). Their examples include halogen atoms (e.g., fluorine atom, chlorine atom, and bromine atom), alkoxyl groups (e.g., ethoxy group, dodecyloxy group, methoxyethylcarbamoylmethoxy group, carboxypropyloxy group, and methylsulfonylethoxy group), aryloxy groups (e.g., 4-chlorophenoxy group, 4-methoxyphenoxy group, and 4-carboxyphenoxy group), acylozy groups (e.g., acetoxy group, tetradecanoyloxy group, and benzoyloxy group), sulfonyloxy groups (e.g., methanesulfonyloxy group and toluenesulfonyloxy group), amido groups (e.g., dichloroacetylamino group, heptafluorobutylamino group, methanesulfonylamino group, and toluenesulfonylamino group), alkoxycarbonyloxy groups (e.g., ethoxycarbonyloxy group and benzyloxycarbonyloxy group), aryloxycarbonyloxy groups (e.g., phenoxycarbonyloxy group), aliphatic or aromatic thio groups (e.g., ethylthio group, phenylthio group, and tetrazolylthio group), imido groups (e.g., succinimido group and hydantoinyl group), and aromatic azo groups (e.g., phenylazo groups). These splitting-off groups may contain a photographic useful group.

Among the cyan couplers represented by formula (XII) or (XIII) above the preferable ones are as follows:

$R_{36}$ in formula (XII) is preferably an aryl group or heterocyclic group, and more preferably an aryl group further substituted by a halogen atom, alkyl group, alkoxyl group, aryloxy group, acylamino group, acyl group, carbamoyl group, sulfonamido group, sulfamoyl group, sulfonyl group, sulfamido group, oxycarbonyl group, or cyano group.

Where $R_{37}$ and $R_{38}$ in formula (XII) do not form a ring, preferably $R_{37}$ is a substituted or unsubstituted alkyl group or aryl group, and more preferably an alkyl group substituted by a substituted arylozy group; and $R_{38}$ is preferably a hydrogen atom.

$R_{39}$ in formula (XIII) is preferably a substituted or unsubstituted alkyl group or aryl group, and more preferably an alkyl group substituted by a substituted aryloxy group.

$R_{40}$ in formula (XIII) is preferably an alkyl group having 2 to 15 carbon atoms or a methyl group having a substituent having 1 or more carbon atoms, the preferred substituent being an aryl group, alkylthio group, acylamino group, aryloxy group, and alkyloxy group.

$R_{40}$ in formula (XIII) is preferably an alkyl group having 2 to 15 carbon atoms, and more preferably an alkyl group having 2 to 4 carbon atoms.

$R_{41}$ in formula (XIII) is preferably a hydrogen atom or halogen atom, and more preferably a chlorine atom or fluorine atom.

$Y_{31}$ and $Y_{32}$ in formulas (XII) and (XIII) are preferably a hydrogen atom, halogen atom, alkoxyl group, aryloxy group, acyloxy group, or sulfonamido group.

$Y_{32}$ i formula (XII) is preferably a halogen atom, and more preferably a chlorine atom or fluorine atom.

Where n=0 in formula (XII), $Y_{31}$ is preferably a halogen atom, and more preferably a chlorine atom or fluorine atom.

The following are the examples of cyan couplers represented by formulas (XII) and (XIII) above. They are illustrative only and should not be construed as restricting the scope of this invention.

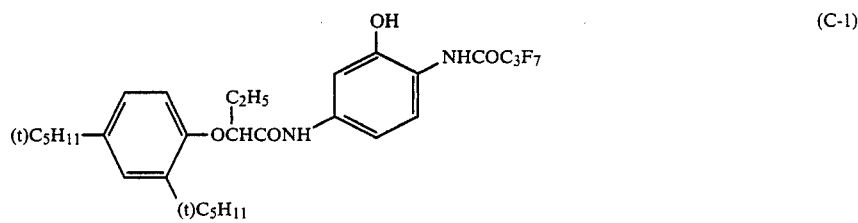
(C-1)

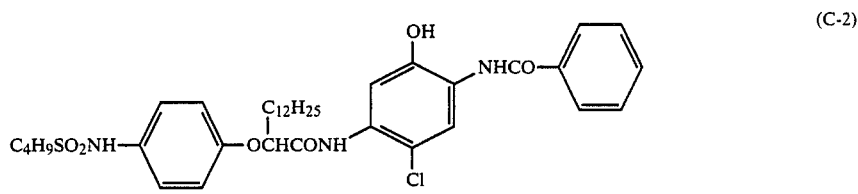
(C-2)

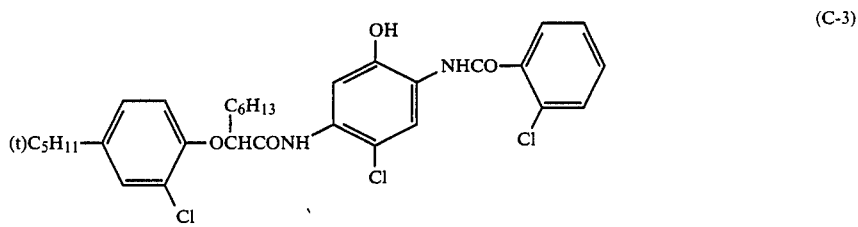
(C-3)

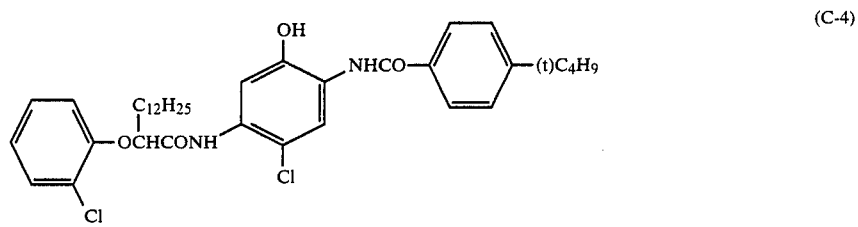
(C-4)

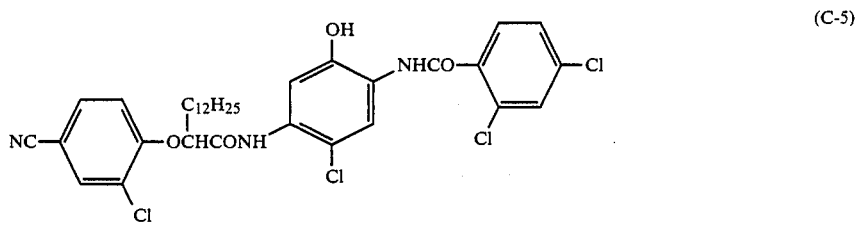
(C-5)

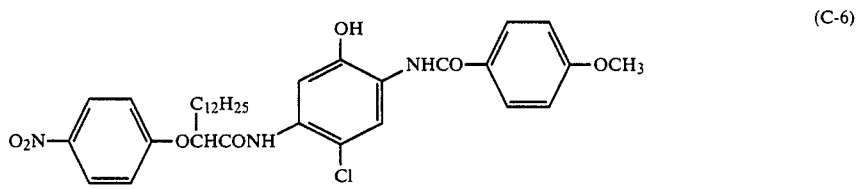
(C-6)

-continued
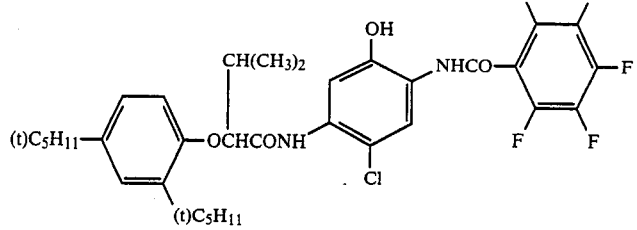
(C-7)
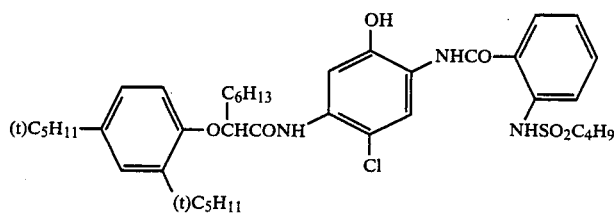
(C-8)
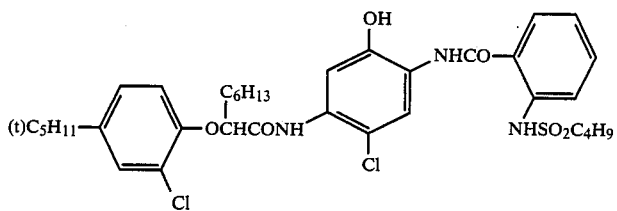
(C-9)
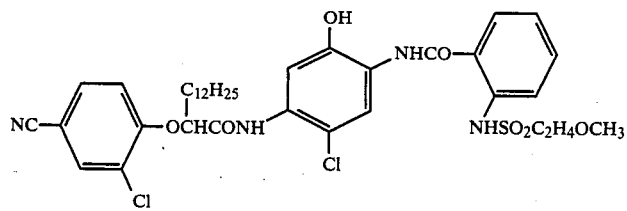
(C-10)
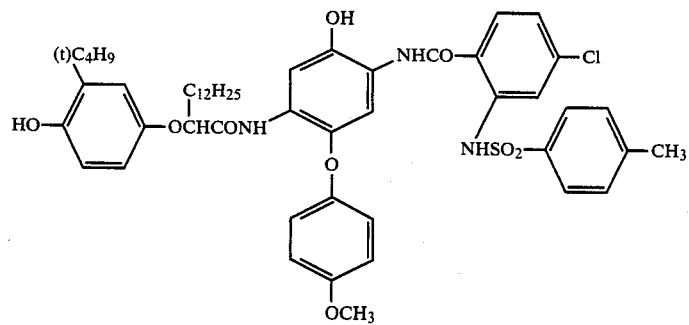
(C-11)
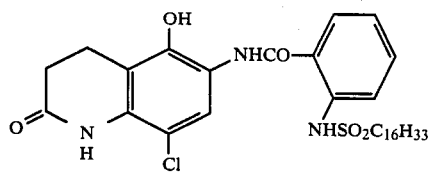
(C-12)
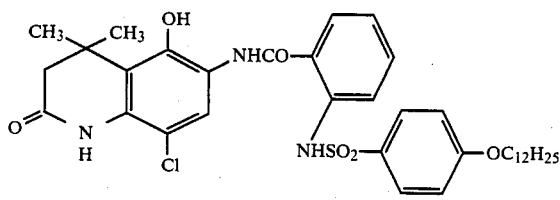
(C-13)

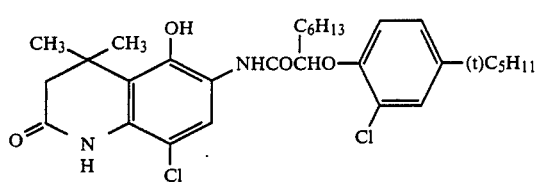
(C-14)
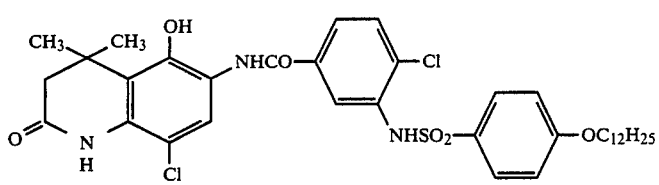
(C-15)
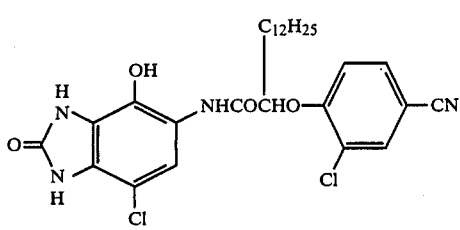
(C-16)
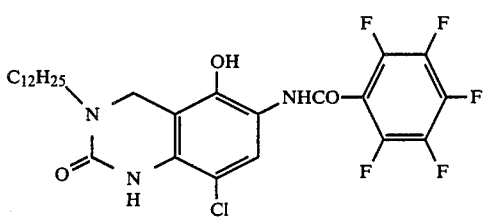
(C-17)
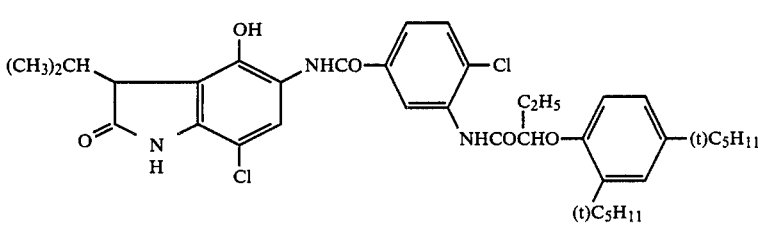
(C-18)
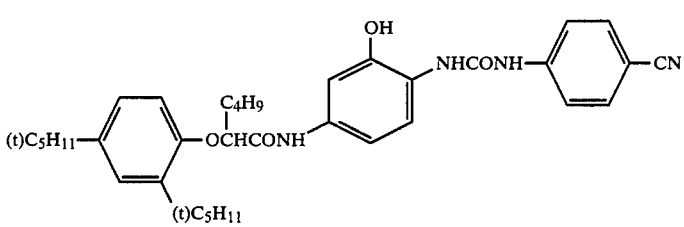
(C-19)
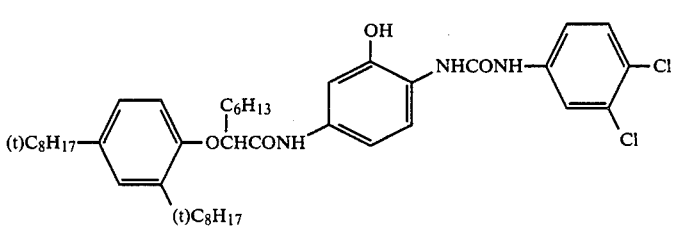
(C-20)

-continued
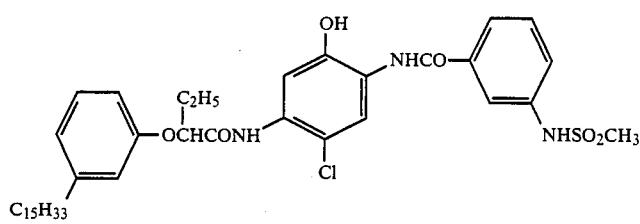
(C-21)
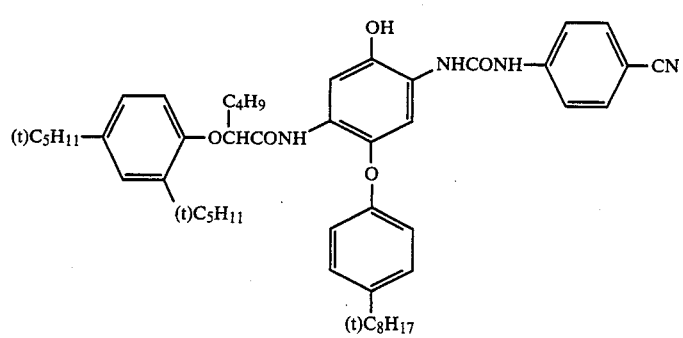
(C-22)
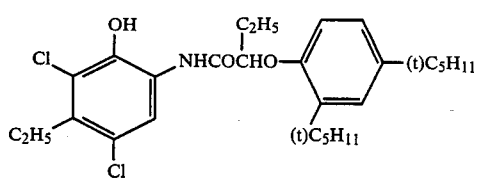
(C-23)
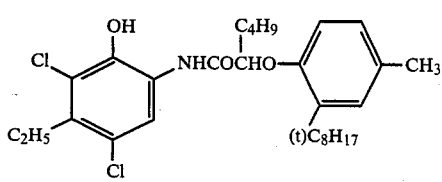
(C-24)
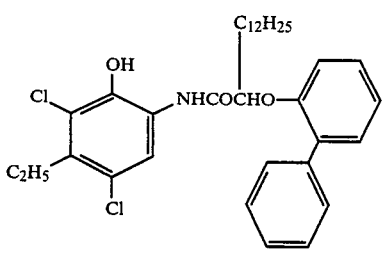
(C-25)
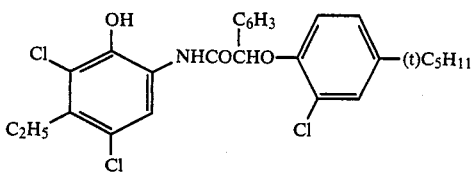
(C-26)
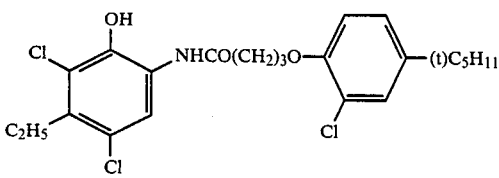
(C-27)

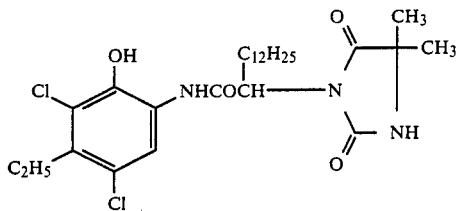
(C-28)

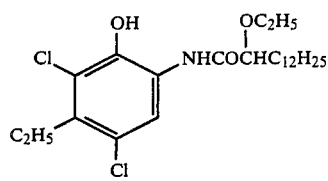
(C-29)

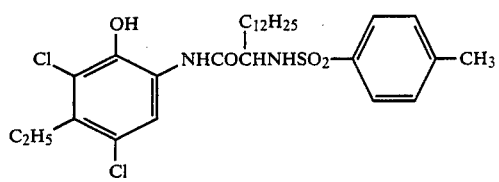
(C-30)

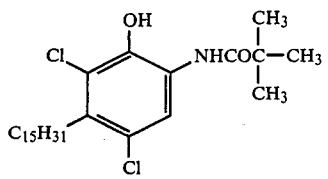
(C-31)

Among the yellow couplers that can be used in this invention, the typical examples are acylacetamide couplers of oil-protected type, which are described in U.S. Pat. Nos. 2,407,210, 2,875,057, and 3,265,506. Two-equivalent yellow couplers are preferred in this invention. Their examples are yellow couplers of oxygen-atom linkage split-off type disclosed in U.S. Pat. Nos. 3,408,194, 3,447,928, 3,933,501, and 4,022,620, and yellow couplers of nitrogen-atom linkage split-off type disclosed in Japanese Patent Publication No. 10739/1983; U.S. Pat. Nos. 4,401,752 and 4,326,024; Research Disclosure No. 18053 (April 1979); British Pat. No. 1,425,020; and West Germany Patent Application (OLS) Nos. 2,219,917, 2,261,361, 2,329,587, and 2,433,812.

α-Pivaloylacetanilide couplers from dyes which are superior in fastness especially in fastness to light, and α-benzoylacetanilide couplers provide high image density.

Preferable among the yellow couplers used in this invention are those which are represented by formula (XIV) below.

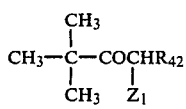
Formula (XIV)

wherein $R_{42}$ denotes a substituted or unsubstituted N-phenylcarbamoyl group; $Z_1$ denotes a hydrogen atom or a group which is splitted-off upon coupling reaction with an oxidation product of the developing agent; and a dimer or polymer may be formed through $Z_1$.

The N-phenylcarbamoyl group $R_{42}$ in formula (XIV) above may have the substituent on the phenyl group selected from the group of substituents acceptable for $R_{36}$ defined in formula (XII) above. Where there are two or more substituents, they may be the same or different.

The preferred example of $R_{42}$ is represented by formula (XV) below.

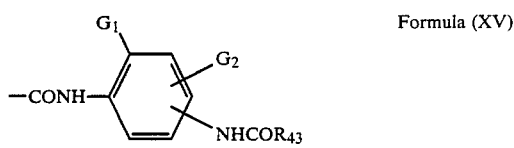
Formula (XV)

wherein $G_1$ represents a halogen atom or alkoxyl group; $G_2$ represents a hydrogen atom, halogen atom, or alkoxyl group which may has a substituent; and $R_{43}$ denotes an alkyl group which may have a substituent.

The substituents on $G_2$ and $R_{43}$ in formula (XV) are an alkyl group, alkoxyl group, aryl group, aryloxyl group, amino group, dialkylamino group, heterocyclic group, (e.g., N-morpholino group, N-piperidino group, and 2-furyl group), halogen atom, nitro group, hydroxyl group, carboxyl group, sulfo group, and alkoxycarbonyl group.

The couplers and other compounds and synthesis processes thereof illustrated in this invention are described in the following literatures. The cyan coupler compounds are described in U.S. Pat. Nos. 2,772,162 and 4,333,999; Japanese Patent Application (OPI) No. 98731/1983; and Japanese Patent Publication No. 11572/1974. The yellow coupler compounds are described in Japanese Patent Application (OPI) No. 48541/1979; Japanese Patent Publication No. 10739/1983; U.S. Pat. No. 4,326,024; and Research Disclosure No. 18053. The couplers used in the Examples (mentioned later) of this invention can be prepared according to the synthesis method described in these literatures.

The above-mentioned coupler compound used in this invention may have the ballast group described in Japanese Patent Application (OPI) No. 42045/1983 and Japanese Patent Application Nos. 88940/1983, 52923/1983, 52924/1983, and 52927/1983.

The cyan coupler used in this invention shows improved preservability of formed dye images (especially cyan images), particularly fastness to light, when used in combination with an ultraviolet-light absorbent represented by formula (XI). The cyan coupler may be coemulsified with this ultraviolet-light absorbent.

In this invention, a known discoloration inhibitor used for the magenta coupler as mentioned above may be used for the improvement of the fastness of the cyan image or yellow image.

Preferable among these known discoloration inhibitors are those which are represented by formulas (XVI) and (XVII) below.

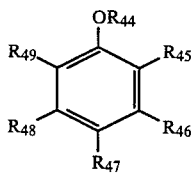

Formula (XVI)

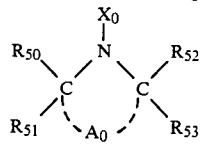

Formula (XVII)

wherein $R_{44}$ represents a hydrogen atom, aliphatic group, aromatic group, heterocyclic group, or substituted silyl group

wherein $R_{54}$, $R_{55}$, and $R_{56}$, which are the same or different, each represents aliphatic groups, aromatic groups, aliphatic oxy groups, or aromatic oxy groups. These groups may have the substituents acceptable for $R_{36}$ in formula (XII). $R_{45}$, $R_{46}$, $R_{47}$, $R_{48}$, and $R_{49}$ may be the same or different, each denoting a hydrogen atom, alkyl group, aryl group, alkoxyl group, hydroxyl group, mono- or dialkylamino group, imino group, and acylamino group. $R_{44}$ and $R_{45}$ may combine with each other to form a 5- or 6-membered ring. $R_{50}$, $R_{51}$, $R_{52}$, and $R_{53}$ may be the same or different, each denoting a hydrogen atom and alkyl group. $X_0$ denotes a hydrogen atom, aliphatic group, acyl group, aliphatic or aromatic sulfonyl group, aliphatic or aromatic sulfinyl group, oxyradical group, and hydroxyl group. $A_0$ denotes a group of non metallic atoms necessary to form a 5-, 6-, or 7-membered ring.

The following are the typical examples of the discoloration inhibitor.

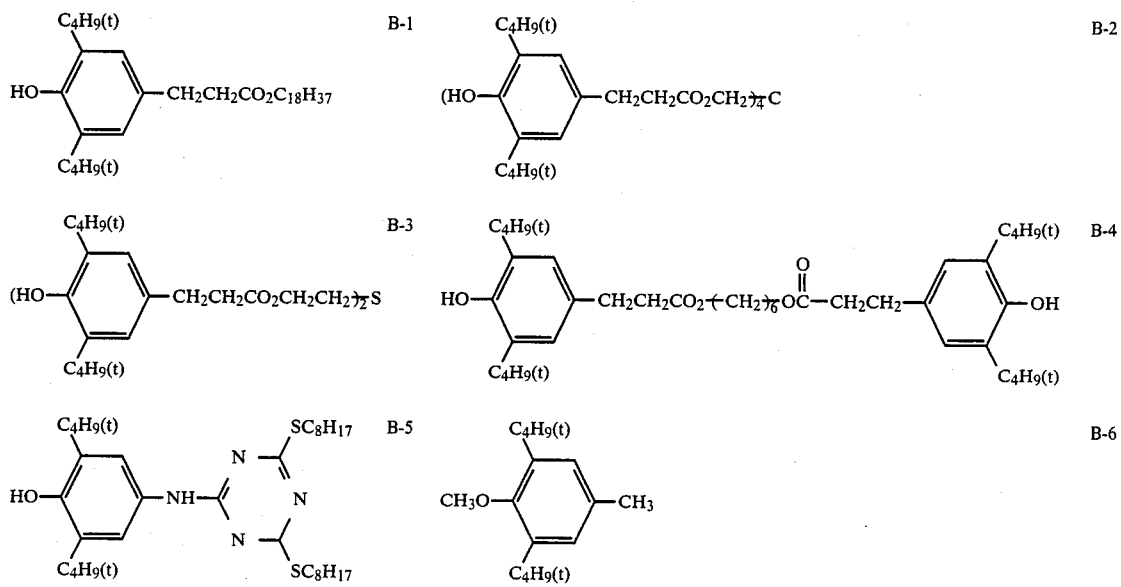

-continued
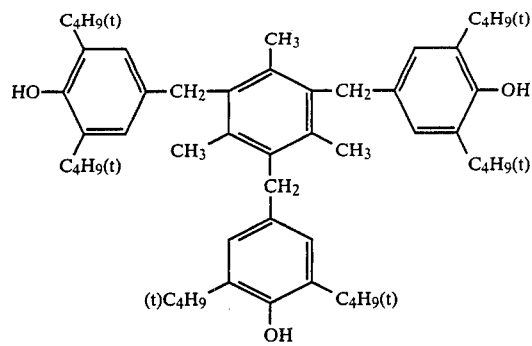 B-7
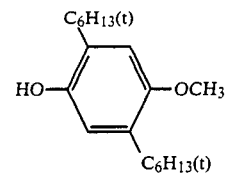 B-8
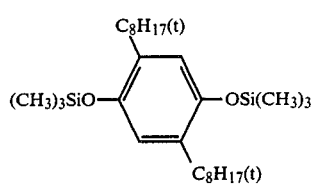 B-9
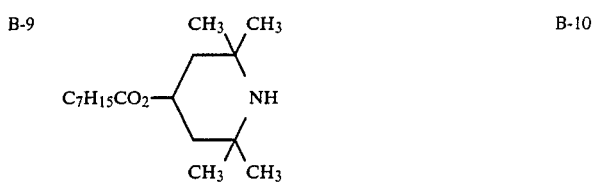 B-10
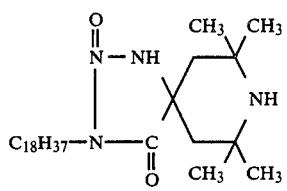 B-11
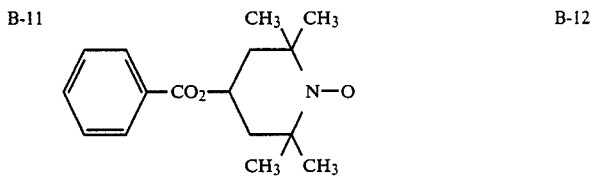 B-12
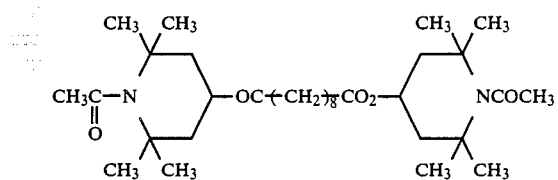 B-13
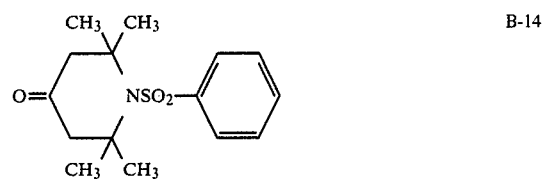 B-14
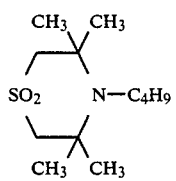 B-15
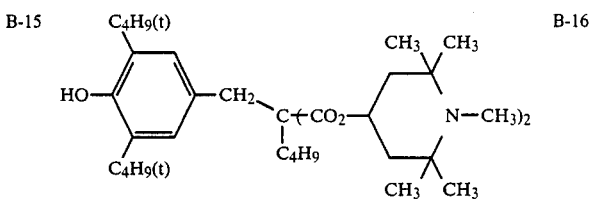 B-16
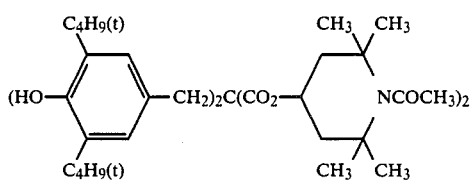 B-17
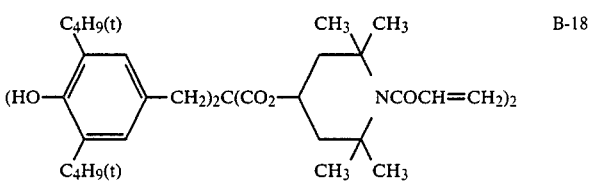 B-18

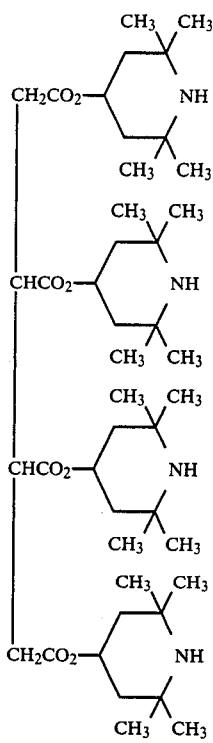

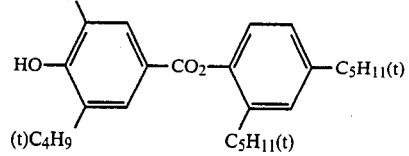

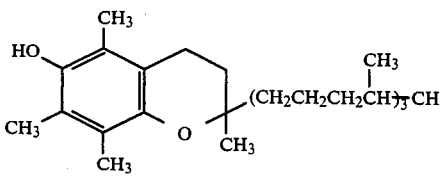

The compounds represented by formulas (XVI) and (XVII) may be used in combination with one another, and may also be used in combination with a known discoloration inhibitor.

The processes for synthesizing the compounds represented by formulas (XVI) and (XVII) and other compounds than the typical examples given above are disclosed in British Pat. Nos. 1,326,889, 1,354,313, and 1,410,846; U.S. Pat. Nos. 3,336,135 and 4,268,593; Japanese Patent Publication Nos. 1420/1976 and 6623/1977; and Japanese Patent Application (OPI) Nos. 114036/1983 and 5246/1984.

The compound represented by formula (XVI) or (XVII) is used in an amount of 0.5 to 200 wt%, preferably 2 to 150 wt% based on the yellow coupler or cyan coupler. The amount varies depending on the type of yellow coupler or cyan coupler to be used. It is preferably coemulsified with a yellow coupler or cyan coupler.

The couplers in this invention may be used in various manners according to the characteristic properties required. For example, two or more kinds of couplers may be incorporated in the same photosensitive layer, or the same coupler may be incorporated in two or more layers.

The coupler discoloration inhibitor and ultraviolet-light absorbent used in this invention may be incorporated into the photosensitive material by the known dispersing methods. Typical examples include solid dispersion method, alkali dispersion method, preferably latex dispersion method, and more preferably oil-in-water dispersion method. According to the oil-in-water dispersion method, they are dissolved in a high-boiling organic solvent (bp. 175° C. or more) or a low-boiling auxiliary solvent or a mixture thereof, and the resulting solution is finely dispersed in water or an aqueous solution of gelatin in the presence of a surface active agent. Examples of the high-boiling organic solvent are described in U.S. Pat. No. 2,322,027. For dispersing phase reversal of emulsion can be utilized. If necessary, prior to coating, the auxiliary solvent may be removed or reduced by distillation, "noodle" washing, or ultrafiltration.

Examples of the high-boiling organic solvents include phthalic esters (dibutyl phthalate, dicyclohexyl phthalate, di-2-ethylhexyl phthalate, and decyl phthalate, etc.), phosphoric or phosphonic esters (triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropylphosphate, di-2-ethylhexylphenyl phosphonate, etc.), benzoic esters (2-ethylhexyl benzoate, dodecylbenzoate, 2-ethylhexyl-p-hydroxy benzoate, etc.), amides (diethyldodecanamide, N-tetradecylpyrrolidone, etc.), alcohols or phenols (isostearyl alcohol, 2,4-di-tert-amylphenol, etc.), aliphatic carboxylic esters (dioctylazelate, glycerol tributyrate, isostearyl lactate, trioctyl citrate, etc.), aniline derivatives (N,N-dibutyl-2-butoxy-5-tert-octylaniline, etc.), and hydrocarbons (paraffin, dodecylbenzene, diisopropylnaphthalene, etc.). The auxiliary solvents are organic solvents having a boiling point higher than about 30° C., preferably from about 50° C. to about 160° C. Examples of these solvents include ethyl acetate, butyl acetate, ethyl propionate, methyl ethyl ketone, cyclohexanone, 2-ethoxyethyl acetate, dimethylformamide, etc.

The steps and effect of the latex dispersion method and the examples of latex for impregnation are described in U.S. Pat. No. 4,199,363, and West Germany Application (OLS) Nos. 2,541,274 and 2,541,230.

Usually the color couplers are used in an amount of 0.001 to 1 mol per 1 mol of photosensitive silver halides. The preferred amount of coupler is 0.01 to 0.5 mol for yellow coupler, 0.003 to 0.3 mol for magenta coupler, and 0.002 to 0.3 mol for cyan coupler.

According to this invention, the color photographic material may include a special coupler as required in addition to the yellow, magenta, and cyan couplers represented by the formulas given above. For example, it is preferable to use a colored coupler for the picture-taking color photosensitive material in order to correct the unwanted absorption of short wave light atributable to the dyes formed from the magenta and cyan couplers. Examples of such colored coupler include yellow-colored magenta coupler described in U.S. Pat. No. 4,163,670 and Japanese Patent Publication No. 39413/1982, and magenta-colored cyan coupler described in U.S. Pat. Nos. 4,004,929 and 4,138,258 and British Pat. No. 1,146,368.

The color couplers in the photosensitive material is preferably rendered nondiffusing by the incorporation of a ballast group or by the polymerization. It is possible to reduce the amount of silver coated and to obtain a higher sensitivity with a two-equivalent color coupler in which the hydrogen atoms at the coupling active positions are substituted by coupling split-off groups, than with a four-equivalent color coupler in which the coupling active positions are occupied by hydrogen atoms. It is also possible to use a coupler that forms a dye having a proper degree of diffusion, a colorless coupler, a DIR coupler that releases a development inhibitor upon coupling reaction, or a coupler that releases a development accelerator.

It is possible to improve the graininess by using the color couplers in combination with a coupler which forms a dye having a proper degree of diffusion. Such type of magenta coupler is disclosed in U.S. Pat. No. 4,366,237 and British Pat. No. 2,125,570; and such type of yellow, magenta, or cyan coupler is disclosed in European Pat. No. 96,570 and West Germany Patent Application (OLS) No. 3,234,533.

Examples of the polymerized dye-forming couplers are disclosed in U.S. Pat. Nos. 3,451,820 and 4,080,211. Examples of polymerized magenta couplers are disclosed in British Pat. No. 2,102,173 and U.S. Pat. No. 4,367,282.

The silver halide emulsion used in this invention is usually produced by mixing a solution of water-soluble silver salt (e.g., silver nitrate) and a solution of water-soluble halide (e.g., potassium bromide, sodium chloride, or potassium iodide, or a mixture thereof) in the presence of a solution of water-soluble polymer such as gelatin.

Other examples of the silver halides include mixed silver halides such as silver chlorobromide, silver chloroiodobromide, and silver iodobromide. The silver halide which is advantageously used in this invention is silver chloroiodobromide, silver chlorobromide, or silver iodobromide which contains no or less than 3 mol% of silver iodide.

The silver halide crystals may have such structure that the internal phase differs from the surface phase, or the entire crystals have a uniform phase or polyphase having joining structure or a mixture thereof. In the case of silver chlorobromide crystals having different phases, each crystal may have a nucleus or a single layer or a plurality of layers richer with silver bromide or silver chloride than the average silver halide composition. In other words, the crystals may be covered with a layer richer with silver bromide or silver chloride than the average silver halide composition. The average crystal size of silver halides should preferably be from 0.1 $\mu$m to 2 $\mu$m, and more preferably from 0.15 $\mu$m to 1 $\mu$m. For spherical crystals or nearly spherical crystals, the diameter is regarded as the crystal size, and for cubic crystals, the edge length is regarded as the crystal size. The average is obtained from their projected area.

The crystal size-distribution may be either narrow or broad. The emulsion that can be used in this invention may contain monodisperse silver halide crystals having such a narrow size-distribution that crystals having the average size plus and minus 40% account for more than 90%, especially more than 95% by number or weight of crystals. In order to produce the desired gradation, it is possible to coat two or more emulsions each containing monodisperse silver halide crystals of different size, in the form of a uniformly mixed layer or individual multiple layers. (In this case, the emulsions have substantially the same color sensitivity.) Alternatively, it is also possible to coat two or more emulsions each containing polydisperse silver halide crystals or a mixture of monodisperse silver halide crystals and polydisperse silver halide crystals, in the form of a mixed layer or multiple layers.

The emulsion used in this invention may contain silver halide crystals having the regular crystal structure such as cube, octahedron, dodecahedron, and tetradecahedron, or irregular crystal structure such as a spherical structure or the combination thereof. In addition, the emulsion may contain tabular grains having a diameter-to-thickness ratio of 5 or more, especially greater than 8, which account for more 50% of the total projected area of crystals. Moreover, the emulsion may contain a mixture of crystals of different types. The emulsion may be of the surface latent image type or the internal latent image type, the former forming the latent image on the surface of grains and the latter forming the latent image inside grains.

The photographic emulsion used in this invention can be prepared according to the processes described in P. Glafkides, *Chimie et Physique Photographique* (Pallmontel, 1967) G. F. Guffin, *Photographic Emulsion Chemistry* (Focal Press, 1966), and V. L. Zelikman, *Making and Coating Photographic Emulsion* (Focal Press, 1964). Any of an acidic process, a neutral process or an ammoniacal process can be used. As a manner of reacting a soluble silver salt with a soluble halide salt, any of the single jet method, double jet method and a combination thereof may be employed.

A process of forming grains in the presence of excess silver ion (the so-called reversal mixing process) can be employed as well. As one type of the double jet method, the "controlled double jet" process can be employed wherein the pAg in the liquid phase of silver halide formation is kept constant. This process provides a silver halide emulsion containing regular silver halide grains having an approximately monodisperse particle size.

During formation or physical ripening of the silver halide grains, cadmium salts, zinc salts, lead salts, thallium salts, iridium salts or the complex salts thereof, rhodium salts or the complex salts thereof, iron salts or the complex salts thereof, etc., may also be present. After physical ripening, silver halide emulsions are usually subjected to desalting and chemical sensitization for use in coating.

Physical ripening in the presence of silver halide solvents, e.g., ammonia, potassium thiocyanate, thioethers and thiones described in U.S. Pat. No. 3,271,157, Japanese Patent Application (OPI) Nos. 12360/1976, 82408/1978, 144319/1978, 100717/1979 and 155828/1979 provides silver halide emulsions having regular crystal forms and monodisperse grain size distribution. Removing soluble salts from emulsions before and after physical ripening can be achieved by noodle washing, flocculation precipitation or ultra-filtration, etc.

The silver halide emulsion for the present invention may be subjected to chemical sensitization; sulfur or selen sensitization, reduction sensitization and noble metal sensitization can be employed alone or in combination thereof.

Sulfur sensitization using active gelatine or sulfur-containing compounds capable reacting with silver (e.g., thiosulfates, thioureas, mercapto compounds, rhodanines, etc.); reduction sensitization using a reductive substance (e.g., stannous salts, hydrazine derivatives, formamidinesulfinic acid, silane compounds, etc.); and noble metal sensitization using noble metal compounds (e.g., complex salts of the Group VIII metals such as Pt, Ir, Pd, Rh, Fe, etc., as well as gold complex salts) can be employed alone or in combination.

Photographic emulsions in the present invention can be spectrally sensitized with photographic sensitizing dyes. Useful dyes include cyanine dyes, complex cyanine dyes, complex merocyanine dyes, holopolar cyanine dyes, hemicyanine dyes, styryl dyes and hemioxonol dyes. Particularly useful dyes are cyanine dyes, merocyanine dyes and complex merocyanine dyes.

These dyes may have any of the following basic heterocyclic nuclei which are commonly used for cyanine dyes. Pyrroline nucleus, oxazoline nucleus, thiazoline nucleus, pyrrole nucleus, oxazole nucleus, thiazole nucleus, selenazole nucleus, imidazole nucleus, tetrazole nucleus, and pyridine nucleus. Those nuclei formed by condensation of the above-mentioned nuclei with an aliphatic hydrocarbon ring or aromatic hydrocarbon ring, such as indolenine nucleus, benzindolenine nucleus, indole nucleus, benzoxazole nucleus, naphthoxazole nucleus, benzothiazole nucleus, naphthothiazole nucleus, benzoselenazole nucleus, benzimidazole nucleus, naphthoimidazole nucleus, quinoline nucleus, and imidazo-(4,5,-b)-quinoquizaline nucleus. These nuclei may be substituted on the carbon atom.

The merocyanine dye or compound merocyanine dye may have, as a nucleus having the ketomethylene structure, a 5- or 6-membered hetero ring nucleus such as pyrazolin-5-on nucleus, thiohydantoin nucleus, 2-thiooxazolidine-2,4-dione nucleus, thiazolidine-2,4-dione nucleus, rhodanine nucleus, thiobarbituric acid, 2-thioselenazolidine-2,4-dione nucleus, pyrazolo[1,5-a]benzimidazole, and pyrazolo[5,1-b]quinazolone nucleus.

These sensitizing dyes may be used alone or in combination. A combination of sensitizing dyes is often employed particularly for the purpose of supersensitization.

Together with the sensitizing dye, a supersensitizing substance such as a dye which itself is not sensitizing or a substance which substantially does not absorb visible light may be incorporated in the emulsion. For example, aminostilbene compounds substituted with a nitrogen-containing hetero ring (for example, those described U.S. Pat. Nos. 2,933,390 and 3,635,721), aromatic acid-formaldehyde condensates (for example, those described in U.S. Pat. No. 3,743,510), cadmium salts, azaindene compounds, etc., may be incorporated. The combinations described in U.S. Pat. Nos. 3,615,613, 3,615,641, 3,617,295 and 3,635,721 are particularly useful.

To the photographic emulsion for use in the present invention, various compounds can be incorporated for the purpose of stabilizing photographic properties and of preventing fog formation during the steps of producing, storing or processing of, photographic materials. Many compounds known as antifoggants or stabilizers can be added; typical examples include azoles, e.g., benzothiazolium salts, benzimidazolium salts, imidazoles, benzimidazoles (preferably 5-nitrobenzimidazole), nitroindazoles, benzotriazoles (preferably 5-methylbenzotriazoles), and triazoles; mercapto compounds (e.g., mercaptothiazoles, mercaptobenzothiazoles, mercaptobenzimidazoles, mercaptobenzoxazoles, mercaptooxadiazoles, mercaptothiadiazoles, mercaptotriazoles, mercaptotetrazoles (particularly 1-phenyl-5-mercaptotetrazole), mercaptopyrimidines, and mercaptotriazines; thiocarbonyl compounds (e.g., oxazolinethione); azaindenes (e.g., triazaindenes, tetraazaindenes (particularly 4-hydroxy-6-methyl-(1,3,3a,7)-tetraazaindene), and pentaazaindenes); benzenethiosulfonic acids; benzenethiosulfinic acids; benzenesulfonamide and purines (e.g., adenine).

Detailed description about the antifoggants and stabilizers will be found in U.S. Pat. Nos. 3,954,474 and 3,982,947; Japanese Patent Publication No. 28660/1977; Research Disclosure 17643 (December 1978) VIA-VIM; and E. J. Birr, *Stabilization of Photographic Silver Halide Emulsions* (Focal Press, 1974).

The photosensitive material of this invention may contain, as a color antifoggant or discoloration inhibitor, a hydroquinone derivative, aminophenol derivative, amine, gallic acid derivative, catechol derivative, ascorbic acid derivative, colorless coupler, or sulfoneamidephenol derivative.

The photographic material of this invention may have in the photographic emulsion layers and other hydrophilic colloid layers a brightening agent derived from stilbene, triazine, oxazole, or coumarin. It may be water-soluble but may be in the form of dispersion when water insoluble. Examples of the fluorescent brightener are described in U.S. Pat. Nos. 2,632,701, 3,269,840, and 3,359,102; British Pat. Nos. 852,075 and 1,319,763; and Research Disclosure Vol. 176, 17643 (issued December 1978), page 24, lines 9 to 36 in the left column.

In the case where the photosensitive material of this invention has in the hydrophilic colloid layers a dye and ultraviolet light absorbent, they may be mordanted by a cationic polymer. Examples of such a polymer are disclosed in British Pat. No. 685,475; U.S. Pat. Nos. 2,675,316, 2,839,401, 2,882,156, 3,048,487, 3,184,309, and 3,445,231; West Germany Patent Application (OLS) No. 1,914,362; and Japanese Patent Application (OPI) Nos. 47624/1975 and 71332/1975.

The photosensitive material of this invention may contain, as a color antifoggant, a hydroquinone derivative, aminophenol derivative, gallic acid derivative, or ascorbic acid derivative. Examples of the color antifoggant are described in U.S. Pat. Nos. 2,360,290, 2,336,327, 2,403,721, 2,418,613, 2,675,314, 2,701,197, 2,704,713, 2,728,659, 2,732,300, and 2,735,765; Japanese Patent Application (OPI) Nos. 92988/1975, 92989/1975, 93928/1975, 110337/1975, and 146235/1977; and Japanese Patent Publication No. 23813/1975.

The photosensitive material of this invention may contain a water-soluble dye in the hydrophilic colloid layers as a filter dye or for the prevention of irradiation and halation and for other purpose. Examples of such a dye are oxonol dyes, styryl dyes, merocyanine dyes, anthraquinone dyes, and azo dyes. Cyanine dyes, azomethine dyes, triarylmethane dyes, and phthalocyanine dyes may be used. It is also possible to add an oil-soluble dye to the hydrophilic colloid layer to be emulsified by the oil-in-water dispersion method.

The emulsion layers and intermediate layers of the photosensitive material of this invention are combined with gelatin or other hydrophilic colloid as the binding material and protective colloid. Examples of such gelatin or hydrophilic colloid are a gelatin derivative, graft polymer of gelatin and other polymer, protein such as albumin and casein, cellulose derivative such as hydroxyethyl cellulose, carboxymethyl cellulose, and cellulose sulfate ester, sodium alginate, sugar derivative such as starch derivative, and hydrophilic synthetic polymeric substance (homopolymer or copolymer) such as polyvinyl alcohol, polyvinyl alcohol having partial acetal groups, poly-N-vinylpyrrolidone, polyacrylic acid, polymethacrylic acid, polyacrylamide, polyvinyl imidazole, and polyvinyl pyrazole.

The gelatin may be the commercially available lime-treated gelatin or acid-treated gelatin, or enzyme-treated gelatin as disclosed in Bulletin of the Society of Scientific Photography of Japan, No. 16, p. 30 (1966). The decomposition product of gelatin formed by hydrolysis or enzymic action may be used.

The photosensitive material of this invention may contain an inorganic or organic hardening agent in the photosensitive layers or any hydrophilic colloid layer forming the backing layer.

The photosensitive material of this invention may contain a coating auxiliary and one or more surfactants for the improvement of antistatic properties, slip properties, emulsification and dispersion, antiblock properties, and other photographic properties (e.g., acceleration of development, high contrast, and sensitization).

The photosensitive material of this invention may be incorporated with, in addition to the above-mentioned additives, a variety of stabilizer, stain inhibitor, developing agent or precursor thereof, development accelerator or precursor thereof, slip agent, mordant, matting agent, antistatic agent, plasticizer, and other additives useful for the photosensitive material. Examples of the additives are described in Research Disclosure 17643 (December 1978) and 18716 (November 1979).

This invention can be applied to the multilayer-multicolor photographic material having at least two layers of different spectral sensitivity deposited on a film support. The multilayer color photographic material usually has at least a red-sensitive emulsion layer, a green-sensitive emulsion layer, and a blue-sensitive emulsion layer deposited on film support, respectively. The other of these layer may be selected as desired. The preferred order is red-sensitive, green-sensitive, and blue-sensitive starting from the support, or blue-sensitive, red-sensitive, and green-sensitive starting from the support. Each emulsion layer may be composed of two or more emulsion layers of different sensitivity, or may be composed of two or more emulsion layers of the same sensitivity with a non-sensitive layer interposed therebetween. Usually, the red-sensitive emulsion layer contains a cyan-forming coupler, the green-sensitive emulsion layer contains a magenta-forming coupler, and the blue-sensitive emulsion layer contains a yellow-forming coupler. This combination may be different in some cases.

The photosensitive material of this invention preferably includes, in addition to the silver halide emulsion layers, auxiliary layers such as subbing layer, protective layer, intermediate layer, filter layer, antihalation layer, and backing layer. Moreover, if necessary, a second UV light absorbing layer may be provided between the red-sensitive emulsion layer and the green-sensitive emulsion layer. This UV light absorbing layer preferably contain the UV light absorber described above or any other known UV light absorber.

In the photosensitive material of this invention, the photographic emulsion layer and other layers are coated on a flexible support such as plastic film, paper, and cloth, or a rigid support such as glass, porcelain, and metal, which are commonly used for photosensitive materials. An example of the flexible support is a film of semi-synthetic or synthetic polymer such as cellulose nitrate, cellulose acetate, cellulose acetate butyrate, polystyrene, polyvinyl chloride, polyethylene terephthalate, and polycarbonate, and paper coated or laminated with baryta layer or α-olefin polymer (e.g., polyethylene, polypropylene, and ethylene/butene copolymer). The support may be colored by using a dye or pigment, or may be black in color for light shielding. The support is usually applied an undercoating for the improved bonding with the photographic emulsion layers. Prior to or after the undercoating, the surface of the support may be subjected to glow discharge, corona discharge, UV light irradiation, or flame treatment.

The coating of the photographic emulsion layers and other hydrophilic colloid layers may be conducted by the known manners such as dip coating, roller coating, curtain coating, and extrusion coating. If necessary, a multiplicity of layers may be coated at one time by the method disclosed in U.S. Pat. Nos. 2,681,294, 2,761,791, 3,526,528, and 3,508,947.

For color development processing of the photosensitive material of this invention, it is desirable to use an alkaline aqueous solution composed mainly of a color developing agent of aromatic primary amine type. As the color developing agent, an aminophenol compound may be used, but the use of a p-phenylenediamine compound is preferable. Examples of such a compound are 3-methyl-4-amino-N,N-diethylaniline, 3-methyl-4-amino-N-ethyl-N-β-hydroxyethylaniline, 3-methyl-4-amino-N-ethyl-N-β-methanesulfonamideethylaniline, and 3-methyl-4-amino-N-ethyl-N-β-methoxyethylaniline, sulfates thereof, hydrochlorides thereof, and p-toluenesulfonates thereof. The amines are used in the form of salts, because they are stable rather than the free form.

The color developing solution generally contains a pH buffer such as alkali metal carbonate, borate, and phosphate; a development retarder such as bromide, iodide, benzimidazole, benzothiazole, and mercapto compound; and an antifoggant. In addition, the color developing solution may be incorporated, as required, with a preservative such as hydroxylamine and sulfite; an organic solvent such as triethanolamine and ethylene glycol; a development accelerator such as benzyl alcohol, polyethylene glycol, quaternary ammonium salt, and amine; dye forming couplers and competitive couplers; a nucleating agent such as sodium boron hydride; an auxiliary developing agent such as 1-phenyl-3-pyrazolidone; a thickening agent; a chelating agent such as amino polycarboxylic acid, amino polysulfonic acid, alkylsulfonic acid, and phosphonocarboxylic acid; and an antioxidant as disclosed in West Germany Patent Application (OLS) No. 2,622,950.

In the development processing of color reversal material, black and white development is usually performed prior to color development. For the black and white developing solution, it is possible to use any known black and white developing agent such as dihydroxybenzenes (e.g., hydroquinone), 3-pyrazolidones (e.g., 1-phenyl-3-pyrazolidone), and aminophenols (e.g., N-methyl-p-aminophenol), individually or in combination with one another.

After color development, the photographic emulsion layer usually undergo bleaching treatment. The bleaching may be performed simultaneously with or separately from fixing treatment. The bleaching agent includes compounds of polyvalent metal such as iron (III), cobalt (III), chromium (VI), and copper (II), peracids, quinones, and nitron compounds. Examples of the bleaching agent are ferricyanides, dichromates, organic complex salts of iron (III) or cobalt (III) (e.g., complex salts of aminopolycarboxylic acid such as ethylenediaminetetraacetic acid, ethylenetriaminepentaacetic acid, nitrilotriacetic acid, and 1,3-diamino-2-propanoltetraacetic acid; and complex salts of organic acid such as citric acid, tartaric acid, and malic acid), persulfates, manganates, and nitrosophenol. Iron (III) ethylenediaminetetraacetate and persulfates are preferable among them in view of rapid treatment and environmental pollution. Especially, iron (III) ethylenediaminetetraacetate is useful for the independent bleaching solution as well as the combined developing and fixing bath.

The bleaching bath or the bleach-fix bath may be incorporated with a variety of accelerators as required. Examples of the bleach accelerators are bromine ions and iodine ions; thiourea compounds as disclosed in U.S. Pat. No. 3,706,561, Japanese Patent Publication Nos. 8506/1970 and 26586/1974, and Japanese Patent Application (OPI) Nos. 32735/1978, 36233/1978, and 37016/1978; thiol compounds as disclosed in Japanese Patent Application (OPI) Nos. 124424/1978, 95631/1878, 57831/1978, 32736/1978, 65732/1978, and 52534/1979, and U.S. Pat. No. 3,893,858; heterocyclic compounds as disclosed in Japanese Patent Application (OPI) Nos. 59644/1974, 140129/1975, 28426/1978, 141623/1978, 104232/1978, and 35727/1979; thioether compounds as disclosed in Japanese Patent Application (OPI) Nos. 20832/1977, 25064/1980, and 26506/1980; tertiary amines as disclosed in Japanese Patent Application (OPI) No. 84440/1973; and thiocarbamoyls as disclosed in Japanese Patent Application (OPI) No. 42349/1974. They may be used individually or in combination with one another. Among the bleach accelerators identified above, bromine ions, iodine ions, thiol compounds, and disulfide compounds are particularly useful. They are effective when used for bleach-fix of the picture-taking color photosensitive material.

The fixing agent is a thiosulfate, thiocyanate, thioether compound, thiourea, and iodide. A thiosulfate is preferable. The bleach-fix bath or the fixing bath is preferably incorporated with a preservative such as sulfite, bisulfite, and carbonyl-bisulfite adduct.

Bleach-fix or fixing is usually followed by washing. Water for washing may be incorporated with a variety of known compounds for the prevention of precipitation and the saving of water. For example, a water softener such as inorganic phosphoric acid, aminopolycarboxylic acid, and organic phosphoric acid may be added for the prevention of precipitation; and an antiseptic may be added for the inhibition of bacteria, algae, and molds. Other additives that may be added as required include a hardening agent such as magnesium salt and aluminum salt and a surface active agent that makes for uniform drying. A compound as disclosed in Phot. Sci, Eng., Vol. 6 (1965), p. 344–359, Water Quality Criteria, by L. E. West may be used as an additive. The addition of a chelating agent and antiseptic agent is paticularly effective.

The developed dyes are deteriorated by light and heat and also discolored by molds during storage. In particular, cyan photographic images are easily vulnerable by molds. Thus, it is desirable to use a mold protecting agent such as 2-thiazolylbenzimidazole as disclosed in Japanese Patent Application (OPI) No. 157244/1982. The mold protecting agent may be incorporated into the photosensitive material or may be added to the development process. In other words, it may be added in any step so long as it remains in the processed photosensitive material.

The washing is usually performed in the counter-current manner using two or more vessels for the saving of water. The washing step may be replaced by the multistage countercurrent stabilizing step as disclosed in Japanese Patent Application (OPI) No. 8543/1982. This step requires 2 to 9 countercurrent baths incorporated with a variety of compounds for the stabilization of photographic images. Examples of the additives are formalin and buffers to adjust the pH of the gelatin emulsion. (The buffers are prepared by combining boric acid, metaboric acid, borax, phosphate, carbonate, potassium hydroxide, ammonia water, monocarboxylic acid, dicarboxylic acid, polycarboxylic acid, etc. with one another.) Other additives are water softener (e.g., inorganic phosphoric acid, aminopolycarboxylic acid, organic phosphoric acid, aminopolysulfonic acid, and phosphonocarboxylic acid), antiseptic agent (e.g., benzoisothiazolinone, isothiazolone, 4-thiazolinebenzimidazole, and halogenated phenol), surface active agent, fluorescent brightener, and hardening agent. Two or more additives for the same object may be used together.

In order to adjust the pH of the emulsion after processing, it is preferable to add an ammonium salt such as ammonium chloride, ammonium nitrate, ammonium sulfate, ammonium phosphate, ammonium sulfite, and ammonium thiosulfate.

The silver halide color photosensitive material of this invention may be incorporated with precursors of color developing agents so as to simplify and speed up the processing. Examples of such precursors are indoaniline compounds (as disclosed in U.S. Pat. No. 3,342,597), Schiff base compounds (as disclosed in U.S. Pat. No. 3,342,599 and Research Disclosure Nos. 14850 and 15159), aldol compounds (as disclosed in Research Disclosure No. 13924), metal salt complexes (as disclosed in U.S. Pat. No. 3,719,492), urethane compounds (as disclosed in Japanese Patent Application (OPI) No.

135628/1978), and salt type precursors (as disclosed in Japanese Patent Application (OPI) Nos. 6235/1981, 16133/1981, 59232/1981, 67842/1981, 83734/1981, 83735/1981, 83736/1981, 89735/1981, 81837/1981, 54430/1981, 106241/1981, 107236/1981, 97531/1982, and 83565/1982).

The silver halide color photosensitive material of this invention may be incorporated with a 1-phenyl-3-pyrazolidone as required so as to accelerate color development. Examples of such a compound are disclosed in Japanese Patent Application (OPI) Nos. 64339/1981, 144547/1982, 211147/1982, 50532/1983, 50536/1983, 50533/1983, 50534/1983, 50535/1983, and 115438/1983.

The processing solutions for the photosensitive material of this invention is used at 10° C. to 50° C., although the standard temperature is 33° C. to 38° C. The temperature may be raised to accelerate processing and to reduce the processing time. To the contrary, the temperature may be lowered to improve the photographic image quality and the stability of the processing solutions. For the saving of silver in the photosensitive material, the processing may be intensified by using cobalt or hydrogen peroxide as disclosed in West Germany Pat. No. 2,226,770 and U.S. Pat. No. 3,674,499.

The processing baths may be provided with a heater, temperature sensor, level sensor, circulating pump, filter, floating lid, squeezer, and the like, as required.

In the present invention, the silver halide color photosensitive material is formed by combining a specific magenta coupler and chroman derivative together. Therefore, it is greatly improved in the preservation of quality of photographic image. In addition, it is free from discoloration and fogging and keeps the photographic color image without decreasing the color density. Furthermore, white background portions of the photosensitive material do not create the yellow stains by light, heat, and moisture after the development processing and discoloration is minimized over the entire density range of photographic color images and there is no change in color balance.

It is to be understood that the 6-hydroxy-2,4,4,7-tetramethylchroman derivative of this invention produces a strong antioxidant action, and it is useful as an antioxidizing agent for synthetic polymeric products and petroleum products such as dyes, rubbers, and plastics. It is also effective in preventing the discoloration of color photographic images formed by the subtractive color process.

The invention is now described in more detail with reference to the following examples. Examples 1 to 3 are directed to the syntheses of 2-(2-alkoxy-5-hydroxy-4-methylphenyl)-6-hydroxy-2,4,4,7-tetramethylchroman derivatives as shown in the synthesis scheme (1). Example 4 is directed to the syntheses of 2-(5-alkoxy-2-hydroxy-4-methylphenyl)-6-hydroxychroman derivatives as shown in the synthesis scheme (2). Examples 5 to 13 are directed to the application of the 6-hydroxy-2,4,4,7-tetramethylchroman as an antioxidant.

EXAMPLE 1

(1) Synthesis of compound 2

50 g (0.152 mol) of compound 1 was heated with 50 ml of toluene and 43 ml (0.456 mol) of acetic anhydride under reflux for 6 hours. The reaction solution was evaporated to dryness under reduced pressure. 12.5 ml of isopropanol and 112.5 ml of n-hexane were added for crystallization. On filtration of crystals, there was obtained 57.8 g of compound 2.

Yield: 92%, m.p. 163° C.

(2) Synthesis of exemplified compound (3)

To 41.2 g (0.10 mol) of compound 2 were added 80 ml of dimethyl-formamide, 29.9 g (0.12 mol) of dodecyl bromide, and 16.5 g (0.12 mol) of anhydrous potassium carbonate, followed by stirring at 70° C. for 8 hours. While the reaction solution was kept at 25° C., there was added a solution of 16.5 g (0.30 mol) of potassium hydroxide in 165 ml of methanol, followed by stirring for 30 minutes. Solids were removed by filtration, and the filtrate was poured into ice-cooled acid water (with hydrochloric acid) for neutralization, followed by extraction with 300 ml of ethyl acetate. After thorough washing with water, the ethyl acetate was distilled away under reduced pressure, and 125 ml of n-hexane was added for crystallization. The crystals were filtered off and then recrystallized from acetonitrile. Thus there was obtained 38.7 g of the exemplified compound (3) in the form of colorless crystals.

Yield: 78%, m.p. 166°–167° F.

IR (KBr, cm$^{-1}$): 3255, 1505, 1195, 1170, 883, 870.

NMR (CDCl$_3$, δ): 6.79 (1H, s), 6.73 (1H, s), 6.56 (2H, s), 4.58 (1H, s), 4.48 (1H, s), 3.91 (2H, t, J=6.7 Hz), 2.92 (1H, d, J=15 Hz), 2.13 (3H, s), 1.91 (1H, d, J=15 Hz), 1.63 (3H, s), 1.9–1.1 (20H, m), 1.19 (3H, s), 0.88 (3H, t, J=6 Hz), 0.80 (3H, s).

M/S (m/e): 496 (M$^+$)

Elemental analysis (C$_{32}$H$_{48}$O$_4$). Found: C: 77.26%; H: 9.87%; Calcd: C: 77.38%; H: 9.74%.

EXAMPLE 2

Synthesis of exemplified compound (A-8)

To 41.2 g (0.10 mol) of compound 2 was added 150 ml of dimethyl acetamide for dissolution. While this solution was kept at 5° to 10° C., 4.8 g (0.12 mol) of sodium hydride (60% dispersion in oil) was added with stirring. Then 19.7 g (0.12 mol) of hexyloxyethylene chloride was added over 15 minutes, followed by stirring at 27° to 29° C. for 4 hours. 20 ml of methanol was added and then there was added a solution of 16.5 g (0.30 mol) of potassium hydroxide in 165 ml of methanol, followed by stirring for 30 minutes. The reaction solution was poured into ice-cooled acid water (with hydrochloric acid) for neutralization, followed by extraction with 300 ml of ethyl acetate. After thorough water washing, the ethyl acetate was distilled away under reduced pressure, and 125 ml of n-hexane was added for crystallization. The crystals were filtered off and then recrystallized from 100 ml of acetonitrile. Thus there was obtained 31.6 g of the exemplified compound (A-8) in the form of colorless crystals.

Yield: 69%, m.p. 198°–199° C.

IR (KBr, cm$^{-1}$): 3100, 1500, 1195, 1170, 883, 870.

NMR (CDCl$_3$/DMSO-d$_6$, δ): 7.95 (1H, broad s), 7.82 (1H, broad s), 6.82 (1H, s), 6.71 (1H, s), 6.58 (1H, s), 6.55 (1H, s), 4.15–3.95 (2H, m), 3.90–3.70 (2H, m), 3.53 (2H, t, J=6.7 Hz), 2.99 (1H, d, J=15 Hz), 2.16 (3H, s), 2.10 (3H, s), 1.85 (1H, d, J=15 Hz), 1.62 (3H, s), 1.8–1.1 (8H, m), 1.20 (3H, s), 0.88 (3H, m), 0.70 (3H, s).

M/S (m/e): 457 (M$^+$)

Elemental analysis (C$_{28}$H$_{40}$O$_5$). Found: C: 73.37%; H: 9.08%; Calcd: C: 73.49%; H: 9.03%.

EXAMPLE 3

Synthesis of exemplified compound (A-7)

To 41.2 g (0.10 mol) of compound 2 was added 150 ml of dimethyl acetamide for dissolution. While this solution was kept at 5° to 10° C., 4.8 g (0.12 mol) of sodium hydride (60% dispersion in oil) was added with stirring. Then 30.7 g (0.11 mol) of 2-bromodecanoic acid was added over 15 minutes, followed by stirring at 27° to 30° C. for 5 hours. The reaction solution was cooled to 5°–10° C., and 20 ml of methanol was added. The reaction solution was poured into ice-cooled acid water (with hydrochloric acid) for neutralization, followed by extraction with 300 ml of ethyl acetate. After thorough water washing, the ethyl acetate was dried over sodium sulfate. The sodium sulfate was filtered off and the solvent was distilled away. To the residues were added 150 ml of ethanol and 41.4 g (0.30 mol) of anhydrous potassium carbonate, followed by stirring at 27°–30° C. for 1 hour. Solids were filtered off and the filtrate was poured into ice-cooled acid water (with hydrochloric acid) for neutralization, followed by extraction with 300 ml of ethyl acetate. The organic layer was thoroughly washed with water and then dried over sodium sulfate. The sodium sulfate was filtered off and the solvent was distilled away. n-Hexane was added for crystallization. The crystals were filtered off and then recrystallized from n-hexane. Thus there was obtained 39.5 g of the exemplified compound (A-7) in the form of colorless crystals.

Yield: 75%, m.p. 121°–124° C.

IR (KBr, cm$^{-1}$): 3400, 1720, 1505, 1185, 872.

NMR (CDCl$_3$, δ): 6.85 (1H, s), 6.70 (1H, s), 6.55 (1H, s), 6.34 (1H, s), 5.10 (1H, s), 4.90 (1H, s), 4.8–4.5 (1H, m), 4.17 (2H, t, J=6 Hz), 3.15–2.85 (1H, m), 2.05 (3H, s), 2.0 (3H, s), 2.0–0.7 (30H, m).

M/S (m/e): 527 (M+)

Elemental analysis (C$_{32}$H$_{47}$O$_6$). Found: C: 72.77%; H: 8.82%; Calcd: C: 72.48%; H: 8.79%.

EXAMPLE 4

Synthesis of compound 5

To 50 g (0.152 mol) of compound 1 was added 200 ml of toluene and 25 g (0.288 mol) of manganese dioxide, followed by heating under reflux for 2 hours. The reaction solution was cooled with ice for crystallization, and the crystals were filtered off. Upon recrystallization from 300 ml of ethyl acetate, there was obtained 45.2 g of compound 5 in the form of dark red crystals.

Yield: 91%, m.p. 215°–218° C.

Synthesis of compound 6

To 50 g (0.153 mol) of compound 5 was added 200 ml of dimethyl acetamide for dissolution. To the resulting solution were added 12.5 ml (0.162 mol) of methanesulfonyl chloride and then 22.5 ml (0.161 mol) of triethylamine dropwise with stirring at 5°–10° C. over 30 minutes. The reaction solution was poured into iced-water, followed by extraction with 200 ml of ethyl acetate. The organic layer was washed with water and dried over sodium sulfate. The sodium sulfate was filtered off and the ethyl acetate was distilled away. Upon crystallization from mkethanol, there was obtained 45 g of compound 6 in the form of colorless crystals.

Yield: 72.6%, m.p. 133°–136° C.

Synthesis of compound 7

To 40.4 g (0.100 mol) of compound 6 was added 400 ml of ethyl acetate for dissolution. To the resulting solution were added 18 g (0.202 mol) of diethylhydroxyamine with stirring at 20°–25° C., followed by stirring for 2 hours. The reaction solution was poured into acid water (with hydrochloric acid), followed by extraction with ethyl acetate. The organic layer was washed with water and dried over sodium sulfate. The sodium sulfate was filtered off and the ethyl acetate was distilled away. Thus there was obtained 40.4 g of compound 7 in the form of crude oil.

Yield: 99.5%.

Synthesis of compound 9

To 20.3 g (0.050 mol) of compound 7 was added 20 ml of acetonitrile and 7.1 ml (0.075 mol) of acetic anhydride, followed by heating under reflux for 8 hours. The reaction solution was evaporated to dryness under reduced pressure. To the resulting residues was added 100 ml of dimethyl acetamide for dissolution. To the resulting solution were added 4.3 ml (0.055 mol) of methanesulfonyl chloride with stirring at 20°–25° C., and 8.4 ml (0.060 mol) of triethylamine dropwise over 15 minutes. Stirring was continued at 25°–30° C. for 30 minutes. The reaction solution was poured into ice-cooled acid water (with hydrochloric acid), followed by extraction with 100 ml of ethyl acetate. The organic layer was washed with water and dried over sodium sulfate. The sodium sulfate was filtered off and the ethyl acetate was distilled away. Upon crystallization from methanol, there was obtained 24.7 g of compound 9 in the form of colorless crystals.

Yield: 94%, m.p. 158° C.

Synthesis of compound 10

26.3% of compound 9 was added to a solution of 4.2 g of potassium hydroxide in 84 ml of methanol, with stirring at 5°–10° C. Stirring was continued at 20°–25° C. for 1 hour. The reaction solution was poured into ice-cooled acid water (with hydrochloric acid), followed by extraction with 100 ml of ethyl acetate. The organic layer was washed with water and dried over sodium sulfate. The sodium sulfate was filtered off and the ethyl acetate was distilled away. Thus there was obtained 23.2 g of compound 10 in the form of viscosity oil.

Yield: 96%.

Synthesis of exemplified compound (A-10)

To 24.2 g (0.050 mol) of compound 10 was added 120 ml of dimethyl acetamide for dissolution. While this solution was kept at 5° to 10° C., 2.4 g (0.060 mol) of sodium hydride (60% dispersion in oil) was added with stirring. Then 11.6 g (0.060 mol) of octyl bromide was added dropwise, followed by stirring at 27° to 30° C. for 5 hours. After addition of 20 ml of methanol, the reaction solution was poured into ice-cooled acid water (with hydrochloric acid), followed by extraction with 150 ml of ethyl acetate. After thorough water washing, the ethyl acetate was distilled away. To the resulting residues was added a solution of 11.2 g (0.200 mol) of potassium hydroxide in 112 ml of methanol, followed by heating under reflux for 4 hours. The reaction solution was poured into ice-cooled acid water (with hydrochloric acid), followed by extraction with 150 ml of ethyl acetate. After water washing, the organic layer was dried over sodium sulfate. The sodium sulfate was filtered off and the ethyl acetate was distilled away. n-Hexane was added for crystallization. The crystals were filtered off and then recrystallized from n-hexane. Thus there was obtained 15 g of the exemplified compound (A-10) in the form of colorless crystals.

Yield: 68%, m.p. 85°–87° C.

IR (KBr, cm$^{-1}$): 3380, 1505, 1180, 870.

NMR (CDCl$_8$, δ): 7.72 (1H, s), 6.68–6.60 (4H, m), 4.82 (1H, s), 3.82 (2H, t, J=6.7 Hz), 2.53 (1H, d, J=16 Hz), 2.15 (3H, s) 2.12 (3H, s), 1.98 (1H, d, J=16 Hz), 1.65 (3H, s), 1.9–1.0 (12H, m), 1.10 (3H, s), 1.1–0.7 (3H, m).

M/S (m/e): 441 (M+)

Elemental analysis (C$_{28}$H$_{34}$O$_4$).

Found: C: 76.23%; H: 9.28%; Calcd: C: 76.15%; H: 9.36%.

EXAMPLE 5

10 g of cyan coupler, 2-{α-(1,4-di-tert-amylphenoxy)-butylamido}-4,6-dichloro-5-methylphenol was dissolved in 10 ml of tricresyl phosphate and 20 ml of ethyl acetate. The resulting solution was emulsified and dispersed into 80 g of gelatin solution containing 8 ml of 1% aqueous solution of sodium dodecylbenzenesulfonate.

The thus obtained emulsified dispersion was mixed with 145 g (7 g as Ag) or red sensitive silver chlorobromide (Br 50 mol%) emulsion. Sodium dodecylbenzenesulfonate as a coating auxiliary was added. The resulting emulsion was coated on a paper support with both sides laminated with polyethylene. The coating amount of the coupler was 400 mg/m$^2$.

The emulsion layer was further coated with a gelatin protective layer (gelatin 1 g/m$^2$). Thus there was obtained Sample A.

Sample B to E were prepared in the same manner as mentioned above, except that an antioxidant (a compound of this invention or a comparative compound) was added in an amount of 50 mol% based on the coupler as shown in Table 1.

Sample F was prepared in the same manner as mentioned above, except that the coupler was replaced by 4-chloro-2-}2-(methanesulfonamide)-benzamide}-5-α-(3-pentadecylphenoxy)butylamidephenol. Samples G to J were prepared in the same manner as mentioned above, except that an antioxidant (a compound of this invention or a comparative compound) was added in an amount of 50 mol% based on the coupler as shown in Table 1.

Each sample was exposed for 1 second at 1000 lux and treated with the following processing solution.

| Developing solution | |
|---|---|
| Benzyl alcohol | 15 ml |
| Diethylenetriamine pentaacetic acid | 5 g |
| KBr | 0.4 g |
| Na$_2$SO$_3$ | 5 g |
| Na$_2$CO$_3$ | 30 g |
| Hydroxylamine sulfate | 2 g |
| 4-amino-3-methyl-N—ethyl-N—β-(methane-sulfonamide)ethylaniline.3/2H$_2$SO$_4$.H$_2$O | 4.5 g |
| Water to make 1000 ml | pH 10.1 |
| Bleach-fixing solution | |
| Ammonium thiosulfate (70 wt %) | 150 ml |
| Na$_2$SO$_3$ | 5 g |
| Na [Fe(EDTA)] | 40 g |
| EDTA | 4 g |
| Water to make 1000 ml | pH 6.8 |

| Processing step | Temperature | Time |
|---|---|---|
| Development | 33° C. | 3 min 30 sec |
| Bleach-fix bath | 33° C. | 1 min 30 sec |
| Washing with water | 28–35° C. | 3 min |

The dye image formed on each sample was examined for light fastness by exposing the sample to a xenon tester (100,000 lux) with an ultraviolet-light absorbing filter (a production of Fuji Photo Film Co., Ltd.) (400 nm and below) for 500 hours. The light fastness is expressed in terms of the residual dye density (percent) at an initial density of 2.0 after exposure.

The dye image was also examined for heat fastness by keeping the sample at 100° C. for 100 hours at a dark place. The heat fastness is expressed in terms of the residual dye density (percent) at an initial density of 2.0.

The results are shown in Table 1.

TABLE 1

| Sample | Antioxidant | Residual dye density | After exposure to xenon tester for 100 hours | Residual dye density | 100° C. 100 hours | Remarks |
|---|---|---|---|---|---|---|
| A | — | | 57% | | 51% | Control |
| B | Exemplified Compound (A-5) | | 86% | | 76% | This invention |
| C | Exemplified Compound (A-10) | | 85% | | 78% | This invention |
| D | 2,6-di-tert-butyl-4-methyl phenol | | 60% | | 56% | Comparison |
| E | 2,2,6,6-tetra-methyl-4-piperi-dinol | | 58% | | 55% | Comparison |
| F | — | | 48% | | 94% | Control |
| G | Exemplified Compound (A-3) | | 85% | | 98% | This invention |
| H | Exemplified Compound (A-11) | | 83% | | 97% | This invention |
| I | 2,6-di-tert-butyl-4-methyl phenol | | 53% | | 94% | Comparison |
| J | 2,2,6,6-tetra-methyl-4-piperi- | | 59% | | 95% | Comparison |

TABLE 1-continued

| Sample | Antioxidant | Residual dye density | After exposure to xenon tester for 100 hours | Residual dye density | 100° C. 100 hours | Remarks |
|---|---|---|---|---|---|---|
| | dinol | | | | | |

EXAMPLE 6

Sample K was prepared in the same manner as in Example 5, except that the as the cyan coupler α-pyraloyl-2,4-dioxo-5,5-dimethyl-3-oxazolidinyl)-2-chloro-5-{α-(2,4-di-tert-aminophenoxy)-butylamido}acetanilide was used and that a blue-sensitive silver chlorobromide (Br 80 mol%) emulsion was used in place of red-sensitive silver chlorobromide emulsion. Samples L to O were prepared in the same manner as mentioned above, except that an antioxidant (a compound of this invention or a comparative compound) was added in an amount of 50 mol% based on the coupler as shown in Table 2.

The samples were exposed and developed in the same manner as in Example 5.

The dye image formed on each sample was examined for light fastness by exposing the sample to a xenon tester for 200 hours. The light fastness is expressed in terms of the residuan dye density (percent) at an initial density of 2.0 after exposure.

The dye image was also examined for heat fastness by keeping the sample at 100° C. for 500 hours at a dark place. The heat fastness is expressed in terms of residual dye density (percent) at an initial density of 2.0.

The results are shown in Table 2.

TABLE 2

| Sample | Antioxidant | Residual dye density | After exposure to xenon tester for 200 hours | Residual dye density | 100° C. 500 hours | Remarks |
|---|---|---|---|---|---|---|
| K | — | | 74% | | 91% | Control |
| L | Exemplified Compound (A-5) | | 93% | | 98% | This invention |
| M | Exemplified Compound (A-10) | | 91% | | 97% | This invention |
| N | 2,6-di-tert-butyl-4-methyl-phenol | | 76% | | 91% | Comparison |
| O | 2,2,6,6-tetra-methyl-4-piperidinol | | 74% | | 92% | Comparison |

It is noted from Table 1 and 2 that the compound of this invention exhibits an outstanding antioxidizing effect.

EXAMPLE 7

IIR (Polysar Butyl #100, degree of unsaturation 0.7%, a product of Polymer Corp.) was compounded according to the following formulation.

| | parts by weight |
|---|---|
| Polysar Butyl #100 | 100 |
| Hard clay | 120 |
| Zinc oxide | 5 |
| Stearic acid | 2 |
| Sulfur | 1 |
| Tetramethylthiuram disulfide | 2 |
| SRF carbon | 10 |
| Mercaptobenzothiazole | 0.5 |

The compounded rubber was roll-milled and press-cured at 160° C. for 45 minutes to make a 2 mm thick sheet. Test specimen (a) conforming to JIS No. 3 dumbell was punched out of this sheet.

In the same manner as above, there were prepared test specimens (b) to (e) each containing 1.5 parts by weight of antioxidant as shown in Table 3.

The specimens were subjected to accelerated aging at 120° C. for 100 hours in a Geer oven. The aging resistance was evaluated by the ratio of the tensile strength (kg/mm²) and elongation (%) measured after aging to those measured before aging, and was expressed in terms of risidual value (%). The results are shown in Table 3.

TABLE 3

| | | Aging properties | | |
|---|---|---|---|---|
| Sample | Antioxidant | Residual Cencile strength (%) | Residual elongation (%) | Remarks |
| a | — | 58 | 25 | Control |
| b | Comparative compound | 71 | 53 | Comparison |
| c | Exemplified compound (A-5) | 97 | 96 | This invention |
| d | Exemplified compound (A-7) | 95 | 94 | This invention |
| e | Exemplified compound (A-10) | 96 | 95 | This invention |

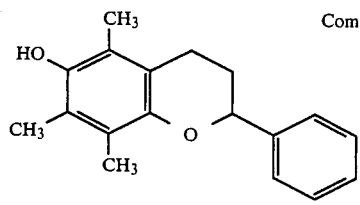

Comparative compound (The compound described in Japanese Patent Application (OPI) No. 14771/1977.)

It is noted from Table 3 that the compound of this invention is by far superior to the other compounds of similar structure when used as an antioxidant.

EXAMPLE 8

10 g of comparative magenta coupler (a), 1-(2,4,6-trichlorophenyl)-3-{(2-chloro-5-tetradecanamido)anilino}-2-pyrazolin-5-on was dissolved in 20 ml of tricresyl phosphate and 20 ml of ethyl acetate. The resulting solution was emulsified and dispersed into 80 g of gelatin solution containing 8 ml of 1% aqueous solution of sodium dodecylbenzenesulfonate.

The thus obtained emulsified dispersion was mixed with 145 g (7 g as Ag) of green-sensitive silver chlorobromide (Br 50 mol%) emulsion. Sodium dodecylbenzenesulfonate as a coating auxiliary was added. The resulting emulsion was coated on a paper support with both sides laminated with polyethylene. The coating amount of the coupler was 400 mg/m$^2$.

The emulsion layer was further coated with a gelatin protective layer (gelatin 1 g/m$^2$). Thus there was obtained Sample A.

Samples B to W were prepared in the same manner as mentioned above, except that each of them was incorporated with a magenta coupler of this invention or a comparative magenta coupler and a compound of formula (I) of this invention or a comparative compound as shown in Table 4. The amount of the compound of formula (I) or comparative compound was 50 mol% based on the amount of the magenta coupler.

Each sample was exposed for 1 second at 1000 lux and treated with the following processing solutions.

| Developing solution | |
|---|---|
| Benzyl alcohol | 15 ml |
| Diethylenetriamine pentaacetic acid | 5 g |
| KBr | 0.4 g |
| Na$_2$SO$_3$ | 5 g |
| Na$_2$CO$_3$ | 30 g |
| Hydroxylamine sulfate | 2 g |
| 4-amino-3-methyl-N—ethyl-N—β-(methane-sulfonamide)ethylaniline.3/2H$_2$SO$_4$.H$_2$O | 4.5 g |
| Water to make 1000 ml | pH 10.1 |
| Bleach-fixing solution | |
| Ammonium thiosulfate (70 wt %) | 150 ml |
| Na$_2$SO$_3$ | 5 g |
| Na [Fe(EDTA)] | 40 g |
| EDTA | 4 g |
| Water to make 1000 ml | pH 6.8 |

| Processing step | Temperature | Time |
|---|---|---|
| Developing | 33° C. | 3 minute 30 second |
| Bleach-fixing | 33° C. | 1 minute 30 second |
| Washing | 28–35° C. | 3 minute |

The dye image formed on each sample was examined for light fastness by exposing the sample to a xenon tester (200,000 lux) with an ultra-violet light absorbing filter (a product of Fuji Photo Film Co., Ltd.) (absorbing the light of 400 nm and below) for 6 days.

The results are shown in Table 4.

TABLE 4

| Sample | Magenta coupler | Discoloration inhibitor | Change in magenta density (Initial density: 2.0) | Change in density of yellowing in white background | Remarks |
|---|---|---|---|---|---|
| A | Comparative coupler (a) | — | −1.75 | +0.31 | Comparative example |
| B | " | Exemplified compound (A-1) | −0.48 | +0.11 | Comparative example |
| C | " | Exemplified compound (A-20) | −0.45 | +0.13 | Comparative example |
| D | Comparative coupler (b) | — | −1.70 | +0.34 | Comparative example |
| E | " | Exemplified compound (A-4) | −0.47 | +0.10 | Comparative example |
| F | " | Exemplified compound (A-5) | −0.46 | +0.13 | Comparative example |
| G | Comparative coupler (c) | — | −1.80 | +0.38 | Comparative example |
| H | " | Exemplified compound (A-5) | −0.67 | +0.20 | Comparative example |
| I | " | Exemplified compound (A-10) | −0.69 | +0.25 | Comparative example |
| J | Comparative coupler (d) | — | −1.82 | +0.44 | Comparative example |
| K | " | Exemplified compound (A-7) | −0.66 | +0.23 | Comparative example |
| L | " | Exemplified compound (A-11) | −0.64 | +0.26 | Comparative example |
| M | M-16 | — | −1.77 | +0.32 | Comparative example |
| N | " | Exemplified compouund (A-5) | −0.20 | +0.06 | This invention |
| O | " | Exemplified compound (A-10) | −0.19 | +0.08 | This invention |
| P | " | Comparative compound (1) | −0.78 | +0.31 | Comparative example |
| Q | M-17 | — | −1.78 | +0.33 | Comparative example |
| R | " | Exemplified compound (A-3) | −0.21 | +0.07 | This invention |
| S | " | Exemplified compound (A-5) | −0.19 | +0.05 | This invention |
| T | " | Comparative compound (2) | −0.71 | +0.30 | Comparative example |
| U | " | Comparative | −0.61 | +0.09 | Comparative |

TABLE 4-continued

| Sample | Magenta coupler | Discoloration inhibitor | Change in magenta density (Initial density: 2.0) | Change in density of yellowing in white background | Remarks |
|---|---|---|---|---|---|
| | | compound (3) | | | example |
| V | " | Comparative compound (4) | −1.02 | +0.31 | Comparative example |
| W | " | Comparative compound (5) | −0.83 | +0.32 | Comparative example |

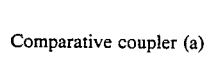

Comparative coupler (a)

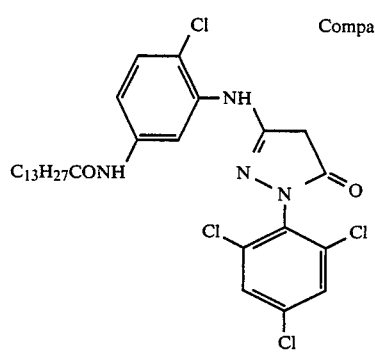

Coupler disclosed in U.S. Pat. No. 4,264,780

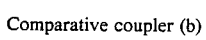

Comparative coupler (b)

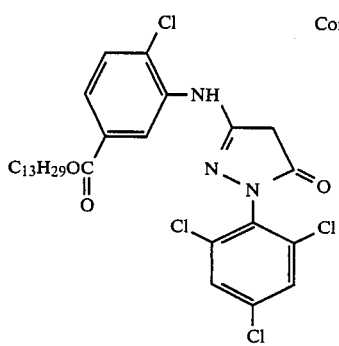

Coupler disclosed in U.S. Pat. No. 4,264,720

Comparative coupler (c)

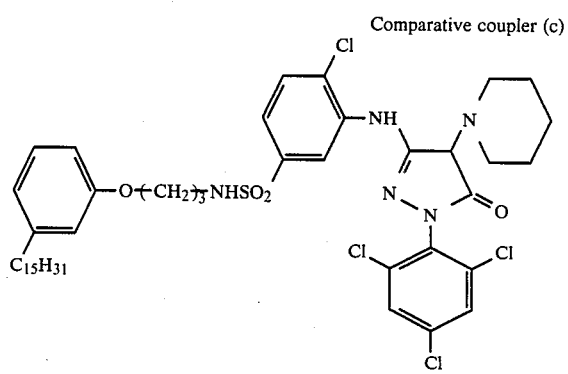

Coupler disclosed in U.S. Pat. No. 4,264,720

Comparative coupler (d)

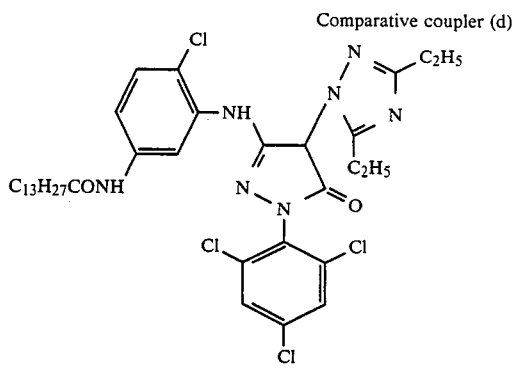

Coupler disclosed in Japanese Patent Application (OPI) No. 204037/1982

Comparative Compound (1)

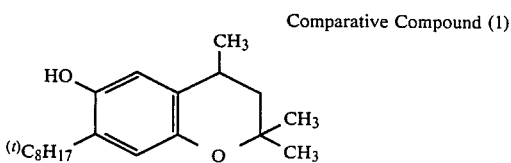

Compound disclosed in U.S. Pat. No. 3,432,300

Comparative Compound (2)

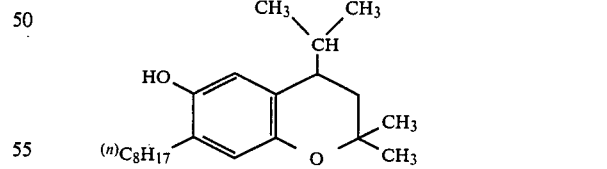

Compound disclosed in U.S. Pat. No. 3,698,909

Comparative Compound (3)

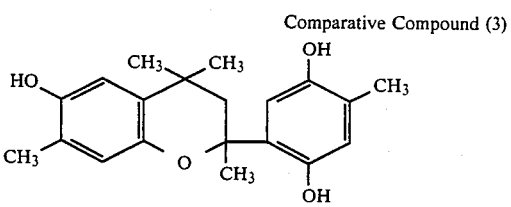

Compound disclosed in U.S. Pat. No. 4,113,495

Comparative Compound (4)

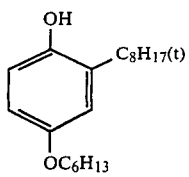

Compound disclosed in U.S. Pat. No. 3,930,866 and West Germany Patent (OLS) No. 2,146,668

Comparative Compound (5)

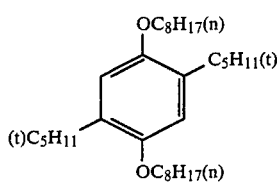

Compound disclosed in U.S. Pat. No. 4,254,216

As is apparent from the results of Table 4, the compound of formula (I) shows the superior effect of improving light fastness to the known similar compounds. The effect is remarkable when it is combined with a 5-pyrazolone type magenta coupler having the splitting-off group of formula (II).

EXAMPLE 9

Sample (a) of color photographic material was prepared by coating seven layers one over another on a paper support with both sides laminated with polyethylene, as shown in Table 5. (The coating weight is indicated in terms of g/m$^2$.)

TABLE 5

| 7th layer (Protective layer) | Gelatin | 1,000 mg/m$^2$ |
| 6th layer (UV light absorber) | UV light absorbent (*1) | 600 mg/m$^2$ |
| | Solvent for UV light absorbent (*2) | 300 mg/m$^2$ |
| | Gelatin | 800 mg/m$^2$ |
| 5th layer (Red-sensitive layer) | Silver chloro-bromide emulsion (silver bromide 50 mol %) | 300 mg/m$^2$ |
| | Cyan coupler (*3) | 400 mg/m$^2$ |

TABLE 5-continued

| | Coupler solvent (*2) | 400 mg/m$^2$ |
| | Gelatin | 1,000 mg/m$^2$ |
| 4th layer (Intermediate layer) | UV light absorbent (*1) | 600 mg/m$^2$ |
| | Solvent for UV light absorbent (*2) | 300 mg/m$^2$ |
| | Gelatin | 800 mg/m$^2$ |
| 3rd layer (Green-sensitive layer) | Silver chlorobromide emulsion (silver bromide 70 mol %) silver | 200 mg/m$^2$ |
| | Magenta coupler (*4) | 300 mg/m$^2$ |
| | Coupler solvent (*5) | 200 mg/m$^2$ |
| | Gelatin | 1,000 mg/m$^2$ |
| 2nd layer (Intermediate layer) | Gelatin | 1,000 mg/m$^2$ |
| 1st layer (Blue-sensitive layer) | Silver chlorobromide emulsion (silver bromide 80 mol %) silver | 400 mg/m$^2$ |
| | Yellow coupler (*6) | 300 mg/m$^2$ |
| | Coupler solvent (*7) | 150 mg/m$^2$ |
| | Gelatin | 1,200 mg/m$^2$ |
| Support | Paper support polyethylene-laminated (both sides) | |

Note to Table 5
(*1) UV light absorbent: 2-(2-hydroxy-2-sec-butyl-5-tert-butylphenyl)-benzotriazole
(*2) Solvent: dibutyl phthalate
(*3) Coupler: 2-[α-(2,4-di-tert-pentylphenoxy)butanamido]4,6-dichloro-5-methylphenol
(*4) Coupler: 1-(2,4,6-trichlorophenyl)-3-(2-chloro-5-tetradecano amido)anilino-4-(2-butoxy-5-tert-octylphenylthio)-2-pyrazolin-5-on
(*5) Solvent: tricresyl phosphate
(*6) Coupler: α-pyvaloyl-α-(2,4-dioxy-5,5'-dimethyloxazolidin-3-yl)-2-chloro-5-[α-(2,4-di-tert-pentyloxy)butanamido] acetanilide
(*7) Solvent: dioctylbutyl phosphate Sample (b) to (k) were prepared in the same manner as above except that the third layer was incorporated with one or two kinds of discoloration inhibitors as shown in Table 6.

Each sample was exposed to green light through a continuous wedge and processed in the same manner as in Example 8. The dyes thus formed were examined for light fastness by exposure to a fluorescent fading tester (20,000 lux) for 4 weeks. The results are shown in Table 6.

TABLE 6

| Sample | Discoloration inhibitor | Amount added (mol % based on coupler) | Change in magenta density (initial density: 1.0) | Remarks |
| --- | --- | --- | --- | --- |
| a | — | — | −0.78 | Comparative example |
| b | Exemplified compound (A-5) | 50 | −0.11 | This invention |
| c | Exemplified compound (A-10) | 50 | −0.12 | This invention |
| d | Exemplified compound (G-3) | 50 | −0.23 | Comparative example |
| e | Exemplified compound (G-12) | 50 | −0.31 | Comparative example |
| f | Exemplified compound (G-15) | 50 | −0.39 | Comparative example |
| g | Exemplified compound (G-16) | 50 | −0.68 | Comparative example |
| h | Exemplified compound (A-5) Exemplified compound (G-3) | 50 50 | −0.06 | This invention |
| i | Exemplified compound (A-5) Exemplified compound (G-12) | 50 50 | −0.05 | This invention |
| j | Exemplified compound (A-5) Exemplified compound (G-15) | 50 50 | −0.05 | This invention |
| k | Exemplified compound (A-5) Exemplified compound (G-16) | 50 50 | −0.07 | This invention |

It is noted from Table 6 that the compound of formula (I) shows superior effect of improving light fastness to the known discoloration inhibitor, in combination with a 5-pyrazolone type magenta coupler having the group represented by formula (II). This effect is further remarkable when it is used in combination with a known discoloration inhibitor.

EXAMPLE 10

Sample (l), (m), and (n) were prepared in the same manner as in Sample (b) of Example 9, except that the third layer is incorporated with a magenta coupler (M-17) and a discoloration inhibitor (A-5) of this invention, as shown in Table 7. They were exposed and developed, together with Samples (a) and (b), in the same manner as in Example 9.

TABLE 7

| Sample | Points changed |
|---|---|
| g | Same as the sample shown in Table 5 of Example 9 except that as the cyan coupler is replaced by 2-[α-(2,4-di-tert-pentylphenoxy)-butanamido-4,6-dichloro-5-ethylphenol. |
| h | Same as the sample shown in Table 5 of Example 9 except that the cyan coupler is replaced by an equimolar mixture of the coupler in sample (g) and 5-[2-(4-tert-amyl-2-chlorophenoxy)octanamido]-4-chloro-2-(2-chlorobenzamido)phenol. The coating weight is 1.1 times more than that in Table 5. |
| i | Same as the sample shown in Table 5 of Example 9 except that the yellow coupler is incorporated with 20 mol % (based on the yellow coupler) of bis-[2,2,6,6-tetramethyl-1-(1-oxo-2-propenyl)-4-piperidinyl]-1,1-bis-[(3,5-di-tert-butyl-4-hydroxyphenyl)methyl]-propanediol. |

The dye image thus obtained was stored at 100° C. for 7 days to find that the magenta density remained almost unchanged. After storage at 60° C. and 90%RH for 6 weeks the magenta density changed very little. There was very little stain in the white background. These results are shown in Table 8.

TABLE 8

| | Change in magenta density (initial density = 1.0) | |
|---|---|---|
| Sample | at 100° C. for 7 days | at 60° C., 90% RH for 6 weeks |
| a | 0.95 (0.16) | 0.96 (0.17) |
| b | 0.99 (0.14) | 0.98 (0.15) |
| l | 0.99 (0.14) | 0.98 (0.15) |
| m | 0.98 (0.13) | 0.99 (0.14) |
| n | 1.00 (0.14) | 0.98 (0.14) |

Note:
Each value in parenthesis indicates the density (stain) of the white background measured through a blue filter.

It is noted from Table 8 that the 5-pyrazolone type magenta coupler having the splitting-off group of formula (II) forms a color image which is stable to heat and/or humidity and also forms a white background which is stable with respect to stain. This effect remains unchanged even when the composition in the adjacent layer is changed.

EXAMPLE 11

10 g of magenta coupler, 1-(2,4,6-trichlorophenyl)-3-{(2-chloro-5-tetradecanamido)anilino}-2-pyrazolin-5-on was dissolved in 20 ml of tricresyl phosphate and 20 ml of ethyl acetate. The resulting solution was emulsified and dispersed into 80 g of gelatin solution containing 8 ml of 1% aqueous solution of sodium dodecylbenzenesulfonate.

The thus obtained emulsified dispersion was mixed with 145 g (7 g as Ag) of green-sensitive silver chlorobromide (Br 50 mol%) emulsion. Sodium dodecylbenzenesulfonate as a coating auxiliary was added. The resulting emulsion was coated on a paper support with both sides laminated with polyethylene. The coating amount of the coupler was 400 mg/m$^2$.

The emulsion layer was further coated with a gelatin protective layer (gelatin 1 g/m$^2$). Thus there was obtained Sample A.

Samples B to Q were prepared in the same manner as mentioned above, except that each of them was incorporated with a mixture of the coupler of formula (IX) of this invention and the compound of formula (I) or a comparative compound as shown in Table 9. The amount of the compound of formula (I) or comparative compound was 50 mol% based on the amount of the coupler used.

Each sample was exposed for 1 second at 1000 lux and treated with the following processing solutions.

| Developing solution | |
|---|---|
| Benzyl alcohol | 15 ml |
| Diethylenetriamine pentaacetic acid | 5 g |
| KBr | 0.4 g |
| Na$_2$SO$_3$ | 5 g |
| Na$_2$CO$_3$ | 30 g |
| Hydroxylamine sulfate | 2 g |
| 4-amino-3-methyl-N—ethyl-N—β-(methanesulfonamide)ethylaniline.3/2H$_2$SO$_4$.H$_2$O | 4.5 g |
| Water to make 1000 ml | pH 10.1 |
| Bleach-fixing solution | |
| Ammonium thiosulfate (70 wt %) | 150 ml |
| Na$_2$SO$_3$ | 5 g |
| Na [Fe(EDTA)] | 40 g |
| EDTA | 4 g |
| Water to make 1000 ml | pH 6.8 |

| Processing step | Temperature | Time |
|---|---|---|
| Developing | 33° C. | 3 minute 30 second |
| Bleach-fixing | 33° C. | 1 minute 30 second |
| Washing with water | 28–35° C. | 3 minute |

The dye image formed on each sample was examined for light fastness by exposing the sample to a xenon tester (200,000 lux) with an ultra-violet light absorbing filter (a product of Fuji Photo Film Co., Ltd.) (absorbing 400 nm and below) for 5 days. Change in density (initial density: 2.0) was measured with a Macbeth densitometer RD-514 (with status AA filter). The results are shown in Table 9.

TABLE 9

| Sample | Magenta coupler | Discoloration inhibitor | Change in magenta density (Initial density: 2.0) | Change in density in white background by yellowing | Remarks |
|---|---|---|---|---|---|
| A | M-25 | — | −1.54 | +0.27 | Comparative example |
| B | " | Comparative compound (1) | −0.42 | +0.10 | Comparative example |
| C | " | Comparative compound (2) | −0.51 | +0.11 | Comparative example |
| D | " | Comparative compound (3) | −0.49 | +0.11 | Comparative example |
| E | " | Comparative | −0.57 | +0.07 | Comparative |

TABLE 9-continued

| Sample | Magenta coupler | Discoloration inhibitor | Change in magenta density (Initial density: 2.0) | Change in density in white background by yellowing | Remarks |
|---|---|---|---|---|---|
| | | compound (4) | | | example |
| F | " | Comparative compound (5) | −0.71 | +0.26 | Comparative example |
| G | " | Exemplified compound (A-3) | −0.27 | +0.06 | This invention |
| H | " | Exemplified compound (A-5) | −0.25 | +0.05 | This invention |
| I | " | Exemplified compound (A-10) | −0.26 | +0.06 | This invention |
| J | " | Exemplified compound (A-17) | −0.22 | +0.04 | This invention |
| K | M-31 | — | −1.46 | +0.25 | Comparative example |
| L | " | Comparative compound (6) | −0.70 | +0.23 | Comparative example |
| M | " | Comparative compound (7) | −0.72 | +0.27 | Comparative example |
| N | " | Exemplified compound (A-3) | −0.27 | +0.07 | This invention |
| O | " | Exemplified compound (A-4) | −0.26 | +0.05 | This invention |
| P | " | Exemplified compound (A-7) | −0.24 | +0.05 | This invention |
| Q | " | Exemplified compound (A-12) | −0.25 | +0.06 | This invention |

Comparative Compound (1)

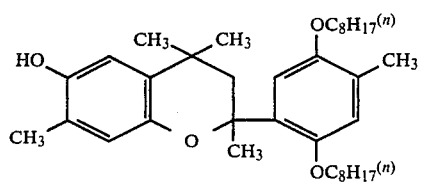

Compound disclosed in U.S. Pat. No. 4,264,720

Comparative Compound (2)

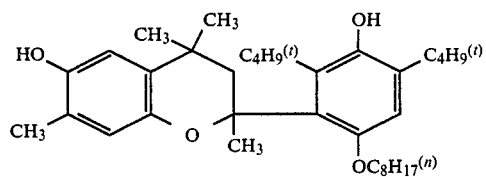

Compound disclosed in U.S. Pat. No. 4,264,720

Comparative Compound (3)

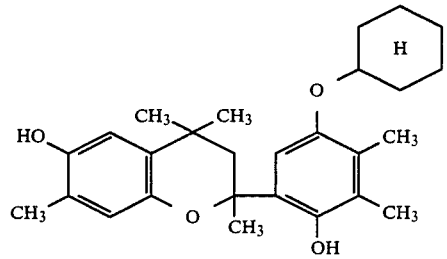

Compound disclosed in U.S. Pat. No 4,264,720

Comparative COmpound (4)

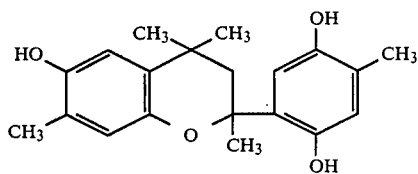

Compound disclosed in U.S. Pat. No. 4,113,495

Comparative Compound (5)

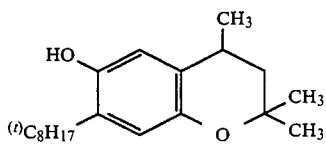

Compound disclosed in U.S. Pat. No. 3,432,300

Comparative Compound (6)

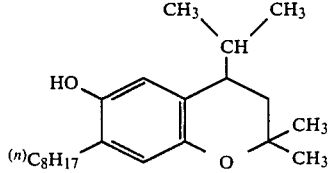

Compound disclosed in U.S. Pat. No. 3,698,909

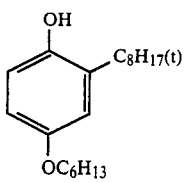

Comparative Compound (7)

Compound disclosed in U.S. Pat. No. 3,930,866 and West Germany Patent Application (OLS) No. 2,146,668

It is noted from Table 9 that the samples of this invention are superior in the prevention of fading by light to the comparative samples incorporated with a known discoloration inhibitor of the similar structure. In addition, they are superior in the prevention of yellowing by light in the white background portion.

EXAMPLE 12

Sample (a) of color photographic material was prepared by coating seven layers one over another on a paper support with both sides laminated with polyethylene, in the same manner as described in Table 5 of Example 9 except that in the 3rd layer magenta coupler M-25 is added to.

Samples (b) to (f) were prepared in the same manner as above except that the third layer was incorporated with one or two kinds of discoloration inhibitors as shown in Table 10.

Each sample was exposed to green light through a continuous wedge and processed in the same manner as in Example 8. The dye images thus formed were examined for light fastness by exposure to a fluorescent fading tester (20,000 lux) for 4 weeks. The results are shown in Table 10.

TABLE 10

| Sample | Discoloration inhibitor | Amount added (mol % based on coupler) | Change in magenta density (initial density: 1.0) | Remarks |
|---|---|---|---|---|
| a | — | — | −0.51 | Comparative example |
| b | Exemplified compound (A-5) | 50 | −0.08 | This invention |
| c | " | 100 | −0.05 | This invention |
| d | Comparative compound (1) | 50 | −0.18 | Comparative example |
| e | " | 100 | −0.17 | Comparative example |
| f | Exemplified compound (A-5) 2,5-di-tert-octylhydrquinone | 50 50 | −0.04 | This invention |

It is noted from Table 11 that the sample of this invention is superior in the prevention of discoloration by light. The effect is enhanced when the amount of the discoloration inhibitor is increased.

EXAMPLE 13

Samples (g), (h), and (i) were prepared in the same manner as in Sample (b) of Example 12, in which third layer is incorporated with a magenta coupler (M-25) and a discoloration inhibitor (A-5), except that the fifth or first layer was changed as shown in Table 11. They were exposed and developed, together with Samples (a) and (b), in the same manner as in Example 12.

TABLE 11

| Sample | Points changed |
|---|---|
| g | Same as the sample shown in Example 12, except that the cyan coupler in the fifth layer is replaced by 2-[α-(2,4-di-tert-pentylphenoxy)-butanamido-4,6-dichloro-5-ethylphenol. (Refer to Table 5 of Example 9). |
| h | Same as the sample shown in Example 12, except that the cyan coupler in the fifth layer is replaced by an equimolar mixture of the coupler in sample (g) and 5-[2-(4-tert-amyl-2-chlorophenoxy]-octanamido]-4-chloro-2-(2-chlorobenzamide)phenol. The coating weight is 1.1 times more than that in Table 5 of Example 9. |
| i | Same as the sample shown in Example 12, except that the yellow coupler in the first layer is incorporated with 20 mol % (based on the yellow coupler) of bis[2,2,6,6-tetramethyl-1-(1-oxo-2-propenyl)-4-piperidinyl]-1,1-bis[(3,5-di-tert-butyl-4-hydroxyphenyl)-methyl]-propanediol. (Refer to Table 5 of Example 9). |

The dye image thus obtained was stored at 100° C. for 7 days to find that the magenta density remained almost unchanged. After storage at 60° C. and 90%RH for 6 weeks the magenta density changed very little. There was very little stain in the white background portion (See Table 12).

TABLE 12

| Sample | Change in magenta density (initial density = 1.0) | |
|---|---|---|
| | at 100° C. for 7 days | at 60° C., 90% RH for 6 weeks |
| a | 0.94 (0.38) | 0.93 (0.43) |
| b | 0.97 (0.17) | 0.97 (0.17) |
| g | 0.97 (0.14) | 0.98 (0.16) |
| h | 0.98 (0.15) | 0.98 (0.15) |
| i | 0.99 (0.14) | 0.98 (0.16) |

Note:
Each value in parenthesis indicates the density (stain) of the white background measured through a blue filter.

It is noted from Table 12 that the 3-anilino-5-pyrazolone type magenta represented by formula (IX) forms a color image which is stable to heat and/or humidity and also forms a white background which is stable with respect to stain. This effect remains unchanged even when the composition in the adjacent layer is changed.

As many apparently widely different embodiments of this invention may be made without departing from the spirit and scope thereof, it is to be understood that the invention is not limited to the specific embodiments thereof except as defined in the appended claims.

What is claimed is:

1. A silver halide color photographic material comprising at least one silver halide emulsion layer having associated therewith at least one compound represented by formula (X) and at least one pyrazolone type magenta coupler having at the coupling position thereof a coupling off group represented by formula (II)

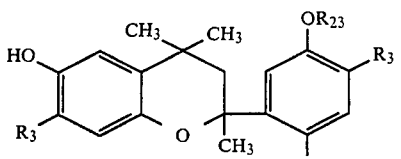
(X)

—S—R   (II)

wherein R represents an alkyl group or an aryl group; each pair of $R_3$ and $R_3$ has the same meaning and represents a hydrogen atom, alkyl group, aryl group, alkoxy group, aryloxy group, alkylthio group, arylthio group, acylamino group, diacylamino group, sulfonamido group, alkylamino group, acyl group, alkoxycarbonyl group, acyloxy group, or halogen atom; $R_{23}$ and $R_{24}$ each represents a hydrogen atom or alkyl group, provided that both of them are not hydrogen atoms or alkyl groups at the same time and when R and $R_3$ are alkyl groups or aryl groups or those groups containing partially alkyl groups or aryl groups, such alkyl groups or aryl groups may be further substituted by other substituent groups.

2. The silver halide color photographic material as described in claim 1, wherein the pyrazolone type magenta coupler is selected from the compounds represented by formula (III)

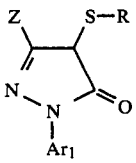
(III)

wherein R has the same meaning as in formula (II); $Ar_1$ represents an aryl group; and Z represents an acylamino group, anilino group, or ureido group.

3. The silver halide color photographic material as described in claim 2, wherein the pyrazolone type magenta color is selected from the compounds represented by formula (IV)

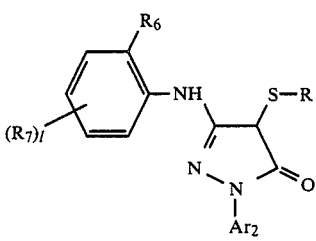
(IV)

wherein R has the same meaning as in formula (II); $Ar_2$ represents a phenyl group having at least one substituent selected from the group consisting of a halogen atom, alkyl group, alkoxy group, alkoxycarbonyl, or cyano group; $R_6$ represents a halogen atom or alkoxy group; $R_7$ represents a hydrogen atom, halogen atom, alkyl group, alkoxy group, acylamino group, sulfonamido group, sulfamoyl group, carbamoyl group, diacylamino group, alkoxycarbonyl group, alkoxysulfonyl group, aryloxysulfonyl group, alkanesulfonyl group, arylsulfonyl group, alkylthio group, arylthio group, alkyloxycarbonylamino group, alkylureido group, acryl group, nitro group, carboxyl group, or trichloromethyl group; and l is an integer of 1 to 4 with the proviso that when l is greater than 1, the groups represented by $R_7$ may be the same or different.

4. The silver halide color photographic material as described in claim 3, wherein the pyrazolone type magenta coupler is selected from the compounds represented by formula (V), (VI) or (VII):

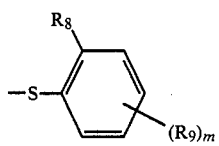
(V)

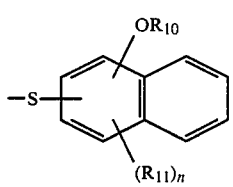
(VI)

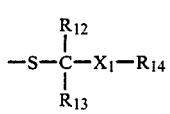
(VII)

wherein $R_8$ denotes a halogen atom, hydroxyl group, alkyl group, alkoxyl group, or aryl group; $R_9$ denotes a hydrogen atom, halogen atom, hydroxyl group, alkyl group, alkoxyl group, or aryl group with the proviso that at least one of $R_8$ and $R_9$ is an alkoxyl group; $R_{10}$ denotes an alkyl group or aryl group; $R_{11}$ denotes a halogen atom; alkyl group, alkoxyl group, or aryl group; m is an integer of 1 to 4, and n is an integer of 1 to 5 with the proviso that when m or n is greater than 1, the groups represented by $R_9$ or $R_{11}$ may be the same or different; $R_{12}$ denotes a hydrogen atom, alkyl group or aryl group; $R_{13}$ denotes a hydrogen atom, alkyl group, aryl group, alkoxyl group, aryloxy group, alkoxycarbonyl group, aryloxycarbonyl group, carbamoyl group, acyl group, or carboxyl group; $X_1$ denotes an alkylene group, alkenylene group, arylene group,

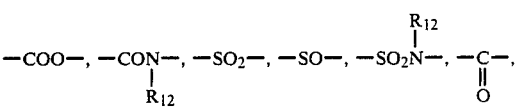

—O—, or —S—; and $R_{14}$ denotes a hydrogen atom, alkyl group, aryl group, or heterocyclic group.

5. The silver halide color photographic material as described in claim 4, wherein the sum of the carbon atoms for $R_{13}$ and $R_{14}$ is as least 12.

6. The silver halide color photographic material as described in claim 3, wherein the pyrazolone type magenta coupler is selected from the compounds represented by formula (VIII) below

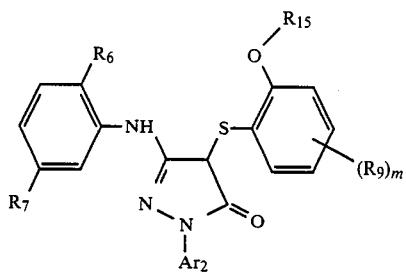

(VIII)

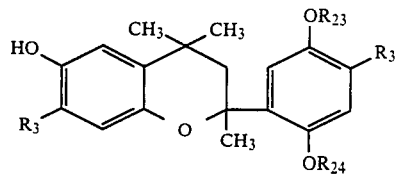

(X)

and

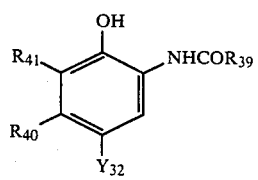

(IX)

wherein Ar$_2$, R$_6$, and R$_7$ have the same meaning as in formula (IV); R$_9$ represents a hydrogen atom, halogen atom, hydroxyl group, alkyl group, alkoxy group, or aryl group; m is an integer of 1 to 4; R$_{15}$ represents an aliphatic group or aromatic group which may have (a) a halogen atom, (b) a cyano group, (c) an aliphatic, aromatic, or heterocyclic sulfonyl group, sulfinyl grup, or sulfonyl group, (d)

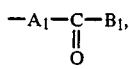

or (e) —(A$_2$—M)mB$_2$ wherein A$_1$ denotes a single bond, oxygen atom, sulfur atom, imino group, or divalent aliphatic, aromatic, or heterocyclic group; B$_1$ denotes a hydroxyl group, aliphatic or aromatic oxy group, hydrogen atom, aliphatic group, aromatic group, heterocyclic group, or acyclic amino group or hydrazino group which may have a substituent group; A$_2$ denotes a single bond, or divalent aliphatic, aromatic, or heterocyclic group; B$_2$ denotes a hydrogen atom, aliphatic group, aromatic group or heterocyclic group; M denotes an oxygen atom, sulfur atom, or imino group; and m denotes an integer of 1 to 4.

7. The silver halide color photographic material as described in claim 3, wherein:

Ar$_2$ is a substituted phenyl group wherein the substituent group is selected from the group consisting of a halogen atom, an alkyl group having 1 to 22 carbon atoms, an alkoxyl group having 1 to 22 carbon atoms, an alkoxycarbonyl group having 2 to 23 carbon atoms and a cyano group.

8. The silver halide color photographic material as described in claim 1, wherein the compound represented by formula (X) is included in an amount of 100 to 200 mol% based on the pyrazolone type magenta coupler.

9. The silver halide color photographic material as described in claim 1, wherein the pyrazolone type magenta coupler is added in an amount of $2 \times 10^{-3}$ to $5 \times 10^{-1}$ mol per 1 mol of silver.

10. A silver halide color photographic material comprising at least one silver halide emulsion layer having associated therewith at least one kind of the compound selected from the compounds represented by the formula (X) and at least one pyrazolone type magenta coupler represented formula (IX)

wherein R$_3$ represents a methyl group; R$_{23}$ and R$_{24}$ each represents a hydrogen atom or alkyl group, provided that one of R$_{23}$ and R$_{24}$ is a hydrogen atom and that both of them are not hydrogen atoms at the same time; Ar$_3$ represents an aryl group; R$_{25}$ represents a halogen atom or alkoxy group; and R$_{26}$ and R$_{27}$ each represents a hydrogen atom, halogen atom, alkyl group, alkoxy group, acylamino group, sulfonamide group, sulfamoyl group, carbamoyl group, diacylamino group, alkoxycarbonyl group, alkoxysulfonyl group, aryloxysulfonyl group, alkanesulfonyl group, arylsulfonyl group, alkylthio group, arylthio group, alkyloxycarbonylamino group, alkylureido group, acyl group, nitro group, carboxyl group, or trichloromethyl group.

11. The silver halide color photographic material as described in claim 10, wherein Ar$_3$ in formula (IX) is a phenyl group having at least one substituent selected from a halogen atom, alkyl group, alkoxy group, alkoxycarbonyl group, or cyano group.

12. The silver halide color photographic material as described in claim 10, wherein the compound represented by formula (X) is included in an amount of 100 to 200 mol% based on the 5-pyrazolone type magenta coupler.

13. The silver halide color photographic material as described in claim 10, wherein the 5-pyrazolone type magenta coupler is added in an amount of $2 \times 10^{-3}$ to $5 \times 10^{-1}$ mol per 1 mol of silver.

14. The silver halide color photographic material as described in claim 1, further comprising at least one cyan coupler represented by formula (XII) or (XIII)

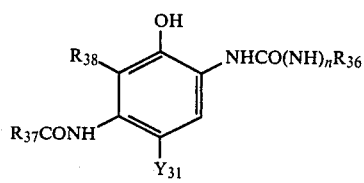

(XII)

(XIII)

wherein $R_{36}$, $R_{37}$, and $R_{39}$ represent substituted or unsubstituted aliphatic, aromatic, or heterocyclic groups; $R_{38}$ and $R_{41}$ represent hydrogen atoms, halogen atoms, aliphatic groups, aromatic groups, or acylamino groups; $R_{38}$ represents a group of nonmetallic atoms which forms, together with $R_{37}$, a nitrogen-containing 5- or 6-membered ring; $R_{40}$ represents an aliphatic group having at least 2 carbon atoms which may be further substituted; $Y_{31}$ and $Y_{32}$ represent hydrogen atoms or the groups that can be split-off upon an oxidation coupling reaction with the developint agent; and n is 0 or 1.

15. The silver halide color photographic material as described in claim 14, wherein:
$R_{36}$ is an aryl group further substituted by a halogen atom, an alkyl group, an alkoxyl group, an aryloxy group, an acylamino group, an acyl group, a carbamoyl group, a sulfonamido group, a sulfamoyl group, a sulfonyl group, a sulfamido group, an oxycarbonyl group, or a cyano group;
$R_{37}$ is a substituted or unsubstituted alkyl group or aryl group;
$R_{38}$ is a hydrogen atom;
$R_{39}$ is a substituted or unsubstituted alkyl group or aryl group;
$R_{40}$ is an alkyl group having 2 to 15 carbon atoms or a methyl group having a substituent having 1 or more carbon atoms;
$R_{41}$ is a hydrogen atom or halogen atom; and
$Y_{31}$ and $Y_{32}$ are a hydrogen atom, a halogen atom, an alkoxyl group, an aryloxy group, an acyloxy group, or a sulfonamido group.

16. The silver halide color photographic material as described in claim 1, further comprising at least one yellow coupler represented by formula (XIV)

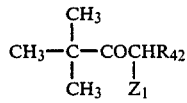

(XIV)

wherein $R_{42}$ denotes a substituted or unsubstituted N-phenylcarbamoyl group; $Z_1$ denotes a hydrogen atom or a group which is split-off upon coupling reaction with an oxidation product of the developing agent; and a dimer or polymer may be formed through $Z_1$.

17. The silver halide color photographic material as described in claim 16, wherein $R_{42}$ is represented by formula (XV)

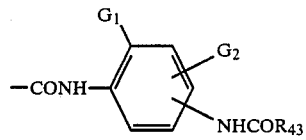

(XV)

wherein $G_1$ represents a halogen atom or alkoxyl group; $G_2$ represents a hydrogen atom, halogen atom, or alkoxyl group which may have a substituent; and $R_{43}$ denotes an alkyl group which may have a substituent.

18. The silver halide color photographic material as described in claim 1, further comprising at least one discoloration inhibitor represented by formulas (XVI) and (XVII)

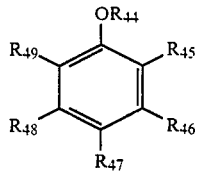

(XVI)

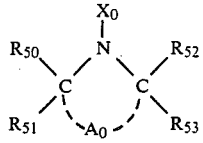

(XVII)

wherein $R_{44}$ represents a hydrogen atom, an aliphatic group, an aromatic group, a heterocyclic group, or a substituted silyl group

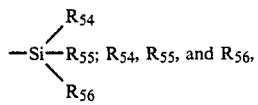

$R_{54}$, $R_{55}$, and $R_{56}$, which are the same or different, each represents aliphatic groups, aromatic groups, aliphatic oxy groups, or aromatic oxy groups; $R_{45}$, $R_{46}$, $R_{47}$, $R_{48}$, and $R_{49}$ may be the same or different, each denoting a hydrogen atom, an alkyl group, an aryl group, an alkoxyl group, a hydroxyl group, mono- or dialkylamino group, an imino group, and an acylamino group; $R_{44}$ and $R_{45}$ may combine with each other to form a 5- or 6-membered ring; $R_{50}$, $R_{51}$, $R_{52}$, and $R_{53}$ may be the same or different, each denoting a hydrogen atom and an alkyl group; $X_0$ denotes a hydrogen atom, an aliphatic group, an acyl group, an aliphatic or an aromatic sulfonyl group, an aliphatic or an aromatic sulfinyl group, an oxyradical group, or hydroxyl group; and $A_0$ denotes a group of non-metallic atoms necessary to form a 5-, 6-, or 7-membered ring.

19. The silver halide color photographic material as described in claim 1, further comprising an ultraviolet light absorbent represented by formula (XI)

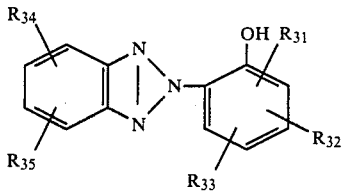

(XI)

wherein $R_{31}$, $R_{32}$, $R_{33}$, $R_{34}$, and $R_{35}$, which may be the same or different, each represents a hydrogen atom, halogen atom, nitro group, hydroxyl group, alkyl group, alkenyl group, aryl group, alkoxyl group, acyloxy group, aryloxy group, alkylthio group, arylthio group, mono- or dialkylamino group, acylamino group, or 5- or 6-membered heterocyclic group containing at least oxygen or nitrogen.

20. The silver halide color photographic material as described in claim 19, comprising $1 \times 10^{-4}$ to $2 \times 10^{-3}$ mol/m² of said ultraviolet light absorbent.

21. The silver halide color photographic materials as described in claim 18, further comprising at least one cyan, magenta or yellow coupler.

22. A silver halide color photographic material as described in claim 21, wherein the compound represented by formula (XVI) or (XVII) is used in an amount of 0.5 to 200 wt% based on the yellow coupler or cyan coupler.

23. A silver halide color photographic material comprising at least one silver halide emulsion layer having associated therewith at least one compound of the formula:

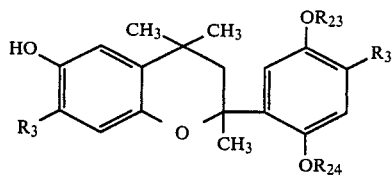

wherein $R_3$ represents a methyl group; $R_{23}$ and $R_{24}$ each represents a hydrogen atom or alkyl group, provided that one of $R_{23}$ and $R_{24}$ is a hydrogen atom and that both of them are not hydrogen atoms at the same time.

24. The silver halide color photographic material as described in claim 23, further comprising at least one cyan, magenta or yellow coupler.

25. A silver halide color photographic material comprising at least one silver halide emulsion layer having associated therewith at least one compound represented by formula (X) and at least one pyrazolone type magenta coupler having at the coupling position thereof a coupling off group represented by formula (II)

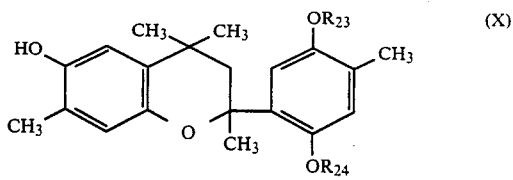

$$-S-R \qquad (II)$$

$R_{23}$ and $R_{24}$ each represents a hydrogen atom or alkyl group, provided that both of them are not hydrogen atoms or alkyl groups at the same time.

* * * * *